(12) United States Patent
Messerschmidt

(10) Patent No.: US 11,340,155 B2
(45) Date of Patent: May 24, 2022

(54) SYSTEMS AND METHODS FOR BLOOD ANALYSIS

(71) Applicant: NUEON INC., Menlo Park, CA (US)

(72) Inventor: Robert G. Messerschmidt, Menlo Park, CA (US)

(73) Assignee: NUEON INC., Menlo Park, CA (US)

(*) Notice: Subject to any disclaimer, the term of this patent is extended or adjusted under 35 U.S.C. 154(b) by 0 days.

(21) Appl. No.: 17/250,006

(22) PCT Filed: Apr. 30, 2019

(86) PCT No.: PCT/US2019/030052
§ 371 (c)(1),
(2) Date: Oct. 28, 2020

(87) PCT Pub. No.: WO2019/213166
PCT Pub. Date: Nov. 7, 2019

(65) Prior Publication Data
US 2021/0223168 A1 Jul. 22, 2021

Related U.S. Application Data

(60) Provisional application No. 62/664,872, filed on Apr. 30, 2018.

(51) Int. Cl.
G01N 33/48 (2006.01)
G01N 21/25 (2006.01)
(Continued)

(52) U.S. Cl.
CPC ........... G01N 21/255 (2013.01); A61B 5/151 (2013.01); G01N 33/49 (2013.01); G01N 2201/0221 (2013.01); G01N 2201/0636 (2013.01)

(58) Field of Classification Search
CPC .... G01N 33/49; G01N 15/05; G01N 15/1434; A61B 5/14532; A61B 5/1455
(Continued)

(56) References Cited

U.S. PATENT DOCUMENTS 5,636,640 A 6/1997 Staehlin
5,801,057 A 9/1998 Smart
(Continued)

FOREIGN PATENT DOCUMENTS

WO 2015009970 1/2015
WO 2015131151 9/2015
(Continued)

OTHER PUBLICATIONS

International Search Report and Written Opinion for PCT/US2019/030052 (dated Sep. 27, 2019).
(Continued)

Primary Examiner — Md M Rahman
(74) Attorney, Agent, or Firm — FisherBroyles LLP; John Shimmick

(57) ABSTRACT

A blood sample collector can be used to collect a blood sample from a subject. The blood sample collector can be placed in a receptacle of a spectrometer to measure spectral data from the blood sample while the blood sample separates. The container may comprise a window to allow light such as infrared light to pass through the container, with the blood sample at least partially separating within the container between spectral measurements, which can provide improved accuracy of the measurements and additional information regarding the sample. The container may comprise an elongate axis and the container configured for placement in the spectrometer receptacle with the elongate axis extending toward a vertical direction in order to improve gravimetric separation of the blood sample. The
(Continued)

spectrometer can be configured to measure the blood sample at a plurality of heights along the sample as the sample separates.

23 Claims, 38 Drawing Sheets

(51) Int. Cl.
*A61B 5/151* (2006.01)
*G01N 33/49* (2006.01)

(58) Field of Classification Search
USPC .......................................................... 356/39
See application file for complete search history.

(56) References Cited

U.S. PATENT DOCUMENTS

| 6,866,675 | B2 | 3/2005 | Perez |
| 8,690,798 | B2 | 4/2014 | Douglas |
| 8,821,413 | B2 | 9/2014 | Effenhauser |
| 10,337,984 | B2 | 7/2019 | Messerschmidt |
| 10,760,965 | B2 | 9/2020 | Messerschmidt |
| 2002/0103499 | A1 | 8/2002 | Perez |
| 2005/0270528 | A1 | 12/2005 | Geshwind |
| 2010/0196945 | A1 | 8/2010 | Forsell |
| 2010/0245803 | A1 | 9/2010 | Samsoondar |
| 2010/0252721 | A1 | 10/2010 | Xu |
| 2014/0310019 | A1 | 10/2014 | Blander |
| 2015/0055121 | A1 | 2/2015 | Forsell |
| 2015/0338338 | A1 | 11/2015 | Messerschmidt |
| 2016/0123869 | A1 | 5/2016 | Messerschmidt |
| 2017/0172480 | A1 | 6/2017 | Braig |
| 2017/0350814 | A1 | 12/2017 | Messerschmidt |
| 2018/0085003 | A1 | 3/2018 | Goldring |
| 2018/0136193 | A1 | 5/2018 | Messerschmidt |
| 2019/0226910 | A1 | 7/2019 | Messerschmidt |
| 2019/0269358 | A1 | 9/2019 | Messerschmidt |
| 2019/0323950 | A1 | 10/2019 | Messerschmidt |

FOREIGN PATENT DOCUMENTS

| WO | 2016086071 | 6/2016 |
| WO | 2016168090 | 10/2016 |
| WO | 2017165403 | 9/2017 |
| WO | 2018085699 | 5/2018 |
| WO | 2019213166 | 11/2019 |

OTHER PUBLICATIONS

DeVerse, R.A., et al., "Realization of the Hadamard Multiplex Advantage Using a Programmable Optical Mask in a Dispersive Flat-Field Near-Infrared Spectrometer," Applies Spectroscopy, 54(12):1751-1758 (Dec. 1, 2000).

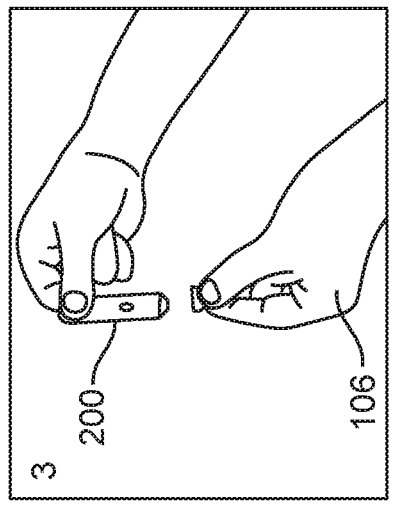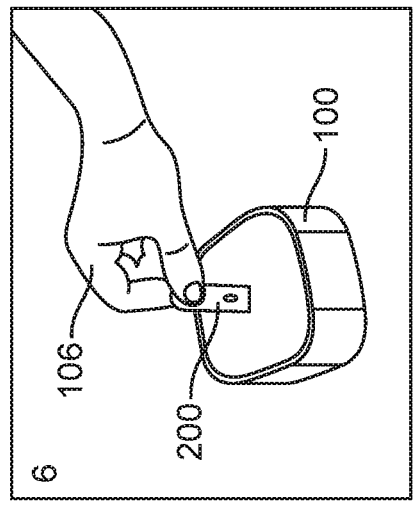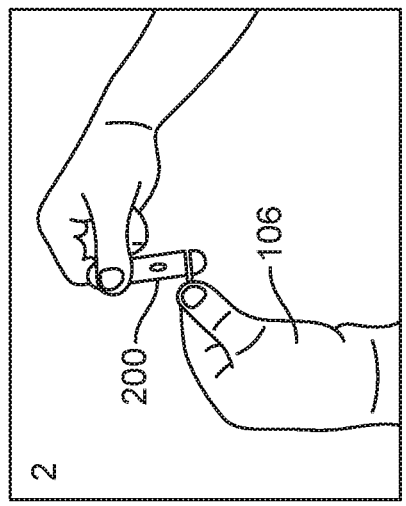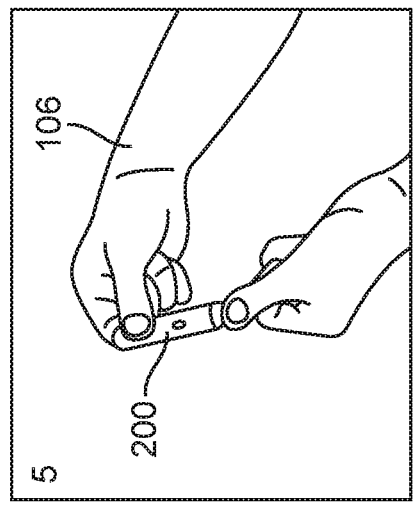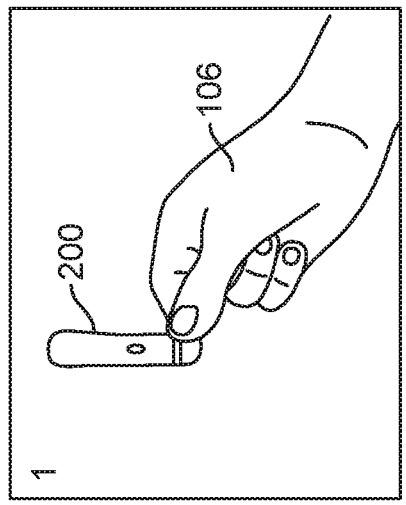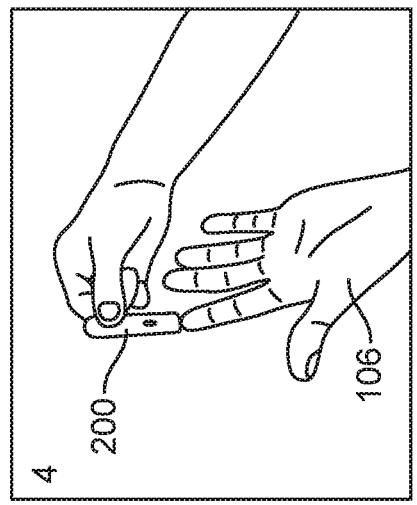
FIG. 1F

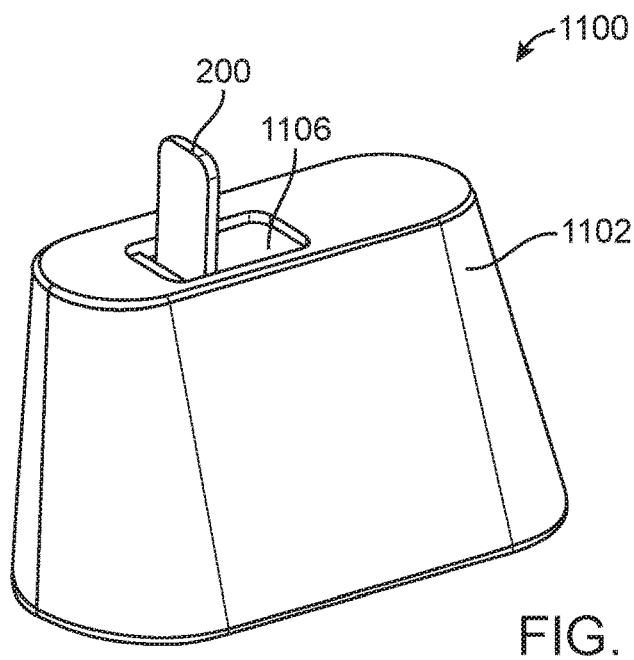
FIG. 12
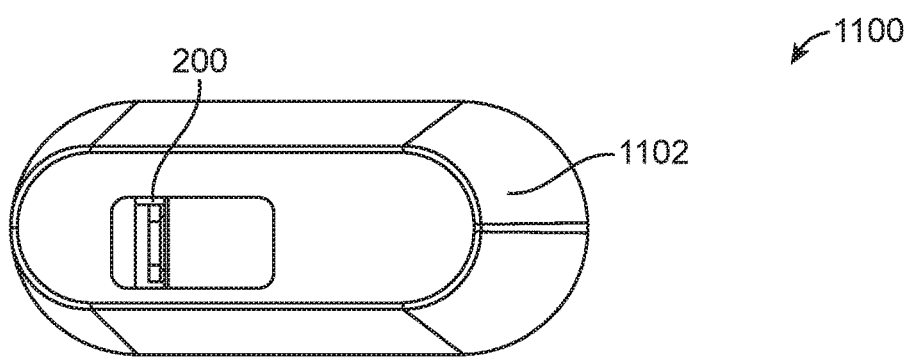
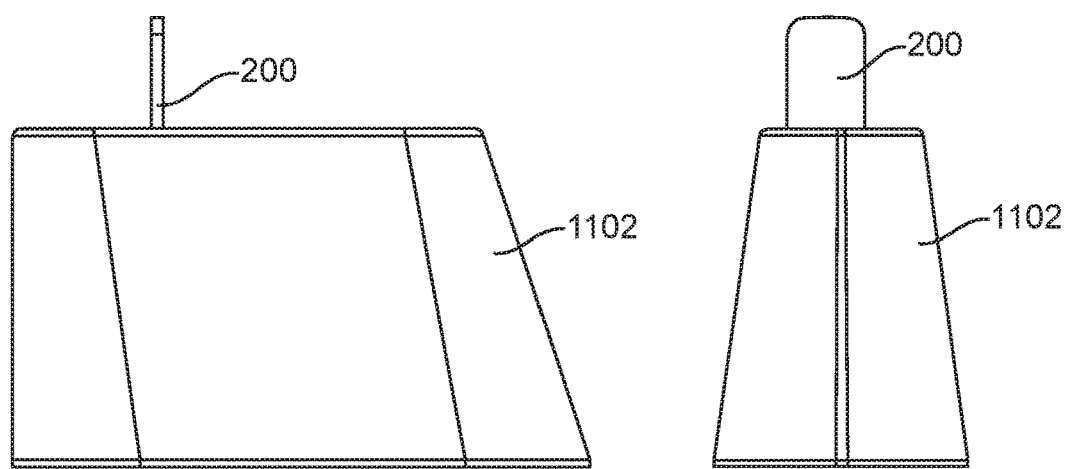
FIG. 13

PT sample all lab data
Sample CH-11 LDL

LDL Cholesterol - Direct (mg/dL)

Specimen CH-11

| Method | Labs | Mean | SD | CV | Median | Range |
|---|---|---|---|---|---|---|
| All Method | 64 | 56.4 | 12.9 | 22.9 | 55 | 30 - 83 |
| Alfa Wass. ACE HDL-C / LDL-C | 10 | 48.6 | 5.4 | 11.1 | 48 | 34 - 64 |
| Alfa Wassermann ACE Alera/Axcel Beckman AU Direct HDL / LDL | | | | | | |
| Beckman AU systems | 13 | 45.6 | 2.6 | 5.6 | 46 | 31 - 60 |
| Horiba ABX Pentra | | | | | | |
| Horiba ABX Pentra 400 | 11 | 61.0 | 3.6 | 5.9 | 61 | 42 - 80 |
| Roche LDL Direct | | | | | | |
| All Chemistry Instruments | 12 | 82.1 | 2.3 | 2.8 | 81 | 57 - 107 |
| Siemens Automated LDL | | | | | | |
| Siemens Dimension | 16 | 59.9 | 5.9 | 9.9 | 58 | 41 - 78 |

FIG. 24

CURRENT PERFORMANCE VS. CLINICAL AND MEDICAL REQUIREMENTS

| Chemistry | CLIA allowable mg/dl error | Medically allowable mg/dl error | Present mg/dl CVSEP | Present Proficiency Test mg/dl error |
|---|---|---|---|---|
| HDL | 12 mg/dl | 12 mg/dl | 10 mg/dl | 4.4 mg/dl |
| LDL | 12 mg/dl | 15 mg/dl | 16 mg/dl | 2.3 mg/dl |
| Total Cholesterol | 20 mg/dl | 29.8 mg/dl | 17 mg/dl | 2.5 mg/dl |
| Triglyceride | 40 mg/dl | 97 mg/dl | 23 mg/dl | 8.6 mg/dl |
| Glucose (glucometer) | 20 mg/dl | 21.4 mg/dl | 13 mg/dl | 4.7 mg/dl |
| Ethanol, intox | 25 mg/dl | 25 mg/dl | 9.6 mg/dl | |
| Fibrinogen | 80 mg/dl | 80 mg/dl | 48 mg/dl | |
| IgG | 3 SD | 252 mg/dl | tbd | |

FIG. 26

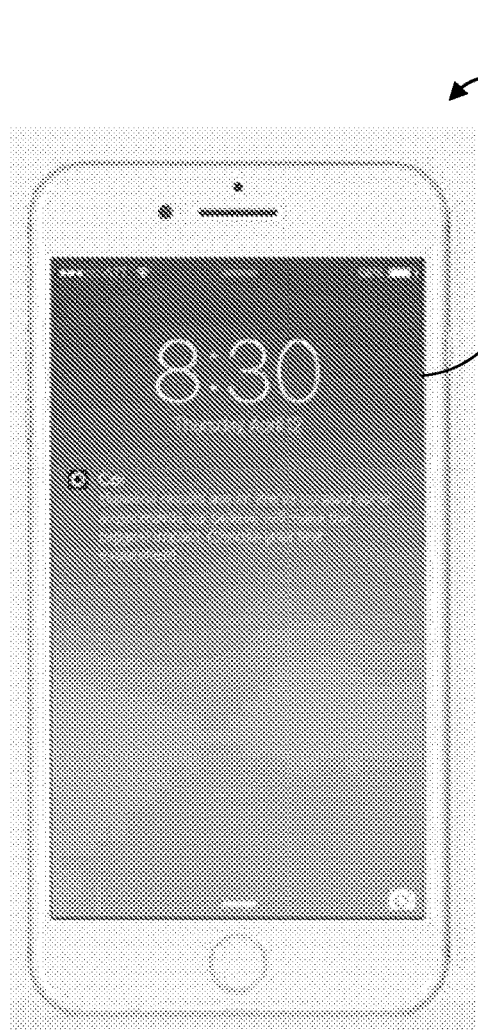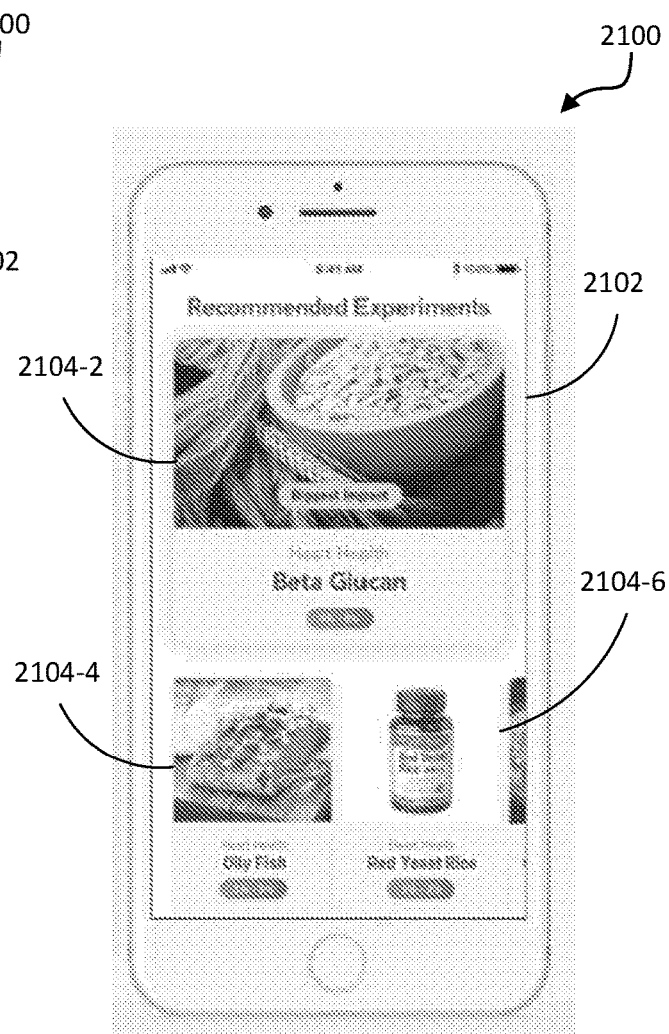
*FIG. 28*        *FIG. 29*

*FIG. 32A*  *FIG. 32B*

SYSTEMS AND METHODS FOR BLOOD ANALYSIS

RELATED APPLICATIONS

This application is a 371 national phase of PCT/US2019/030052, filed Apr. 30, 2019, and claims the benefit under 35 U.S.C. § 119(e) of U.S. Provisional Application No. 62/664,872, filed Apr. 30, 2018, entitled SYSTEMS AND METHODS FOR BLOOD ANALYSIS, the disclosures of which are incorporated, in their entirety, by this reference.

BACKGROUND

Prior approaches to health care can be less than ideal in at least some respects. Over three trillion dollars is spent annually on health care, and many of the resources spent on health care are directed to reactive treatment to preventable diseases. It would be beneficial to have improved measurements of subjects that would allow preventive measures to be taken, such as modifications in diet and lifestyle. Also, the prior paradigm of health care is based substantially around averages, yet most people are not average in at least some respects. Although some efforts have been made to personalize healthcare, the effectiveness of personalized care can be limited to the accuracy and frequency of data available for a given subject. Also, many people wish to improve their performance, appearance, or both, and such people could benefit from improved information about their wellness and physical conditioning, even though such people may not need medical care or be at risk of disease.

The prior approaches to measuring health and wellness of a subject can be less than ideal in at least some respects. Although wearable devices such as smart watches have been proposed to measure the heart rate and activity of the subject, these devices can provide somewhat limited information in at least some respects. Although laboratory based methods such as blood panels can be ordered by medical personnel, these blood tests tend to be time consuming, rely on visits to a testing facility, can be expensive, and tend to be taken less frequently than would be ideal. Also, the amount of blood drawn with the prior approaches can limit the frequency and willingness of the subject to provide blood at more frequent intervals.

Work in relation to the present disclosure suggests that it would be helpful to provide more frequent blood measurements that would allow a subject to test the effect of his or her behavior on markers of health. Also, more frequent blood measurements of people could allow the identification of new markers.

In light of the above, there is a need for improved blood testing that can be performed more frequently, with decreased amounts of blood, and with sufficient accuracy and repeatability to provide meaningful information regarding the health and wellness of the subject.

SUMMARY

The presently disclosed methods and apparatus allow frequent, reliable blood measurements with small amounts of blood, typically less than a drop of blood, such that the blood sample can be obtained in a relatively painless manner. In some embodiments the blood sample is obtained with a blood sample collector comprising a container with a volume within a range from about 0.2 microliter to about 5 microliter. The blood collector and spectrometer can be configured for whole blood reagentless spectroscopy, in which the blood sample separates within the container when the collector has been placed on the receptacle of the spectrometer. The blood collector and spectrometer can be used in many applications, such as quantitative measurements of blood chemistry and wellness applications that do not rely on quantitative measurements of blood chemistry.

The blood sample collector can be placed in a receptacle of a spectrometer to measure spectral data from the blood sample while the sample separates. The container may comprise a window to allow light such as infrared light to pass through the container, with the blood sample at least partially separating within the container between spectral measurements. The container may comprise an elongate axis extending along an elongate dimension, and the container can be configured for placement in the spectrometer receptacle with the elongate axis extending toward a vertical direction in order to improve gravimetric separation of the blood sample. A plurality of spectral measurements can be obtained at a plurality of times as the sample separates, which can provide improved accuracy of the measurements and additional information regarding the sample. The spectral data can be analyzed to determine one or more components of the blood sample. The blood sample can be placed in the spectrometer along an optical path of the spectrometer closer to a detector of the spectrometer than a light source, in order to decrease heating of the sample with the plurality of measurements of the sample while the sample separates. The blood sample can be allowed to separate for an appropriate amount of time, which can be within a range from about 5 minutes to about 3 hours, for example within a range from about 30 minutes to about 2 hours, in which a plurality of measurements is obtained during the sample separation. The plurality of measurements may comprise a plurality of successive measurements, and the sample can be allowed to separate for an amount of time between each of the successive measurements. The amount of time between successive measurements can be within a range from about 1 minute to about 10 minutes. The sample can be measured several times during the course of the gravimetric separation between a first measurement and a last measurement of the sample.

The spectrometer can be configured in many ways to measure the blood sample. In some embodiments, the blood sample is measured a plurality of times at a single location while the blood sample separates. Alternatively, the spectrometer may comprise a spatially resolved spectrometer configured to measure spatially resolved spectral data of the sample, in which a spectrum of the sample is measured at each of a plurality of locations. The spatially resolved spectrometer may comprise a wavelength selective element configured to selectively scan the sample with a light beam, such as a digital mirror coupled to a processor configured to scan a plurality of locations the sample to obtain the spectrum of the sample at a plurality of locations. The spectrometer may comprise a single detector element configured to receive light passed through the sample. Alternatively, the spectrometer may comprise a plurality of detector elements corresponding to specific locations of the sample.

In some embodiments, the methods and apparatus provide an improved user experience that motivates users to engage in lifestyle experiments to determine the effect of changes in markers related to health, which allows the user to determine which lifestyle changes are likely to improve his or her health. The experiments can be based on measurements of small amounts of blood, and changes in markers related to health. The results from these measurements can be tracked with in home spectroscopic measurements, and the change in one or more of the marker channels reported to the user.

This allows the user to determine which lifestyle activities are likely to improve health in response to changes in markers. The change in one or more markers can be output to a display to allow the user to monitor the change in the marker in response to lifestyle. By using a change in the marker channel, the approach is less sensitive to the accuracy of the measurements. The marker channel may correspond to a blood biomarker such as glucose or high density lipoprotein ("HDL"), or another marker such as blood pressure. In some embodiments, a marker channel is measured at a first time prior to conducting an experiment and a second time after starting the experiment, and a change or lack of change in the channel detected. When the experiment has been at least partially completed, the channel readout value is compared to a baseline value prior to initiation of the experiment. The user can conduct a plurality of successive experiments to improve the user's health profile.

In a first aspect, an apparatus comprises a spectrometer configured to receive a sample of blood contained within a sample holder, to illuminate the sample of blood as the blood at least partially separates within the sample holder. The apparatus also comprises a processor operatively coupled to the spectrometer, the processor configured with instructions to generate spectral data of the sample at a plurality of wavelengths and a plurality of times corresponding to at least partial separation of the sample of blood into a plurality of components of the sample.

In another aspect, a method comprises placing a sample of blood contained within a sample holder in a receptacle of a spectrometer, illuminating the sample of blood as the blood separates within the sample holder, and generating spectral data of the sample at a plurality of wavelengths and a plurality of times corresponding to at least a partial separation of the blood into a plurality of components of the sample.

In another aspect, a tangible medium is configured with instructions for: receiving a plurality spectroscopic data points from a plurality of wavelength bins; distributing the plurality of spectral data points into a plurality of marker channels. Each channel of the plurality of marker channels comprising a combination of the spectral data points from the plurality of wavelength bins. The tangible medium is also configured with instructions for: comparing a first plurality of values of the plurality of marker channels to a second plurality of corresponding values of the plurality of marker channels, the first plurality of values corresponding to a first measurement time, the second plurality of corresponding values corresponding to a second measurement time; and outputting a change in a biomarker marker channel among the plurality of marker channels to a user device.

In another aspect, a method comprises: receiving a plurality of spectroscopic data points, wherein the plurality of spectroscopic data points comprises spectrometer data of samples taken over a time interval and the spectrometer data comprises intensities from a plurality of wavelength bins; distributing the plurality of spectroscopic data points into a plurality of channels based on the plurality of wavelength bins. Each of the plurality of wavelength bins is associated with one or more of the plurality of channels and each of the plurality of channels comprises a combination of spectral measurement values from the plurality of wavelength bins. The method also comprises analyzing the plurality of channels for each channel of the plurality of channels to detect a significant change in one or more of the plurality of channels over the time interval.

In another aspect, a method comprises: presenting at least one lifestyle change experiment to a user via a graphical user interface of a user device; receiving a selection of an experiment in a computing device; prompting, from the computing device and based on the selected experiment, a reminder to the user to perform a lifestyle change in accordance with the experiment; prompting, from the computing device, the user to take a blood sample; processing, in the computing device, spectroscopic data corresponding to the blood sample; and presenting results of the selected experiment based at least on the received spectroscopic data via the graphical user interface of the user device.

In another aspect, an apparatus comprises a processor configured with instructions for: presenting at least one lifestyle change experiment to a user via a graphical user interface of a user device; receiving a selection of an experiment in a computing device; prompting, from the computing device and based on the selected experiment, a reminder to the user to perform a lifestyle change in accordance with the experiment; prompting, from the computing device, the user to take a blood sample; processing, in the computing device, spectroscopic data corresponding to the blood sample; and presenting results of the selected experiment based at least on the received spectroscopic data via the graphical user interface of the user device.

In another aspect, a system comprises a spectrometer configured to perform a spectroscopy on a user's sample of blood by receiving the user's sample of blood contained within a sample holder, illuminating the user's sample of blood as the blood at least partially separates within the sample holder; and generating spectral data from the blood as the blood at least partially separates within the sample holder. The system also comprises a network element communicatively coupled to the spectrometer and configured to process the spectral data to determine a plurality of biomarkers, wherein the network element comprises a recommendation engine configured to generate a plurality of experiments for the user based on the biomarkers.

INCORPORATION BY REFERENCE

All patents, applications, and publications referred to and identified herein are hereby incorporated by reference in their entirety, and shall be considered fully incorporated by reference even though referred to elsewhere in the application.

BRIEF DESCRIPTION OF THE DRAWINGS

A better understanding of the features, advantages and principles of the present disclosure will be obtained by reference to the following detailed description that sets forth illustrative embodiments, and the accompanying drawings of which:

FIG. 1B-2 shows a side view of the spectrometer of FIG. 1B-1;

FIG. 1B-3 shows an isometric view of the spectrometer of FIG. 1B-1;

FIG. 1F shows an exemplary step-by-step process of using the spectrometer and sample collector of FIGS. 1B-1E, in accordance with some embodiments;

FIG. 3 shows a diagram of an exemplary blood sample collector, in accordance with some embodiments;

FIG. 12 shows a perspective view of an exemplary spectrometer in another housing, in accordance with some embodiments;

FIG. 13 shows various views of the spectrometer of FIG. 12, in accordance with some embodiments;

FIG. 24 shows means and standard deviations for LDL from a blood sample measured at different labs, in accordance with some embodiments;

FIG. 26 shows the cross-validated standard errors of prediction ("CVSEP") for HDL, LDL, Total Cholesterol, Triglyceride and Glucose. in accordance with some embodiments.

FIGS. 28 to 34 show exemplary graphical user interfaces, in accordance with some embodiments;

DETAILED DESCRIPTION

The following detailed description and provides a better understanding of the features and advantages of the inventions described in the present disclosure in accordance with the embodiments disclosed herein. Although the detailed description includes many specific embodiments, these are provided by way of example only and should not be construed as limiting the scope of the inventions disclosed herein.

The presently disclosed methods and apparatus will find application in many fields. Although reference is made to testing blood, the presently disclosed methods and apparatus can be used to test many types of biomatrices. The measured biomatrix may comprise a bodily fluid, such as urine, saliva, tears (lacrimal fluid), interstitial fluid, or sweat, for example. The presently disclosed methods and apparatus can also be used to measure other materials and biomatrices, such as sebum and fecal material. Work in relation to the present disclosure suggests that fat, the microbiome, and other material present in fecal samples can be related to dietary health such as sufficiency or overload, and the methods and apparatus disclosed herein are well suited to measuring amounts of fat in a fecal biomatrix.

The presently disclosed methods and apparatus can be incorporated into prior methods and apparatus. For example, although reference is made to a scanning digital mirror, the presently disclosed methods and apparatus can be combined with other types of spectroscopy such as Fourier Transform Infrared (FTIR) spectroscopy, and dispersive spectrometers. For example, the blood collector as disclosed herein can be combined with one or more components of FTIR spectroscopy or dispersive spectroscopy, and combinations thereof. By way of example, the presently disclosed spectrometer may comprise one or more components of the commercially available DLP NIRSCAN Evaluation Module, commercially available from Texas Instruments.

Figure 1A:
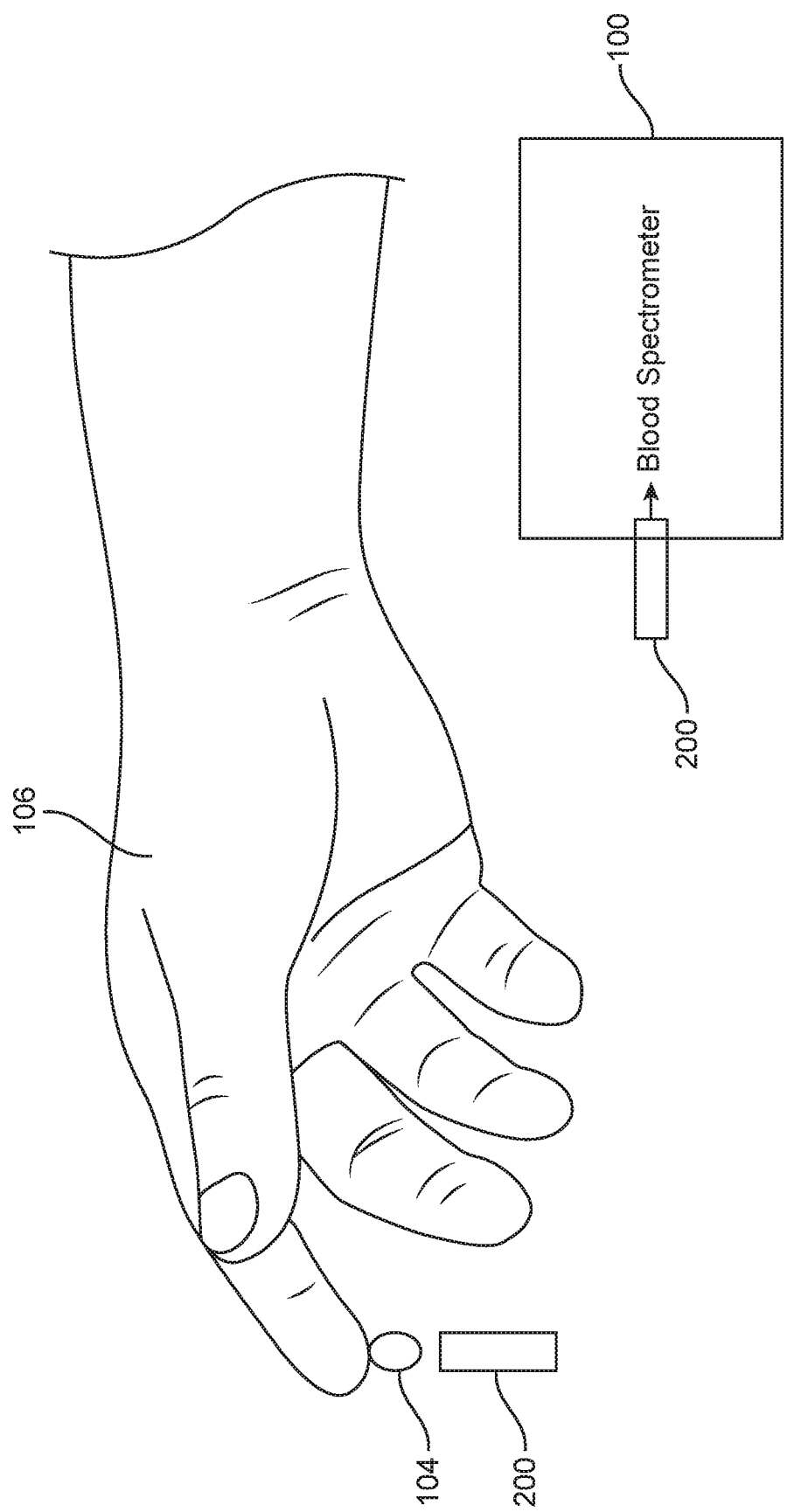
FIG. 1A shows a diagram of an exemplary blood sample and spectrometer, in accordance with some embodiments.

Turning now to FIG. 1A, a diagram of an exemplary blood sample 104 and a spectrometer 100 is shown, in accordance with some embodiments. In this embodiment, the spectrometer 100 is configured to receive the sample of blood 104 from a finger of the user 106, although the blood may be sampled from other locations, such as the forearm of the user. In some embodiments, the sample of blood 104 is typically less than a drop of blood which has a volume of about 50 microliter (μL). The sample may comprise a volume within a range from about 0.2 μL to about 5 μL, and the amount of blood can be within a narrower range from about 0.5 μL to about 2 μL, e.g. about 1 μL. The small amount of blood allows the blood sample to be taken from locations that are less painful for the subject. Once a sample of blood 104 is taken from the user 106, the sample holder 200 may be inserted into the spectrometer 100 for spectral analysis. Other bodily fluids can be as described herein sampled similarly with modification of the sampling device. Other materials as described herein can be sampled and measured by the user.

The amount of innervation of the skin can vary depending on the location, and the blood can be drawn at a location of the subject with decreased innervation. For example, the sample can be drawn from the user's forearm 106 with a sample holder, an example of such is shown and described below in FIG. 3. The sample holder may be placed in a receptacle of the spectrometer 100. The sample holder may be configured to allow the blood 105 to at least partially separate into various components. As the blood 104 separates or at least partially separates within the sample holder, the spectrometer 100 may selectively measure the various components of the blood 104, and generate a plurality of wavelength spectrum plots and/or other spectral data that correspond to the separation of the components of the blood 104. For example, the spectrometer 100 and/or some other processing system may generate spectral data of the sample at a plurality of wavelengths and a plurality of times corresponding to at least a partial separation of the sample of blood 104 into a plurality of components of the sample.

The sample blood can be combined with an anti-coagulant or blood thinner to decrease clotting when the blood sample has been placed in the sample holder. This can allow the sample to settle gravimetrically without substantial clotting. For example, the sample holder may comprise an anticoagulant prior to placing the blood in the sample holder. The anticoagulant may comprise one more commercially available anticoagulants, such as heparin. In embodiments where it is desirable to measure a clotting rate, the sample can be measured without or with reduced amounts of anticoagulant in order to allow at least partial clotting of the blood.

The at least partial separation of the blood in the sample holder may occur gravimetrically in response to the earth's gravitational field, and in some embodiments without spinning the sample in a centrifuge. The separation can be related to differences in density of components of the blood. The red blood cells, which contain iron, tend to settle toward the bottom of the sample holder, and the blood plasma, which is less dense than the red blood cells, tends to form near an upper portion of the container. In some embodiments, white blood cells settle in a region between the red blood cells and plasma. The spectrometer and processor can be configured to measure this region. The white blood cells and other cells that contain the cellular DNA, tend to settle in a region between the plasma and the settled red blood cells. This region can be referred to as the "buffy coat." Infrared spectra from this region of the tube comprising the separated blood can provide information related to DNA changes such as methylation. The spectrometer can be configured to measure at least 3 regions of the blood sample, a first region corresponding to the sample, a second region corresponding to white blood cells and a third region corresponding to red blood cells. The spectrometer can be configured to selectively scan each of these three regions with a plurality of successive measurements at appropriate times as described herein.

To illustrate, the bodily fluid as described herein such as blood may be drawn into the sample holder via a capillary action. As the bodily fluid such as blood is stored in the sample holder, the components of the bodily fluid such as blood 104 may separate into a plurality of components, for example, plasma, red blood cells, white blood cells, etc. The spectrometer 100 may illuminate each of the components by directing light to appropriate locations in the illumination window. With the gravimetric separation as described herein, the ratios of the components of blood at different locations in the sample may change, even though the blood sample may not fully separate. In response to the at least partial separation, each illuminated region of the sample may yield a different wavelength spectrum (e.g., multiple wavelengths of light with varying intensities). The spectrometer 100 may detect these various wavelength spectra (e.g., via an optical detector) and process the spectra for analysis (e.g., relative change of a biomarker, graphical display of the wavelength spectrums over time, medical advice, general healthcare advice, etc.). In this regard, the spectrometer 100 may include a processor and various forms of associated hardware, software, firmware, and combinations thereof.

The spectrometer 100 may focus light on a particular region within the illumination window of the sample holder and produce various wavelength spectra. Alternatively or in combination, a portion of the sample may be imaged onto a detector through the window of the blood collector. For example, the sample holder may separate the blood 104 into its various components. The spectrometer 100 may illuminate the blood 104 and each of its components, at a particular location within the illumination window, as the blood 104 and its components separate within the sample holder. The detector and the processor of the spectrometer 100 may then generate various wavelength spectra over time, which can be processed accordingly.

Figures 1, 1B:
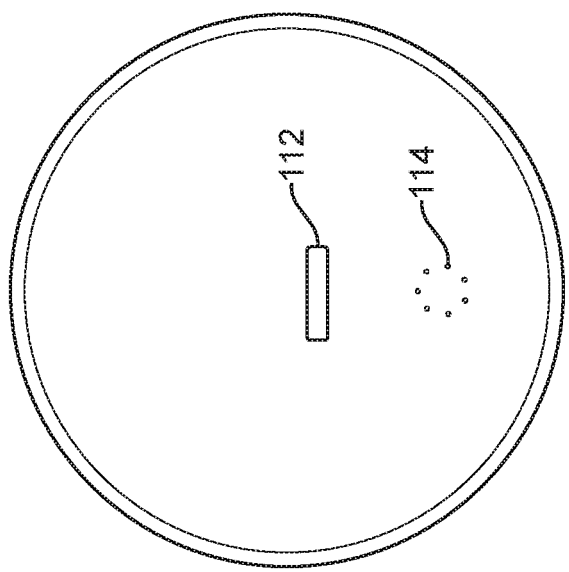
FIG. 1B-1 shows a top view of an exemplary spectrometer, in accordance with some embodiments.
Figures 1, 1B, 2:
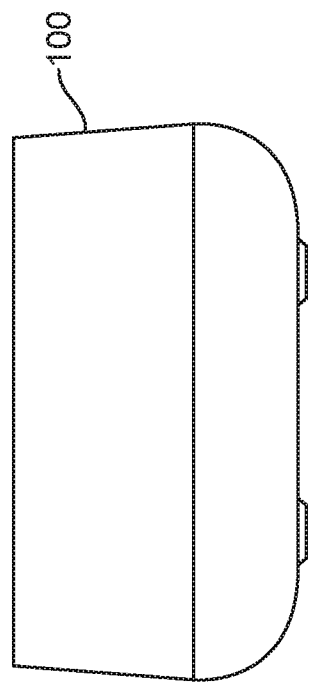

FIGS. 1B-1 to 1B-3 shows various views of the spectrometer 100. FIG. 1B-1 shows a top view of an exemplary spectrometer. FIG. 1B-2 shows a side view of the spectrometer of FIG. 1B-1. FIG. 1B-3 shows an isometric view of the spectrometer of FIG. 1B-1. In these embodiments, the spectrometer 100 is configured as a relatively small household appliance. The spectrometer 100 is configured with a sample holder slot 112 in which a user inserts a sample for spectroscopy. For example, the sample holder may be configured to hold a sample of the user's blood, sweat, tears, saliva, or other bodily fluid. Once a user sample is taken and placed in the sample holder, the sample holder may be inserted into the slot 112 for spectroscopy by the spectrometer 100. In some embodiments, the spectrometer may be configured with an audio input/output device 114 which may, among other things, provide audio instructions to the user, provide audio results to the user, receive audio queries from the user, and the like. The spectrometer may have suitable dimensions to allow the user to be portable and readily carried by the user as described herein. The spectrometer housing may comprise a substantially circular profile, such as a disk shaped profile.

Figures 1, 1B, 2, 3:
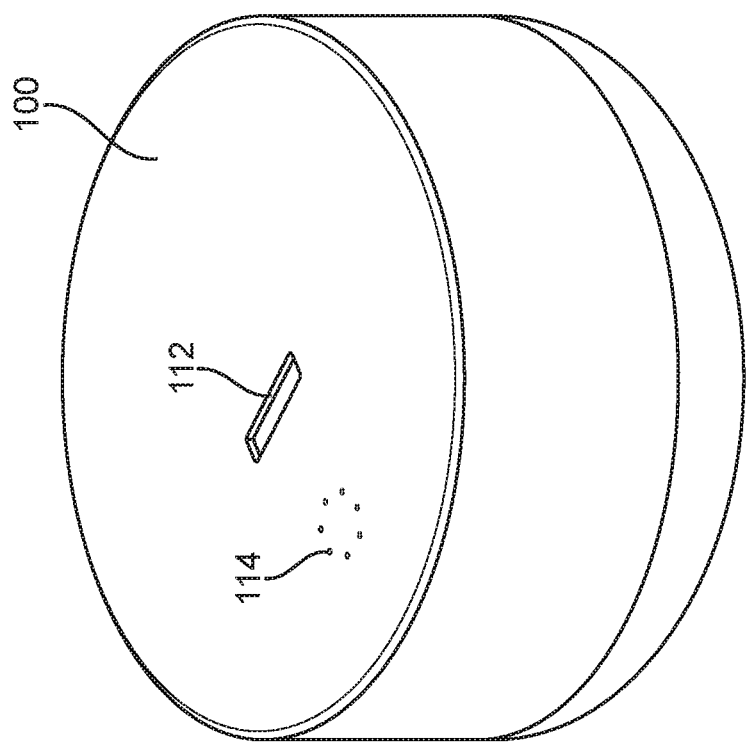
Figure 1C:
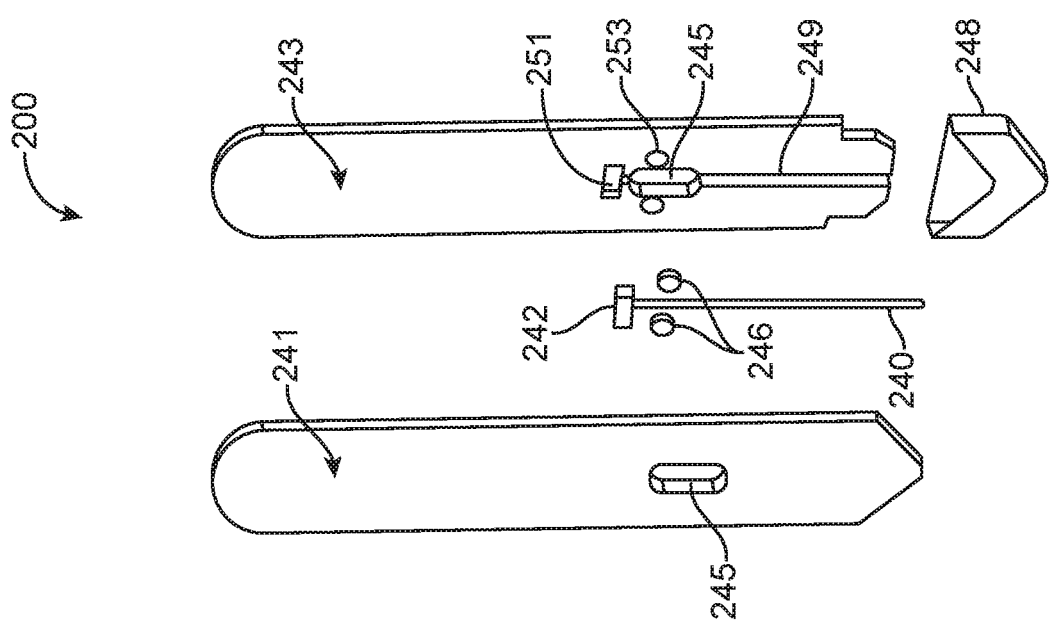
FIG. 1C shows a disassembled view of an exemplary sample holder, in accordance with some embodiments.

FIG. 1C shows a disassembled view of the sample holder 200. The sample holder 200 has a housing, which may comprise a front plate 241 and back plate 243. The sample holder comprises and an elongate container comprising a capillary tube 240 which is retained between the front plate and the back plate. The front plate and the back plate each comprise an optical port 245 to allow light from the spectrometer to be transmitted through the sample. The optical port may comprise one or more a window, an aperture, or a transparent material in the housing. A gasket 242 is located on an upper opening of the capillary tube to seal the upper opening. A retention structure such as a channel 249 is located in one or more of the front plate or the back plate to retain the capillary tube. A retention structure such as a channel 251 can be located in one or more of the front plate or the back plate to retain the gasket 247. A cap 248 can be sized to fit on the end of the sample holder 200. The cap can be sized and shaped to seal the tube receiving the sample, in order to decrease drying of the sample. The cap may comprise an indicia such as an arrow to allow for appropriate orientation of the cap, and appropriate orientation of the sample holder 200 in the spectrometer. The sample holder may optionally comprise magnets 246. One or more of the front plate or the back plate may comprise one or more retention structures such as a channel 253 to receive one or more of the magnets 246. In some embodiments, the magnets are used to couple the front plate to the back plate, to allow removal and access to the capillary tube.

A lancet needle may be separately provided to pierce the user's skin as is known in the art. The sample holder can be placed near the blood released through the skin of the user to draw the blood into the capillary tube 240.

The walls of the sample holder 200 may be constructed of any suitable material such as plastic or metal. The sample holder may comprise a single use sample holder, for example made from injection molded plastic. Although a capillary tube is shown, any elongate container can be used to hold the sample.

Figure 1D:
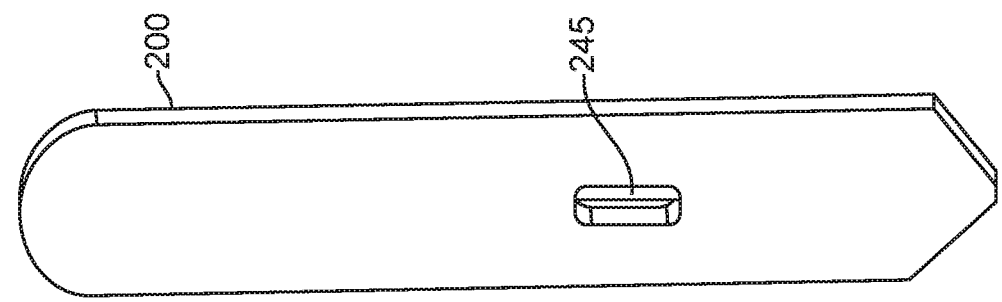
FIG. 1D shows a front view of the sample holder of FIG. 1C.

FIG. 1D shows a front view of the sample holder of FIG. 1C in an assembled configuration.

Figure 1E:
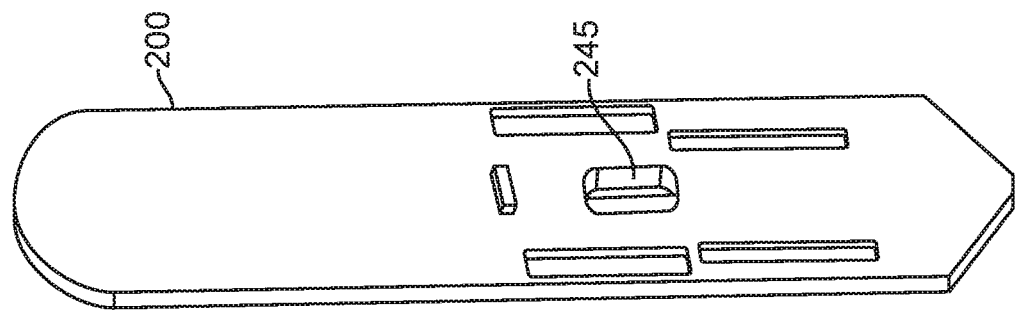
FIG. 1E shows a rear view of the sample holder of FIGS. 1C and 1D.

FIG. 1E shows a rear view of the sample holder of FIGS. 1C and 1D in an assembled configuration.

FIG. 1F shows an exemplary step-by-step process of using the sample holder 200. For example, in step 1, the user 106 obtains a sample holder 200. In steps 2 and 3, the user 106 grabs and removes the cap 248 from the sample holder 200. In step 4, the user 106 uses the capillary tube and needle therein to withdraw blood from the user's finger. Then, in step 5, the user 106 re-attaches the cap 248 to the sample holder 200. Afterwards, the user 106 inserts the sample holder 200 into the spectrometer 100 for spectroscopy as described herein.

Figure 2A:
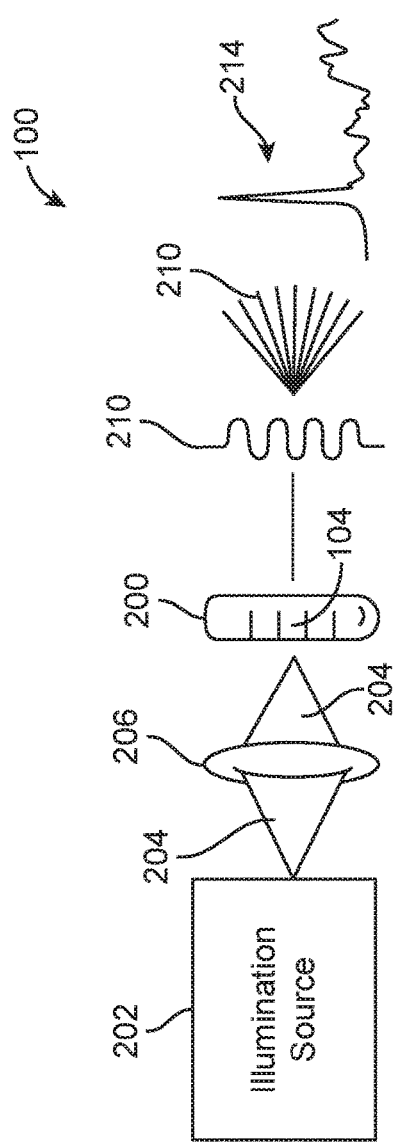
FIGS. 2A and 2B show block diagrams of an exemplary spectrometer measuring spectra of a separating blood sample, in accordance with some embodiments.
Figure 2B:
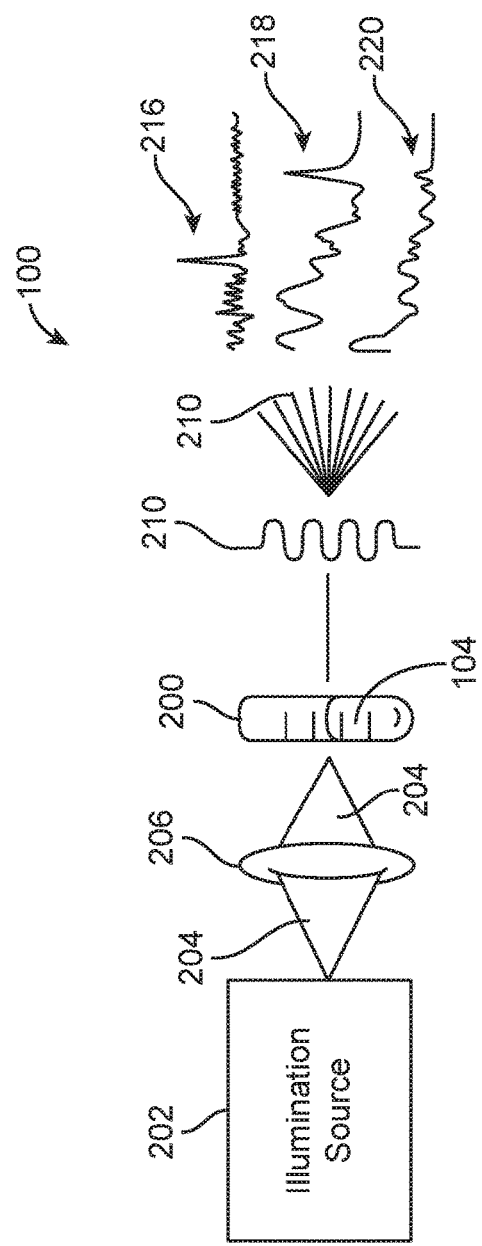

FIGS. 2A and 2B show block diagrams of the exemplary spectrometer 100 measuring spectra (e.g., spectra 214, 216, 218, and 220) of a separating blood sample 104, in accordance with some embodiments. More specifically, FIG. 2A illustrates the spectrometer 100 illuminating the sample blood 104 in a manner that may provide an initial assessment of the blood 104 over a shorter period of time (e.g., within one minute of being drawn). An illumination source 202 of the spectrometer 100 may propagate light 204 through an optical configuration 206 (e.g., various lenses, diffraction grating, mirrors, etc.). The optical configuration 206 may then selectively focus the light 204 to one or more locations of an illumination window of the sample holder 200, which, in turn, produces various wavelengths 210 of light 204. These wavelengths may be detected by an optical detector configured with the spectrometer 100 so as to produce a wavelength spectrum 214.

FIG. 2B shows a similar embodiment where blood 104 has at least partially separated into its various components within the sample holder 200 after a longer period of time (e.g. after at least about 5 minutes of being drawn from the subject). The sample such as a blood sample can be drawn into an elongate transparent structure such as a glass tube, for example. The sample holder 200 may remain in a receptacle of the spectrometer while the blood 104 separates within the holder.

A processor may direct the optical configuration 206 to focus the light 204 at various locations of the illumination window of the sample holder 200 as the blood 104 separates within the sample holder 200. For example, a first ratio of components of the blood may exist at a first location within the sample holder 200, a second ratio of components of the blood 104 may exist at a second location within the sample holder 200, and so on, as the blood separates within the sample holder 200.

The processor may direct the optical configuration 206 to focus the light 204 at the various locations to produce different wavelength spectra.

If the blood sample is left undisturbed in the sample holder for a sufficient amount of time, the blood sample may separate into layers corresponding to specific components of the blood sample. In this example, the spectrometer 100 produces an upper wavelength spectrum 216 representative of a user's plasma within the blood 104 at an upper location of the sample holder 200, a wavelength spectrum 218 representative of the user's white blood cells within the blood 104 at an intermediate location within the sample holder 200, and a wavelength spectrum 220 representative of the user's red blood cells within the blood 104 at a lower location within sample holder 200. Although the blood 104 is shown fully separated into different components, work in relation to embodiments of the present disclosure suggests that partial separation of blood is sufficient to provide useful information. Thus, the spectrometer 100 may provide a more in-depth analysis of the user's blood 104.

Again, the illumination source 202 and the optical configuration 206 may alternatively or additionally focus light 204 to a particular location on the illumination window the sample holder 200. In this embodiment, the sample holder 200 may separate the blood 104 into its various components and propagate those components through the sample holder 200 over time. Thus, the spectrometer 100 may in essence take snapshots of the blood 104 and its components over time to generate the wavelength spectra 216, 218, and 220.

One advantage of the spectrometer 100 exists in the placement of the optical configuration 206 between the illumination source 202 and the sample holder 200. For example, by placing the optical configuration 206 between the illumination source 202 and the sample holder 200, the spectrometer 100 may decrease heating of the blood 104 within the sample holder 200. That is, the spectrometer 100 may distance the sample holder from the illumination source 202 in such a way that the blood 104 within the sample holder 200 does not overheat. In some embodiments, the spectrometer is configured to heat the blood sample by no more than about 5 degrees centigrade when the sample has been placed in the spectrometer and measured for an extended period of time, e.g. for 5 minutes. This heating of no more than 5 degrees C. when placed in the spectrometer for 5 minutes while the blood separates can be helpful for whole blood reagentless measurements.

Although reference is made to scanning the measured region of the blood sample in FIG. 2B, in some embodiments, the sampled region of blood remains fixed while the blood separates. For example, the light beam can be focused to a location of the sample holder 200 such as an upper location, or collimated light passed through a window of the sample holder. The spectra can be recorded as the blood separates at least partially. In some embodiments, the measurement location comprises an upper location of the blood sample. As the blood separates the red blood cells move away from the upper portion of the column of blood, and the spectra of the upper portion becomes more consistent with spectra of the blood plasma. In some embodiments, measurements of the blood sample from a single location can provide spectral information from the whole blood of the sample and the plasma. Also, the plasma and whole blood information can be used to determine spectral properties of the lower portion of the sample related to a hematocrit of the blood sample based on changes to the spectral signal at the upper location of the blood sample, for example based on subtraction of spectral signals.

Alternatively or in combination, the measured portion of the blood sample may remain fixed at a lower portion of the blood sample below a midpoint of the blood column. As the blood separates, additional red blood cells are located at the lower portion of the blood column and the sample becomes more consistent with spectra of a hematocrit.

The blood sample can remain placed in the spectrometer for an appropriate amount of time for at least partial separation of the blood to occur, for example gravimetrically. The container may comprise a sealed container to decrease, or even inhibit, drying of the sample such as the blood sample during the gravimetric separation. The sample such as a blood sample can be allowed to separate for an appropriate amount of time, which can be as short as five minutes although the separation time may be longer. For example, the amount of time can be within a range from about 5 minutes to about 3 hours, more specifically from about 30 minutes to 2.5 hours, for example within a range from about 1 hour to about 2 hours.

The processor can be programmed with instructions for other ranges. For example, the processor can be configured with instructions to measure the sample at the plurality of times within a range from about 5 minutes to about 3 hours while the sample separates and optionally within a range from about 20 minutes to about 2 hours and optionally within a range from about 30 minutes to about 1.5 hours.

A plurality of measurements can be obtained during the time the sample is allowed to separate gravimetrically. The plurality of measurements may comprise successive measurements obtained with an interval of approximately 30 seconds to 10 minutes between measurements, for example 1 minute to 5 minutes between successive measurements.

In some embodiments the detector comprises a plurality of detectors as described herein, in which each detector corresponds to a location of the blood sample. For example, a pair of detectors can be used to measure the blood sample at a pair of fixed locations as the blood sample separates, e.g. at an upper location and a lower location of the blood sample. A grating, digital mirror, interferometer, or other wavelength selector scanned to determine the spectra of the sample at the pair of locations.

The spectrometer can be configured in many ways, and may comprise one or more components of known spectrometers, such as a Fourier Transform Infrared (FTIR) spectrometer, a dispersive spectrometer with a detector array, or a spectrometer with a tunable laser as described in U.S. application Ser. No. 14/992,945, filed on Jan. 11, 2016, entitled "Spectroscopic measurements with parallel array detector", published as US20160123869A1 on May 5, 2016, the entire disclosure of which is incorporated herein by reference. In some embodiments the spectrometer comprises a tunable laser, for example.

Figure 2C:
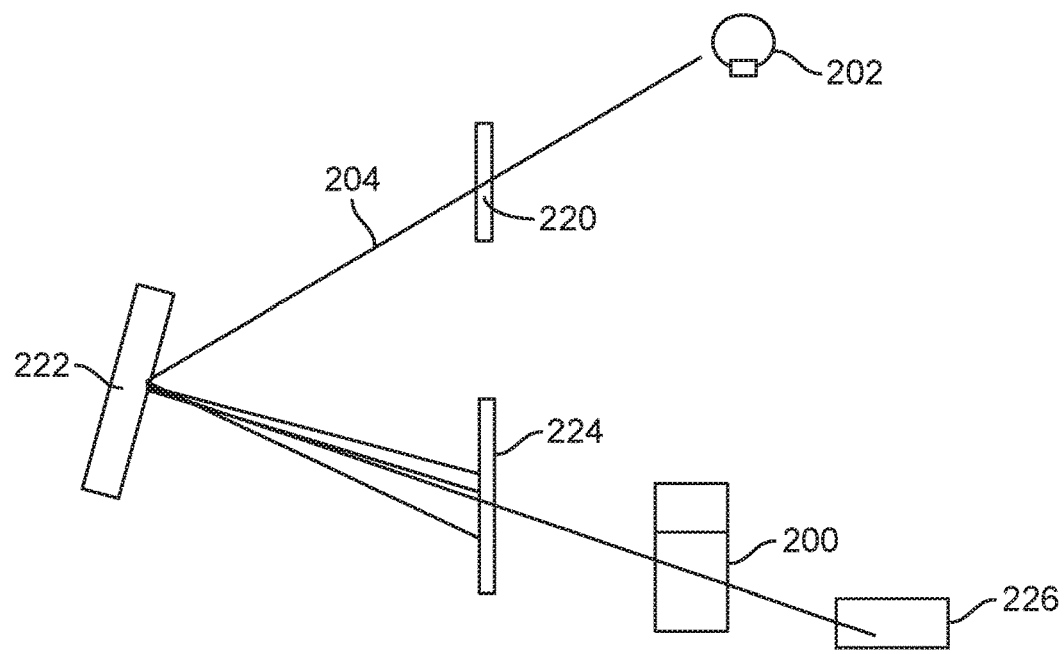
FIGS. 2C and 2D show block diagrams of the spectrometer of FIGS. 2A and 2B, in accordance with some embodiments.
Figure 2D:
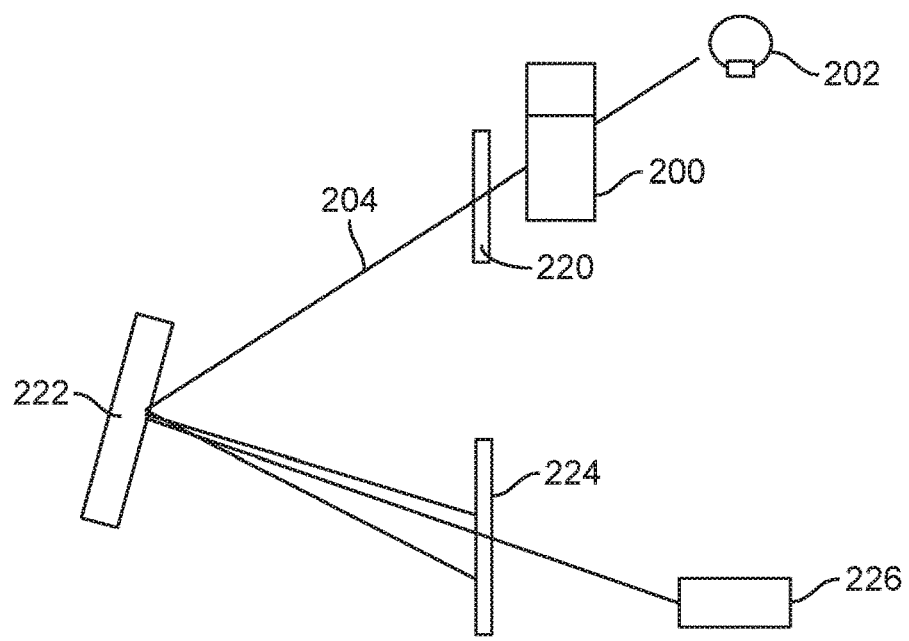
Figure 3:
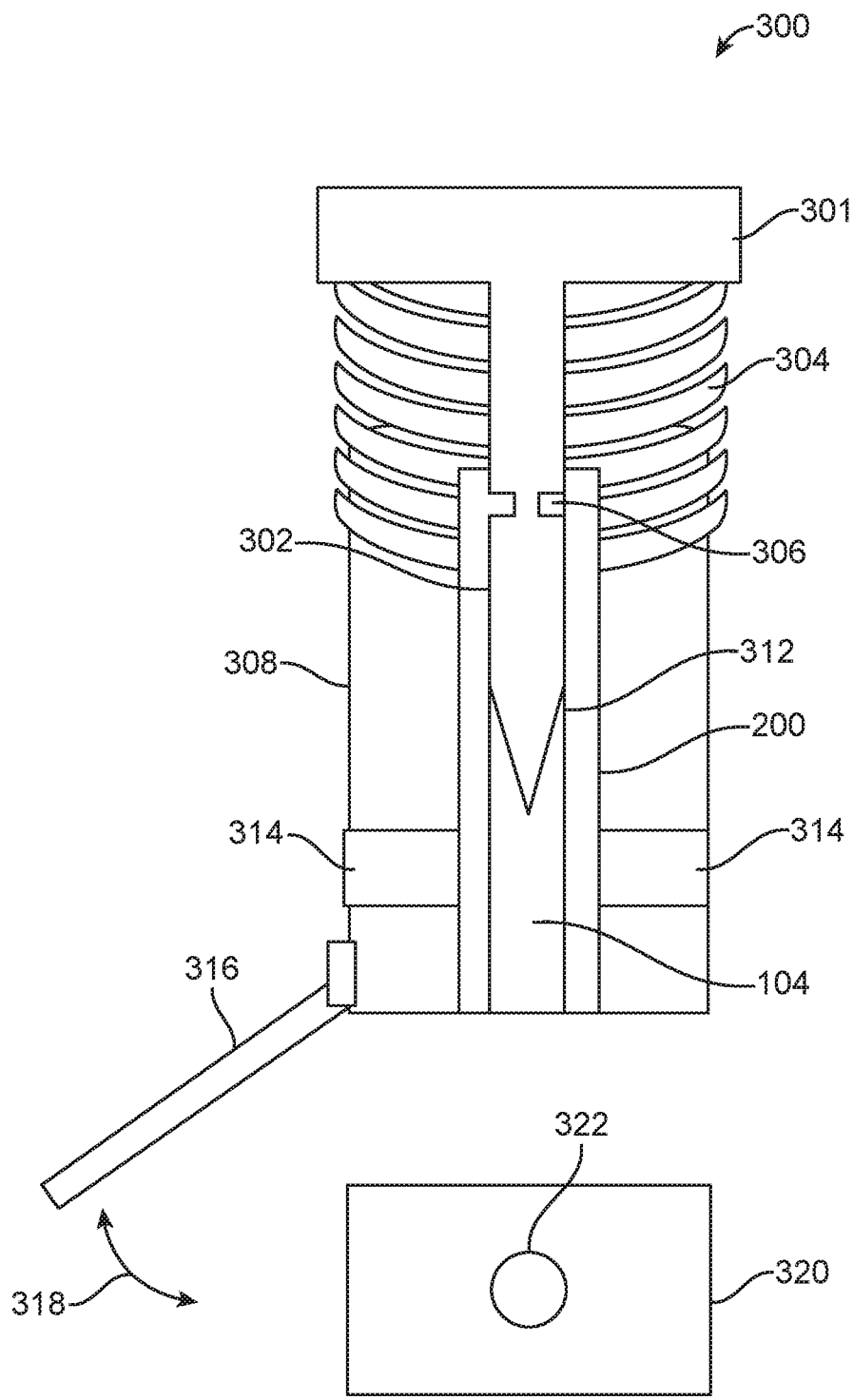

FIGS. 2C and 2D show two exemplary spectroscopy configurations of the spectrometer 100. For example, FIG. 2C shows a pre-dispersive spectroscopy configuration, in which light beam is dispersed prior to traveling through the blood sample. The sample is located along the measurement light path between the dispersive element and the detector. This configuration of the spectrometer 100 can reduce power of a beam of light 204 on the sample in the sample holder 200, thereby reducing sample heating. In these embodiments, the illumination source 202 propagates a beam of light 204 through a slit aperture 220 onto dispersive element such as a diffraction grating 222. The diffraction grating splits the beam into multiple components which are then propagated to another slit aperture 224. The beam of light 204 emanating from the slit aperture 224 propagates through the sample holder 200, and thus the sample of the user's blood, and onto a detector 226 for spectral analysis.

FIG. 2D shows a post dispersive spectroscopy configuration, in which the light beam is dispersed after traveling through the sample, and the sample holder 200 is placed between the dispersive element and the illumination source 202.

FIG. 3 shows a block diagram of an exemplary blood sample collector 300, in accordance with some embodiments. The blood sample collector 300 comprises a housing 308 to support structures of the blood collector 300. The blood sample collector 300 may comprise a lancet needle 302. The lancet needle 302 may be made from many materials, and may comprise surgical grade steel. The lancet needle 302 may be sized to extend out of an end of a tube 312 configured within the sample holder 200. The sample holder 200 may be configured within housing 308 of the blood sample collector 300. A user may thus depress the lancet needle 302 through the opening of the sample holder 200 to draw the blood 104 from the user (or another) by pushing a button 301 affixed to an end of the lancet needle 302. In this regard, the blood sample collector 300 may also include a spring mechanism 304 that allows a user to depress the lancet needle 302 into the user's skin to penetrate the user's skin. When the user releases pressure from the button 301, the spring 304 retracts the lancet needle 302 from the user's skin thereby drawing the user's blood 104 into the tube 312 of the sample holder 200 (e.g., via capillary action, suction, or the like).

In some embodiments, the tube 312 comprises a substantially transparent elongate container comprising an elongate axis to separate the sample of blood into the plurality of components. In some embodiments, the tube 312 comprises a capillary tube configured to separate the sample of blood into the plurality of components. In some embodiments, the tube 312 has a volume within a range from about 0.5 to about 2.0 microliter The amount of retraction may be limited by an O-ring groove 306 in which an O-ring may be disposed. For example, when the user releases pressure from the button 301 and the lancet needle 302 retracts, the O-ring may limit the amount of retraction to the upper portion of the sample holder 200, thereby retaining the lancet needle 302 within the blood sample collector 300.

When the blood 104 is retained within the sample holder 200 of the blood sample collector 300, the blood sample collector 300 may be closed and/or otherwise sealed with a lid 316. For example, the lid 316 may be attached to the blood sample collector 300 via a hinge mechanism that allows the blood sample collector 300 to open and close as indicated by the angular direction 318. The lid 316 may close the blood sample collector 300 via a compression fit, or other attachment mechanism. However, other embodiments may include attaching the lid 316 to the blood sample collector without a hinge (e.g., via compression fit or other attachment mechanism).

Also illustrated in this embodiment is a guide mechanism 320 that may allow the blood sample collector 300 to accurately draw the blood of the user 104 from a specified location on the user's skin. For example, the guide mechanism 320 may comprise an adhesive that sticks to the user's skin. The guide mechanism 320 may comprise an aperture 322 that is approximately the same size as the tube 312 through which the lancet needle 302 traverses. Thus, when the blood sample collector 300, and more specifically the tube 312, is placed proximate to the user's skin in the aperture 322 of the guide mechanism 320, the lancet needle 302 may penetrate the user's skin through the aperture 322.

The tube 312 may be configured of an optically transparent material, such as glass, plastic or the like. The blood sample collector 300 may be configured with optical ports 314 such that light from an illumination source, such as the illumination source 202 of FIG. 2, may pass through the blood sample collector 300 and through the blood 104 to a detector of the spectrometer 100 for subsequent wavelength spectra processing. In this regard, the sample holder 200 may also have optical ports 314 and/or be configured from an optically transparent material capable of propagating light through the blood 104 contained within the tube 312. In some embodiments, the sample holder 200 comprises a slit aperture configured to direct light through the substantially transparent tube 312. The long axis of the slit aperture may be aligned with a long axis of transparent tube 312.

In some embodiments, the sample holder 200 may be configured to provide reagentless whole blood spectroscopy. In some embodiments, a volume of the sample holder 200 is within a range from about 0.25 microliters to about 4 microliters and optionally within a range from about 0.5 to about 2 microliters. In some embodiments, a height of a window in the sample holder 200 is within a range from about 1 mm to about 20 mm and optionally within a range from about 2 mm to about 10 mm.

The sample holder 200 may be placed in the spectrometer with or without sample collector 300. In some embodiments, sample collector 300 is placed in the spectrometer with the lancet 302 within the sample holder 200 and the spectra measured. The spectrometer may comprise a receptacle sized and shaped to receive the sample collector 300. The receptacle of the spectrometer may comprise a channel sized and shaped to receive the housing 308 of the sample collector 300. Alternatively or in combination, the receptacle of the spectrometer may be sized and shaped to receive the sample holder 200 without the housing of the sample collector.

Figure 4:
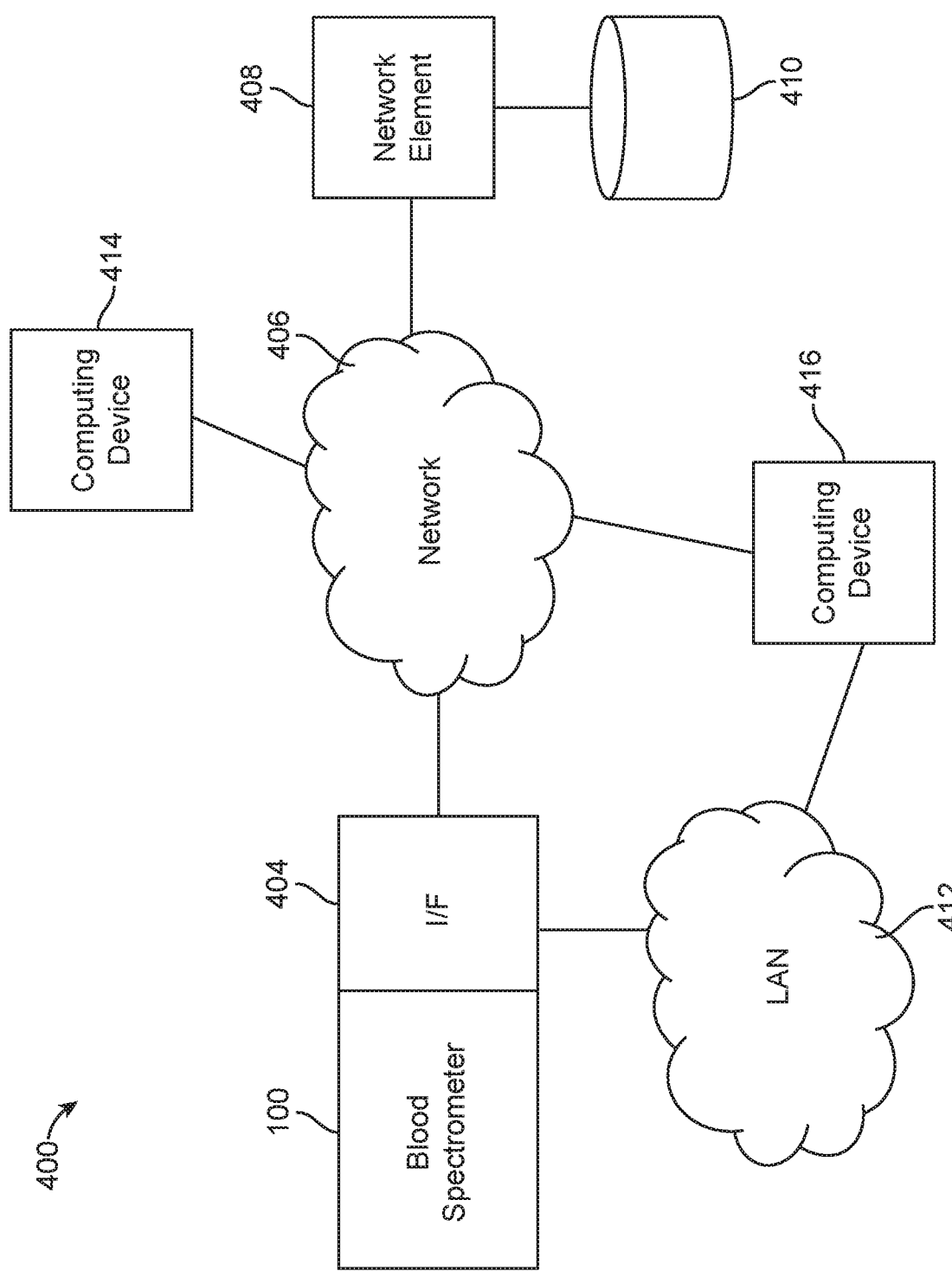
FIG. 4 shows a block diagram of an exemplary spectrometer with network connectivity, in accordance with some embodiments.

FIG. 4 shows a block diagram of an exemplary spectrometer 100 with network connectivity, in accordance with some embodiments. The spectrometer 100 may be configured with, or coupled to, a network interface 404 that is communicatively coupled to a network 406 (e.g., the Internet) and/or a local area network (LAN) 412. For example, the spectrometer 100 may be configured to receive a sample of blood contained within a sample holder, such as the sample holder 200. The spectrometer 100 may illuminate the sample of blood as the blood at least partially separates within the sample holder. And, a processor operatively coupled to the spectrometer 100 and/or configured with the spectrometer 100 may be configured with instructions to generate spectral data of the sample at a plurality of wavelengths and a plurality of times corresponding to at least partial separation of the sample of blood into a plurality of components of the sample.

When the spectrometer 100 detects the wavelength spectra of the various components of the blood 104, the spectrometer 100 may communicate the information pertaining to the wavelength spectra and/or the spectral data (e.g., spatially resolved spectral data acquired at a plurality of times) to the network 406 which may in turn communicate the wavelength spectra and/or other spectral data to a network element 408 for subsequent processing. In this regard, the network element 408 may include, or be communicatively coupled to, a database 410 which may comprise various statistics and data pertaining to blood components that can be compared to and/or analyzed against the wavelength spectra of the blood 104. Alternatively or additionally, the spectrometer 100 may include processing on board that communicates other relevant information pertaining to the blood 104 through the network 406 to the network element 408.

Also illustrated in this embodiment, is a computing device 414 that is communicatively coupled to the network 406. The computing device 414 may be used to perform such analysis on the wavelength spectra and/or other Spectral data of the blood 404 from the spectrometer 100. In this regard, the computing device 414 may be in communication with the network element 408 to retrieve information pertaining to blood analysis such that a user of the computing device 414 (e.g., a medical professional, a trainer, or the like) can analyze the wavelength spectra from the spectrometer 100 and provide a diagnosis and/or other relevant information pertaining to the user's blood 104 to a user of the spectrometer 100. Examples of the computing device 414 include computers, smart phones, and the like, comprising various hardware, software, and/or firmware components for processing the wavelength spectra from the spectrometer 100.

In some embodiments where the spectrometer 100 is communicatively coupled to the LAN 412, the spectrometer 100 may be able to communicate wavelength spectra a computing device 416. For example, the computing device 416 may also include computers, smart phones, and the like, comprising various hardware, software, and/or firmware components for processing the wavelength spectra and/or other spectral data from the spectrometer 100. In this regard, the computing device 416 may be that of the user using the spectrometer 100. For example, a user may draw his or her own blood 104 using the blood sample collector 300 of FIG. 3. The user may then input the sample of blood 104 into the spectrometer 100 to detect the various wavelength spectra of the components of the blood 104. The spectrometer 100 may then communicate the wavelength spectra to the user's computing device 416 such that the user may process the information and assess the user's own health.

The spectrometer 100, the computing devices 414 and 416, and the network element 408, either alone or in combination, may be configured with instructions (e.g., software components) that direct a processor to perform one or more analyses. For example, a processor configured with the spectrometer 100, the computing devices 414 and 416, and/or the network element 408 may measure two of more of a high density lipoprotein, a total cholesterol, a triglyceride or a glucose of the sample with a cross-validated standard errors of prediction ("CVSEP") of no more than 12 mg/dL, 20 mg/dL, 40 mg/dL, 20 mg/dL, respectively, for each of the two of more of the high density lipoprotein, the total cholesterol, the triglyceride or the glucose of the sample, with the spectral data from the plurality of times corresponding to the at least partial separation. In some embodiments, the two or more comprises three or more of the total cholesterol, the triglyceride or the glucose of the sample with the cross-validated standard errors of prediction of no more than 12 mg/dL, 20 mg/dL, 40 mg/dL, 20 mg/dL. In some embodiments, the three or more comprises four or more of the total cholesterol.

In some embodiments, the processor is configured with instructions to measure the sample at plurality of times as described herein. The processor can be configured to measure the blood sample at a plurality of times within a range from about one minute to about 3 hours (or longer) while the sample separates. The amount of time the sample is allowed to separate with measurements being obtained can be within a range from about 5 minutes to about 3 hours, more specifically from about 30 minutes to 2.5 hours, example within a range from about 1 hour to about 2 hours. The plurality of measurements may comprise successive measurements obtained with an interval of approximately 30 seconds to 10 minutes between measurements, for example 1 minute to 5 minutes between successive measurements.

The plurality of measurements obtained with gravimetric separation can be used to measure many biomarkers with improved accuracy. The gravimetric separation of blood can also be used to obtain the blood pressure of the patient, for example.

In some embodiments, the processor may measure one or more of a hormone (e.g., one or more of dehydroepiandrosterone ("DHEA"), Testosterone, Growth Hormone, Parathyroid Hormone, Estradiol, Progesterone, or Cortisol), a health and performance marker, the health and performance marker (e.g., one or more of Vitamin B12, PSA, Thyrogobulin, Troponin, IGF-1, Aldosterone, Prolactin, Creatine Kinase, Ferritin, Selenium, Homocystine, Copper, Ammonia, Folic Acid, AGE, or Cortisol), a metabolic marker (e.g., one or of Glucose, HbA1c, Glycated Albumin, Ketones, β-Hydroxybutyrate, Albumin, Total protein, BUN, Uric acid, Glutamate, GSH, Lactic Acid, CO2, pH, or Hydration), an immunology, inflammation and hematology marker (e.g., one or more of Fibrinogen, high sensitivity c-reactive protein (hsCRP), Globulins, Hematocrit, Hemoglobin, Erythrocyte sedimentation rate, Glutathione, Uric acid, Serum Amyloid A, Haptoglobin, WBC Count estimate, Transferrin saturation, Pyruvate, RBC count estimate, Platelet count estimate, Prothrombin time/INR, Interleukin-6), a cardiovascular marker (e.g., one or more of Cardiovascular total Cholesterol, HDL, LDL, Triglycerides, BNP, Apolipoprotein, or Average Blood Pressure), a marker of stress and toxins (e.g., one or more of Creatinine, Albumin, Carboxyhemoglobin, Ethanol, Carbon monoxide, Salicylates, Acetominophen, or Caffeine).

The processor can be configured with instructions to measure metabolism of the user or other subject from which the sample has been obtained. For example, the body's metabolism can describe the manner in which one's body processes the food that has been eaten. For example, a user may have a "slow" metabolism, and is therefore looking for ways to speed it up. Each person is different, and the methods and apparatus disclosed herein can help a user or other subject understand their body responds to specific foods and lifestyle changes. Specific markers of metabolism that can be measured with the methods and apparatus disclosed herein include one or more of the following: glucose, HbA1c (Glycated Hemoglobin), glycated albumin, ketones, β-hydroxybutyrate, albumin, total protein, blood urea nitrogen (BUN), uric acid, creatinine, glutamate, lactic acid (lactate), CO2 (bicarbonate), pH, sodium, magnesium, potassium, calcium, hydration, total body water (TBW), hematocrit, vitamin E, vitamin C, or vitamin A The processor can be configured with instructions to measure markers of cardiovascular health of the user or other subject from which the sample has been obtained. Cardiovascular markers are generally related to the heart and blood vessels. Circulating biomarkers related to cardiovascular health can be identified and used to adjust lifestyle accordingly. The methods and apparatus disclosed herein can be used to measure one or more of the following markers of cardiovascular health: high density lipoprotein (HDL), low density lipoprotein (LDL), total cholesterol and other cholesterol ratios, apolipoprotein, triglycerides, or average blood pressure.

The processor can be configured with instructions to measure inflammation of the user or other subject from which the sample has been obtained. Inflammation is a process by which the body protects itself from infection with foreign organisms, such as bacteria and viruses. But sometimes inflammation can become overactive and chronic, and in some instances detrimental to the health of the user. Work in relation to the present disclosure suggests that specific foods can be identified as being inflammatory. For example, sugar and other carbohydrates can be related to inflammation. The methods and apparatus as disclosed herein can be configured to allow a user to conduct an experiment related to inflammation. The processor can be configured to instructions to measure one or more markers of inflammation and immune function including but not limited to: fibrinogen, C-reactive protein (CRP), uric acid, serum amyloid a (0.6 mg/dl is normal but in chronic inflammation can be 10×), globulins, IgG, IgA, IgM (IgG is normally around 1000 mg/dl, but higher in food sensitivity and in multiple myeloma, and lower in immune deficiencies), or haptoglobin.

The processor can be configured with instructions to measure hematology of the user or other subject from which the sample has been obtained. Hematology is a measurement of the properties of blood. The hematology measurements can be indicative of dietary deficiencies. The processor can be configured to instructions to measure one or more markers of hematologic function including but not limited to: hematocrit, hemoglobin, erythrocyte sedimentation rate (ESR), transferrin saturation (iron deficiency), pyruvate, red blood cell ("RBC") count, white blood cell ("WBC") count, platelet count, or prothrombin time (also referred to as INR as a measure of time for blood to clot).

The processor can be configured with instructions to measure markers of toxins of the blood sample from the user. The toxins may comprise external factors that can negatively effect health. The toxins may comprise environmental pollutants, specific drugs, exposure to cigarette smoke, use of alcohol. The processor can be configured to instructions to measure one or more markers of toxins including but not limited to: carbon monoxide, carboxyhemoglobin (second hand smoke), ethanol, salicylates, acetominophen, ethylene glycol, or caffeine.

The processor can be configured with instructions to measure markers of stress from the blood sample from the user. Stress can be reflected in blood markers and it can be helpful to decrease stress to keep healthy. Insufficient sleep can be a contributing factor for stress. The processor can be configured to instructions to measure one or more markers of stress including but not limited to: dehydroepiandrosterone (DHEA), dehydroepiandrosterone-S(DHEA-S), creatinine, glucose, C-reactive protein (CRP), fibrinogen, HbA1c, albumin, or ethanol.

In some embodiments, the processor is configured with instructions to measure fecal fat channel. The fecal fat channel may comprise a channel measuring fecal fat of the user, for example with a spectrometer as disclosed herein.

The processor can be configured with instructions for a user to conduct an experiment with a plurality of blood samples from the user (or another subject). For example, the processor can be configured for the user to select one or more experiments as described herein, such as one or more of a metabolism experiment, a cardiovascular health experiment, an inflammation and immune function experiment, hematologic function experiment, a toxin experiment, a stress experiment, a saliva experiment, or a fecal fat experiment.

In response to the user selecting the experiment, the processor provides appropriate prompts for the user to conduct the experiment. The processor may comprise instructions to present an appropriate instruction to the user to conduct the experiment. For each type of experiment the processor can be configured with instructions to measure one or more of the markers as described herein. The following examples of experiments list markers that can be measured for each experiment in accordance with some embodiments.

For the cardiovascular experiment, the processor can be configured with instructions to detect a change or lack of change in one or more of the following channels: Total Cholesterol (TC), HDL, LDL, Triglycerides, very low density lipoprotein (VLDL), non-HDL, lipid ratio, B-type natriuretic peptide (BNP), apolipoprotein, or average blood pressure For the inflammation experiment, the processor can be configured with instructions to detect a change or lack of change in one or more of the following channels: fibrinogen, ESR, hsCRP, or Globulins.

For the metabolism experiment, the processor can be configured with instructions to detect a change or lack of change in one or more of the following channels: glucose, fructosamine, hemoglobin A1c, ketones, hemoglobin, hematocrit, insulin resistance, total protein, or albumin.

For the stress experiment, the processor can be configured with instructions to detect a change or lack of change in one or more of the following channels: oxidized LDL (oxLDL), glutathione peroxidase, carboxyhemoblobin, carbon monoxide, creatinine, albumin, or ethanol.

For the toxin experiment the processor can be configured with instructions to detect a detect a change or lack of change in in one or more of the following channels: dehydroepiandrosterone (DHEA), dehydroepiandrosterone-S (DHEA-S), creatinine, glucose, C-reactive protein (CRP), fibrinogen, HbA1c, albumin, or ethanol.

For the saliva experiment and the processor can be configured with instructions to detect a change or lack of change in one or more of the cortisol channel, or another biomarker channel as disclosed herein present in saliva.

For the fecal fat experiment the processor can be configured with instructions to detect a change or lack of change in the fecal fat channel, or another biomarker channel as disclosed herein present in fecal material.

Additional experiments can be conducted to measure one or more channels as described herein.

The processor can be configured with instructions to prompt the user for fasting tests such as triglyceride and glucose, for example.

The processor can be configured with instructions to prompt the user for post-prandial test, such as triglyceride (2-4 hour post-prandial, TGpp), and glucose (1-1.5 hour post-prandial), for example.

The processor can be configured with instruction to measure total protein channels and albumin channels, and globulins calculated from total protein and albumin ratios (TP-ALB).

The processor can be configured with instructions for the user to conduct an experiment for an appropriate amount of time, such as 1 week to 8 week, for example 2 to 4 weeks, and in some embodiments 3 weeks.

The experiment may comprise a measurement to determine lowering triglycerides by eating walnuts, lowering LDL by eating beta glucan, red yeast, for example. Similar lifestyle changes can be measured to determine increases or decreases in the channel corresponding to LDL, or ketones, for example.

The experiment may comprise measuring lower fasting glucose, fructosamine and HbA1c with an appropriate lifestyle change such as walking or addition chromium to the user's diet.

The processor can be configured with similar lifestyle changes to evaluate improvements in one or more inflammation channels as described herein.

The processor can be configured with instructions to allow the user to select a fecal fat experiment, and evaluate changes in fecal fat in response to a lifestyle change as described herein.

In some embodiments, the spectrometer 100 comprises a broad spectrum light source to generate a plurality of wavelengths of light, a detector, and a wavelength selector coupled to the broad spectrum light source to selectively direct light toward the detector with the sample located between the wavelength selector and the detector. The wavelength selector may comprise one or more of a dispersive element, a prism, a grating, a digital mirror device ("DMD"), a diffractive optic, an interferometer, a Michelson interferometer, or an Etalon. In some embodiments, the spectrometer 100 comprises a digital micromechanical mirror optically coupled to the wavelength selector to selectively reflect the light from the wavelength selection to the detector.

In some embodiments, the detector comprises an indium gallium arsenide (InGaAs) detector. In some embodiments, the detector comprises a single element detector, while in other embodiments the detector comprises a plurality of detector elements. In some embodiments, the processor may take substantially continuous scans of blood sample with a duty cycle within a range from about 10% to about 90% of a light source illuminating a detector of the spectrometer. In some embodiments, the spectrometer 100 comprises a receptacle to receive the sample holder (e.g., the sample holder 200 and/or the blood sample collector 300 illustrated in FIGS. 2 and 3) with the blood contained therein with an elongate axis of the sample holder oriented toward a vertical angle of inclination to separate the blood. In some embodiments, a number of spatially resolved sample locations along a height of the sample is within a range from about 2 to about 1000 and optionally within a range from about 5 to about 100.

In some embodiments, the plurality of wavelengths corresponds to a plurality of discretely resolved wavelength bands within a range from about 25 to about 1000 discretely resolved wavelength bands and the plurality of successive measurements is within a range from about 2 to about 1000 successive measurements. In some embodiments, the plurality of discretely resolved wavelength bands is within a range from about 50 to about 200 and the plurality of successive measurements is within a range from about 5 to about 200 successive measurements.

In some embodiments, the plurality of discretely resolved wavelength bands comprises a plurality of wavelength bands within a range from about 1350 nm to about 2500 nm. The range can be from about 1600 nm to 2400 nm.

In some embodiments, the spectrometer comprises a maximum dimension of 170 mm and optionally wherein the spectrometer comprises a length of no more that about 170 mm, a width of no more than about 75 mm, and a height of no more than about 100 mm and optionally wherein the spectrometer comprises a length within a range from about 80 to about 170 mm, a width within a range from about 30 to about 75 mm and a height within a range from about 50 to about 100 mm and optionally wherein the spectrometer comprises a volume within a range from about 120,000 mm3 (0.12 liter) to about 1,275,000 mm3 (1.275 liter). Based on the teachings provided herein, a person of ordinary skill in the art can decrease the dimensions with optics of decreased sizes and focal lengths, for example.

In some embodiments, the sample holder comprises an elongate channel. In this regard, the spectrometer 100 spectrometer may be configured to receive the sample holder and align the elongate channel of the sample holder 200 along a substantially vertical direction to separate the blood into the plurality of components along the elongate channel. The substantially vertical direction may comprise an angle within about 20 degrees of vertical. In this regard, a DMD of the spectrometer 100 and the processor may be configured to selectively scan a first region of the sample holder comprising a first component (e.g., blood plasma), and to selectively scan a second region of the sample holder comprising a second component (e.g., hematocrit). In some embodiments, the processor may be configured with instructions to determine an amount of time for the sample to separate into the first and second components.

In some embodiments, the processor directs substantially continuous scans of the sample with a duty cycle within a range from about 10% to about 90% of a light source illuminating a detector of the spectrometer.

Figure 5:
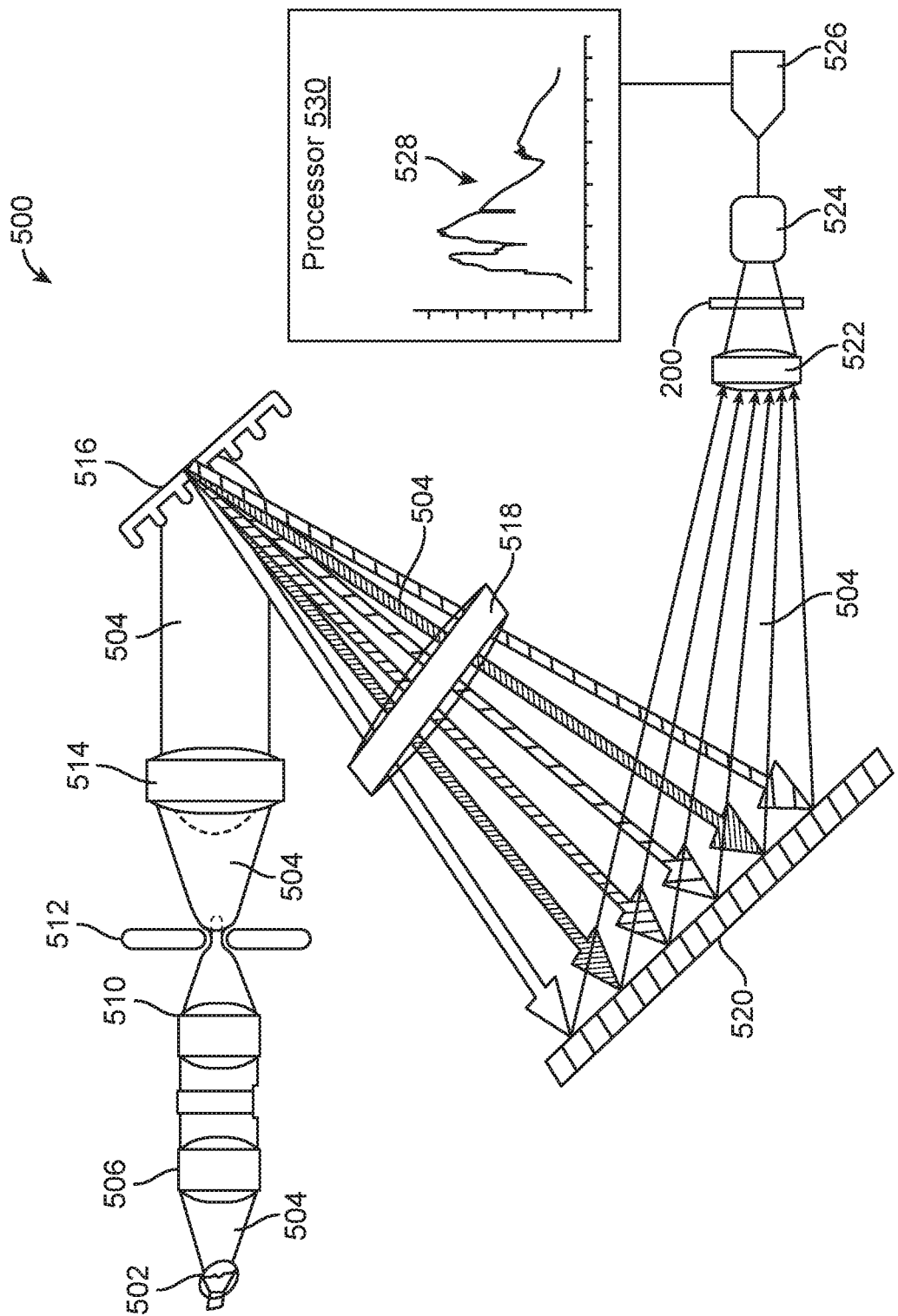
FIG. 5 shows a block diagram of an exemplary optical configuration of a spectrometer, in accordance with some embodiments.

FIG. 5 shows a block diagram of an exemplary optical configuration 500 of a spectrometer, such as the spectrometer 100 of FIG. 1, in accordance with some embodiments. In this embodiment, the optical configuration 500 includes an illumination source 502 that may be configured to illuminate a sample of blood 104 in the sample holder 200 with light 504. In some embodiments, the illumination source is configured to propagate broadband light through the optical configuration 500, however more specific wavelengths of light may be chosen.

The optical configuration 500 may propagate the light 504 through coupling optics 506 and 510. For example, the coupling optic 506 may collimate the light 504 from the illumination source 502 to the coupling optic 510. The coupling optic 510 may propagate the light 504 through an aperture 512 (e.g., a slit aperture) which may, in turn, the focus the light 504 onto a collimating optical element 514. The collimating optical element 514 may collimate the light 504 onto a diffraction grating 516. The diffraction grating 516 may split and diffract the light 504 into a plurality of rays travelling in different directions as indicated by the rays of the light 504.

The optical configuration 500 may also include a focusing optical element 518 that is operable to propagate the diffracted rays of light 504 onto digital micromirror device (DMD) 520 that may be operable to selectively pixelate the diffracted light 504 from the diffraction grating 516. In this regard, a processor 530 may be communicatively coupled to the DMD 520 to selectively control individual mirrors of the DMD device 520. The DMD 520 may propagate the pixelated light 504 to a focusing optical element 522 which may, in turn, focus the pixelated light 504 through the sample holder 200 and thus through the sample of blood 104. In some embodiments, the sample holder 200 may be positioned at or near a focal length of the focusing optical element 522.

The focused light 504 from the focusing optical element 522 may propagate through the sample of blood 104 within the sample holder 200 and to the detector 524. In some embodiments, the detector 524 may comprise an indium gallium arsenide (InGaAs) detector (e.g., a single element or single point InGaAs detector). The detector 524 may convert the optical energy of the light 504 into an electronic signal which may be digitized by an analogue to digital converter (ADC) 526 for subsequent processing by the processor 530. For example, the processor 530 may process the digitized electronic signal from the ADC 526 to generate the wavelength spectrum 528 of the blood 104 within the sample holder 200.

As mentioned, the spectrometer 100 may be configured to selectively measure separated or at least partially separated components of the blood 104 within the sample holder 200. In this regard, the processor 530 may activate certain mirrors of the DMD 520 to illuminate certain locations within the sample holder 200. For example, the processor 530 may direct one or more mirrors of the DMD 520 to illuminate a first location on the sample holder 200 where a first component of the sample of blood 104 is located. The processor 530 may then direct one or more mirrors the DMD 520 to illuminate a second location of the sample holder 200 where a second component of the sample of blood 104 located. Thus, the processor 530 may direct the DMD 520 to activate certain portions of the DMD 520 to illuminate locations of the sample holder 200 depending on the number of separated components of the blood 104 and/or depending on the components of the blood 104 desired for analysis.

The sample holder 200 is located along the optical path between light source 502 and detector 524 in order to measure the spectra of the sample. The spectrometer 500 may comprise a receptacle to receive one or more of the sample holder 200 or sample collector 300 at a location along the optical path as described herein. In some embodiments, the sample holder 200 is positioned between the focusing optical element 522 and an optical detector 524. In doing so, the optical configuration 500 may decrease heating of the sample of blood 104 in the sample holder 200. In other embodiments, the sample holder 200 may be positioned between coupling optics 506 and 510. For example, the coupling optic 506 may collimate the light 504 from the illumination source 502 through the sample holder 200 to the coupling optic 510. In this configuration, the coupling optic 506 may also operate as a sort of heatshield to prevent the sample of blood 104 in the sample holder 200 from overheating.

Examples of the optical elements shown or described herein (e.g., the optical elements 506, 510, 514, 518, and 522) may include focusing lenses, collimating lenses, condenser lenses, optical filters, combinations thereof, and the like.

In some embodiments, the sample of blood is located between the DMD 520 and the detector 524. For example, the sample of blood may be located within about 10 mm of the detector 524. In some embodiments, the processor 530 may be configured to select a region of the sample of blood, and to direct light from the region to the detector 524. For example, the sample holder 200 may be configured to orient the sample of blood along a column, and to separate the blood along the column. The DMD 520 and the processor 530 may be configured to selectively scan light from a plurality of regions of the sample of blood to the detector 524.

The focusing element optical element 522 may comprise collections optics placed at an appropriate distance from the detector as described herein. The detector may be placed near a focal length of the collection optics, e.g. element 522. A surface the detector can be is located within +/−25% of the focal length of the collection optics, for example. Alternatively or in combination, the sample can be placed within +/−25% of the focal length of the lens element 522.

In some embodiments, the optical components are configured in accordance with the principles of Fourier optics. For example, grating 516 may be located near a focal length of focusing optical element 518, e.g. within 25% of the focal length of the lens, such that the lens provides a far field diffraction pattern of the grating 516 on the DMD 520. The focusing element 522 can be located approximately a focal length from the sample holder 200 and/or detector 524, which results in the Fourier transform of the DMD being projected onto the sample holder and/or detector 524. As will be appreciated by one of ordinary skill in the art, a Hadamard transform comprises an example of a general class of Fourier transforms. In this regard, the DMD can be programmed with a Hadamard transform function, so as to focus the beam onto the sample at a specific location. The processor can be programmed to scan the sample with a plurality of successive Hadamard transforms, in which each of the plurality of Hadamard transforms corresponds to a specific location of the sample. The DMD can be programmed with a plurality of Hadamard transform encodements, in which each of the plurality of encodements corresponds to a Hadamard transform to measure the sample at an appropriate location as described herein. By sequentially configuring the DMD with each of the plurality of Hadamard transforms, successive locations of the sample can be scanned. The Hadamard transforms may comprise two dimensional Hadamard transforms. Although reference is made to a Hadamard transform, other Fourier transforms may be used to configure the DMD for scanning.

Although reference is made to scanning successive non-overlapping locations of the sample with the DMD, other approaches may be used. For example, the spectrometer may comprise a movable mirror coupled to an actuator such as a galvanometer in order to scan the measurement beam to specific locations of the sample. The galvanometer can be used in combination with the DMD, for example, in which movement of the mirror with the galvanometer scans the beam in a substantially vertical direction along the blood sample in the sample holder. Alternatively or in combination, the DMD may be mounted on an actuator configured to change an angle of inclination of the DMD in order to scan the sample with the beam.

Figure 6:
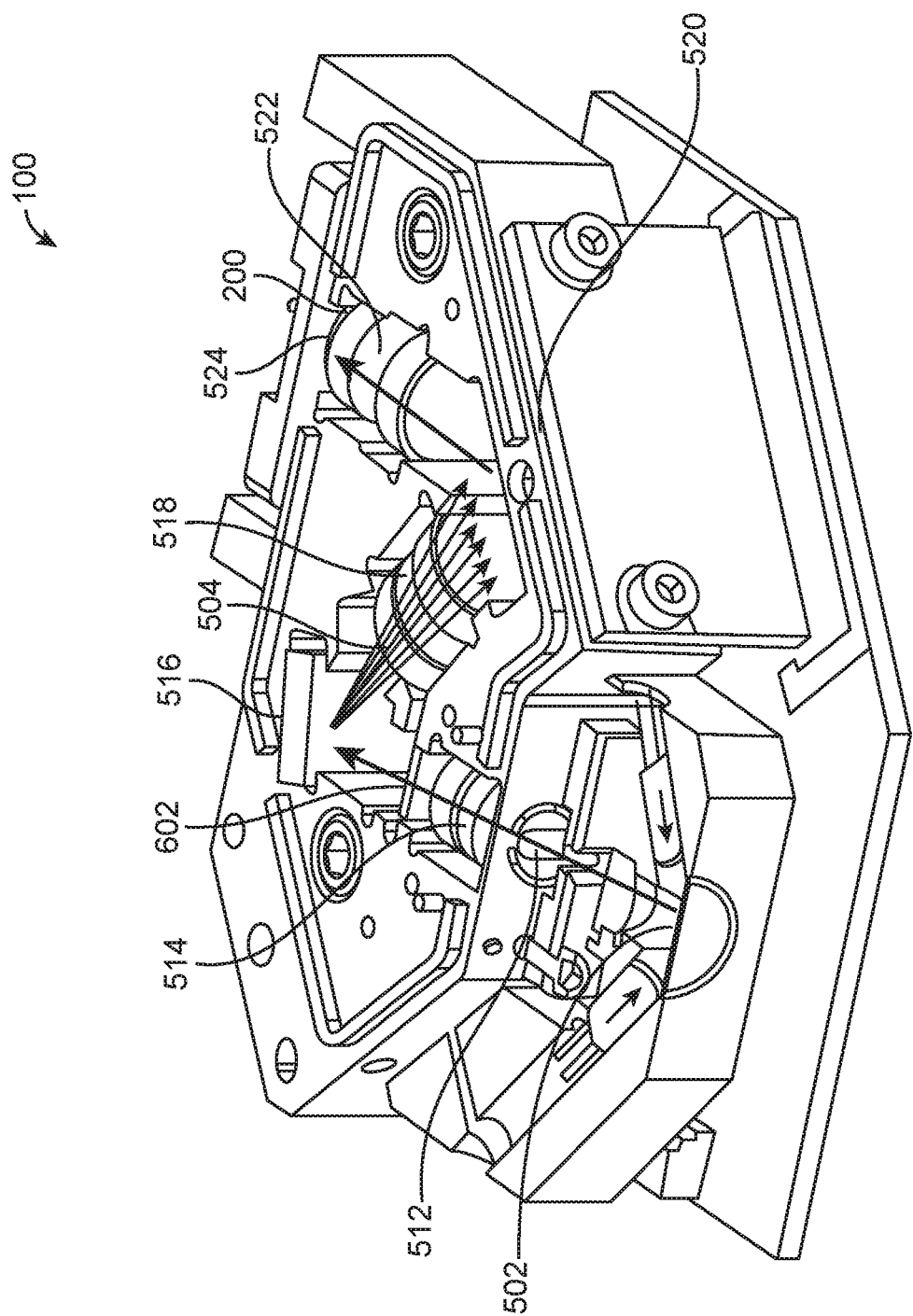
FIG. 6 shows a perspective view of an exemplary spectrometer, in accordance with some embodiments.

FIG. 6 shows a perspective view of an exemplary spectrometer 100, in accordance with some embodiments. A physical layout of the optical components configured with the spectrometer 100 is shown. As with the optical configuration 500 of FIG. 5, the spectrometer 100 comprises an illumination source 502 that is configured to propagate the light 504 through the sample holder 200 to a detector 524. The sample holder may be placed between the detector 524 and a lens that focuses light on to the lens. Alternatively, the sample holder 200 can be placed near the long pass filter 602, e.g. between the long pass filter and a collimation lens.

In this embodiment, the illumination source 502 propagates the light 504 through a slit aperture 512 to the optical element 514 (e.g., a collimating lens). The spectrometer 100 may include a long pass filter 602 that is operable to filter off shorter wavelength components of the light 504 from the illumination source 502. Thus, the long pass filter 602 may propagate the longer wavelengths of the light 504 and, in this embodiment, to a diffraction grating 516. The diffraction grating 516 may diffract the light 504 through the focusing lens 518 onto the DMD 520. The DMD 520 may then, depending on the selected pixels/mirrors, propagate the pixelated light 504 through the focusing optical element 522 (e.g., a condenser lens), and ultimately through the sample holder 200 to the detector 524.

Although shown and described with respect to a particular optical configuration, the spectrometer 100 may be configured with other optical configurations. For example, the spectrometer 100 may employ a compact optical figuration so as to reduce the overall size of the spectrometer 100 for personal use by a user. Some exemplary optical configurations that may be configured with the spectrometer 100 are now shown and described with respect to FIGS. 7-9.

Figure 7:
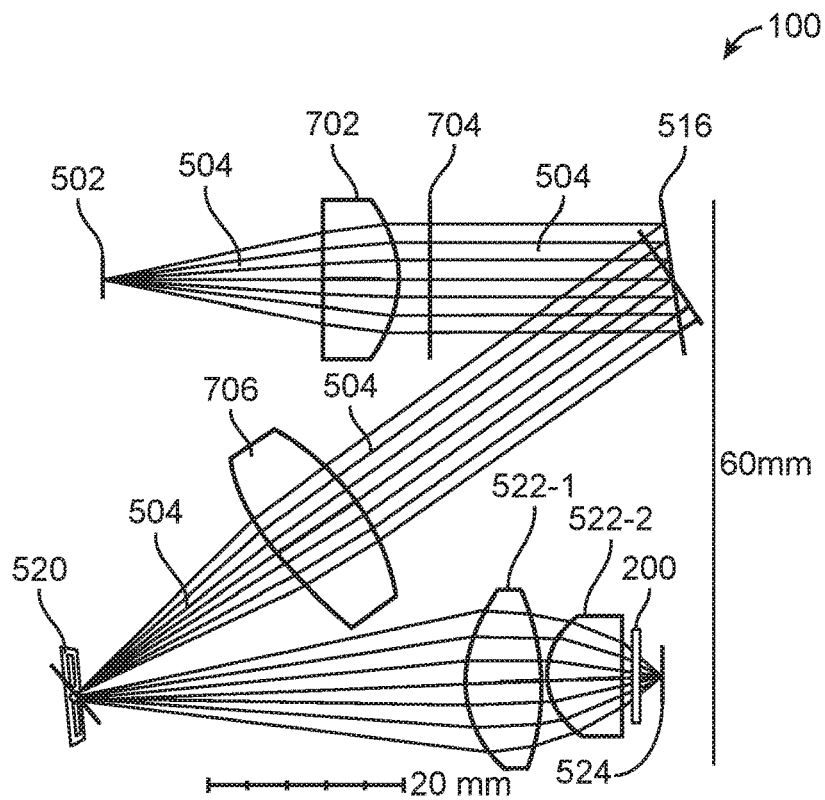
FIG. 7 shows an optical schematic of a spectrometer comprising an optical configuration, in accordance with some embodiments.

FIG. 7 shows an optical schematic of a spectrometer 100 comprising various optical elements in one exemplary optical configuration, in accordance with some embodiments. As with the embodiments above, the spectrometer 700 comprises an illumination source 502 operable to propagate light 504 through an optical configuration through a sample holder 200 to a detector 524. In this embodiment, the light 504 propagates from the illumination source 502 through a collimating lens 702. The collimating lens 702 may propagate the light through a long pass filter 704 to filter off shorter wavelengths of the light 704. The sample holder 200 can be placed near the detector 524 or near the collimation lens 702.

Figure 8:
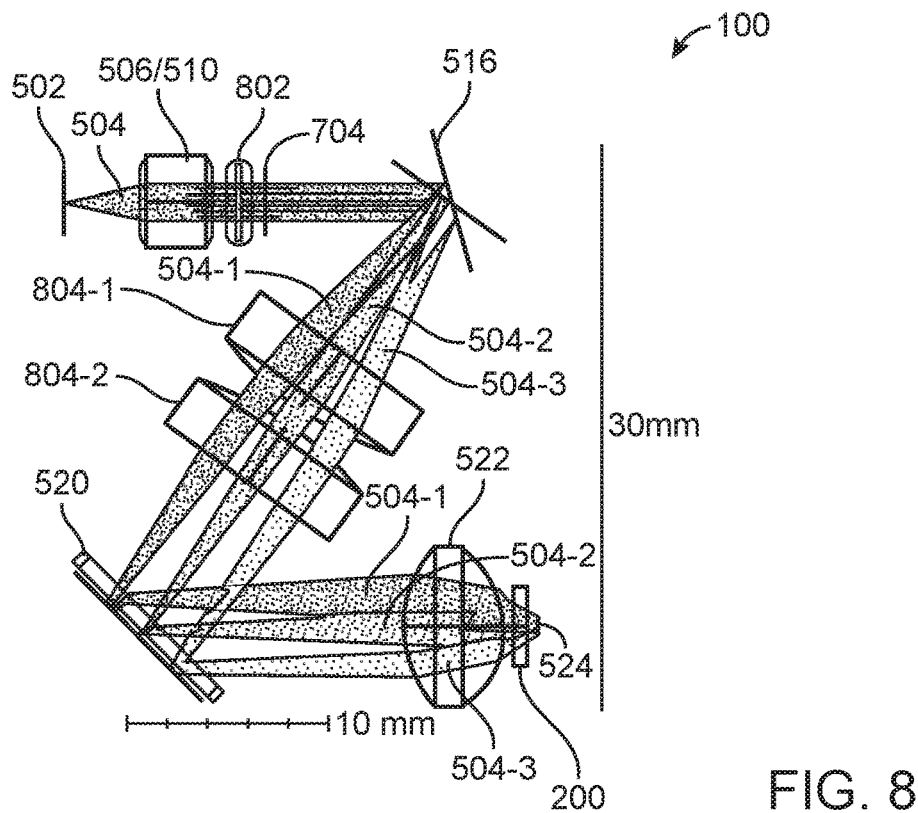
FIG. 8 shows an optical schematic of a spectrometer comprising another optical configuration, in accordance with some embodiments.

The filtered light 504 may propagate to a diffraction grating 516 that diffracts the collimated/filtered light 504 to a focusing lens 706. The focusing lens 706 may focus the light onto the DMD 520 which may selectively propagate/pixelate the light 504 to a focusing optical configuration comprising focusing lenses 522-1 and 522-1. For example, as the optical configuration of this embodiment is known (e.g., known focal lengths, known distances between optical elements, etc.), a processor may be configured to select which mirrors of the DMD 520 are to be activated to measure the various locations of the sample holder 200 and the components of the blood 104 therein FIG. 8 shows an optical schematic of a spectrometer 100 comprising various optical elements in another exemplary optical configuration, in accordance with some embodiments. In this embodiment, the illumination source 502 propagates the light through the coupling optical elements 506/510 which may couple the light 504 to a collimating lens 802. The collimating lens 802 may propagate the light to the diffraction grating 516 through a long pass filter 704, which again may be configured to filter off the shorter wavelength components of the light 504. The sample holder 200 can be placed near the detector 524, or near the collimation lens 802, for example on either side of long pass filter 704.

The diffraction grating 516 may diffract the light 504 into separate beams 504-1, 504-2, and 504-3. As the beams 504-1, 504-2, and 504-3 diverge (e.g., defocus) from the diffraction grating 516, a lens 804-1 may collimate the beams 504-1, 504-2, and 504-3 to another lens 804-2. The other lens 804-2, being similarly configured to the lens 804-1 but positioned in opposition to the lens 804-1, may focus each of the beams 504-1, 504-2, and 504-3 onto the DMD 520. The DMD 520 may then selectively activate certain mirrors to propagate the light 504 to the detector 524. For example, the DMD 520 may activate mirrors that direct the three distinct beams 504-1, 504-2, and 504-3 of the light 504 towards the detector 524 at similar or different locations on the sample holder 200, in relation to the pattern programmed onto the DMD. Thus, the DMD 520 may selectively measure a different component of the blood 104 therein. The optical element 522 may focus each of the beams 504-1, 504-2, and 504-3 on the sample holder 200 and ultimately to the detector 524.

Figure 9:
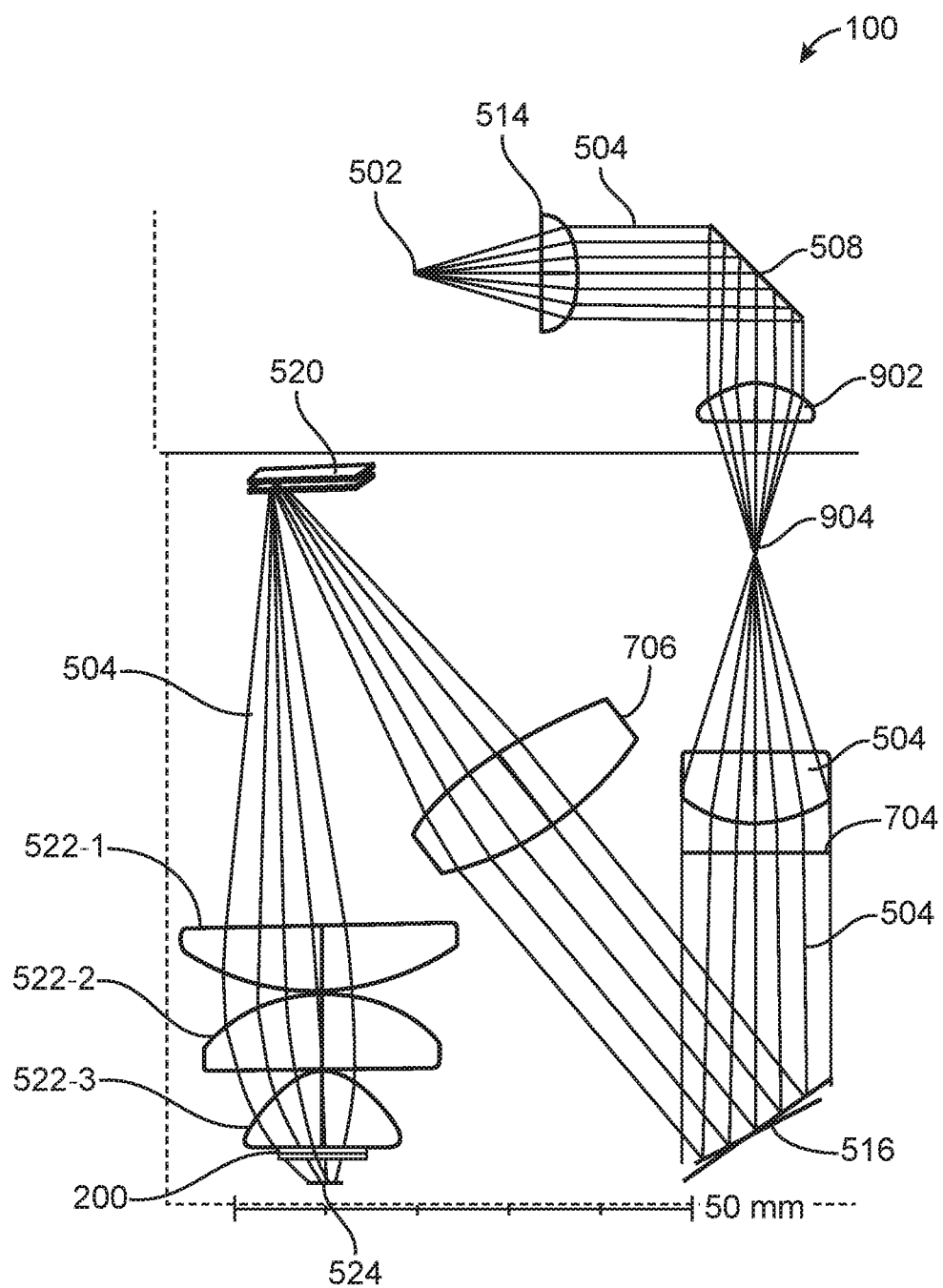
FIG. 9 shows an optical schematic of a spectrometer comprising yet another optical configuration, in accordance with some embodiments.

FIG. 9 shows an optical schematic of a spectrometer 100 comprising various optical elements in yet another exemplary optical configuration, in accordance with some embodiments. In this embodiment, the illumination source 502 propagates the light 504 to a collimating lens 514. The collimating lens 514 may collimate the light 504 to a fold mirror 508. The fold mirror 508 may condense the optical configuration by propagating the light 504 at a substantial right angle with respect to the collimated light 504 from the collimating lens 514. Thus, the light from the fold mirror 508 may maintain the collimation of the light 504.

The fold mirror 508 may propagate the light to a focusing lens 902. The focusing lens 902 may have a focal length at which the light 504 focuses and begins to diverge (i.e., beam waist 904). A collimating lens 504 may be positioned at a point where the light 504 diverges. The collimating lens 504 may collimate the light through a long pass filter 704 onto the diffraction grating 516. Again, the long pass filter 704 may be configured to filter out shorter wavelengths of the light 504.

In some embodiments, the fold mirror 508 comprises a curved mirror to focus light, which allows fewer optical components to be used. For example, fold mirror 508 may comprise a free form optics mirror to focus light to a beam waist and replace focusing lens 902.

The diffraction grating 516 may diffract the collimated light 504 through a focusing lens 706 to focus the light 504 onto the DMD 520. The DMD 504 may selectively activate mirrors of the DMD 504 to propagate light 504 through a focusing optical configuration comprising the optical elements 522-1, 522-2, and 522-3 (e.g., focus lenses). Thus, the light 504 may impinge the sample holder 200 at different locations to illuminate different components of the blood 104 therein where they may then be detected by the detector 524.

In some embodiments, the sample holder 200 may be placed at the beam waist 904. For example, the sample holder 200 may be placed at or about the focal length of the focusing lens 902 so as to focus the collimated light 504 onto the sample holder 200. The remaining optics therefore may operate on the light from the illuminated sample of blood 104. An example of such is shown and described below in FIG. 14.

Figure 10:
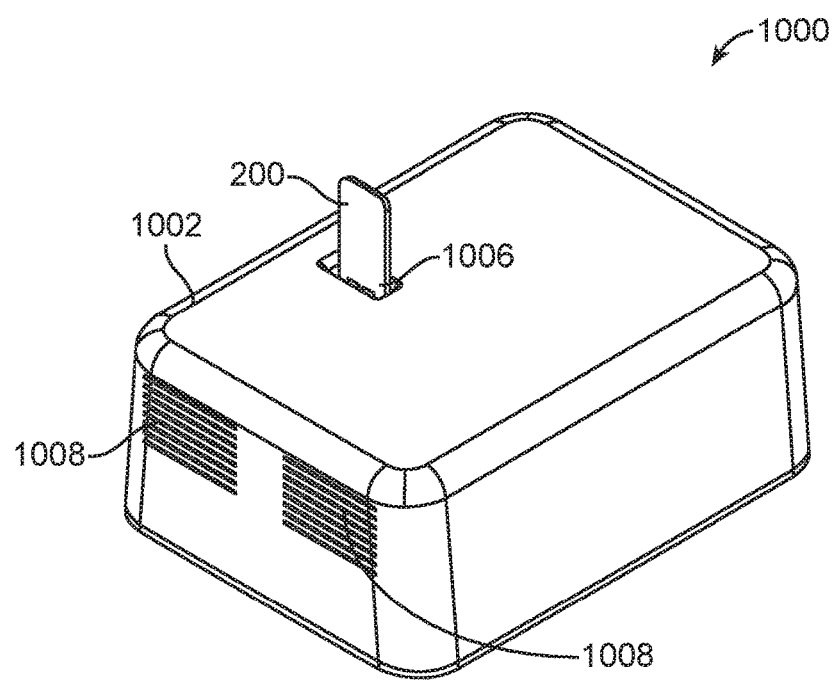
FIG. 10 shows a perspective view of an exemplary spectrometer in a housing, in accordance with some embodiments.
Figure 11:
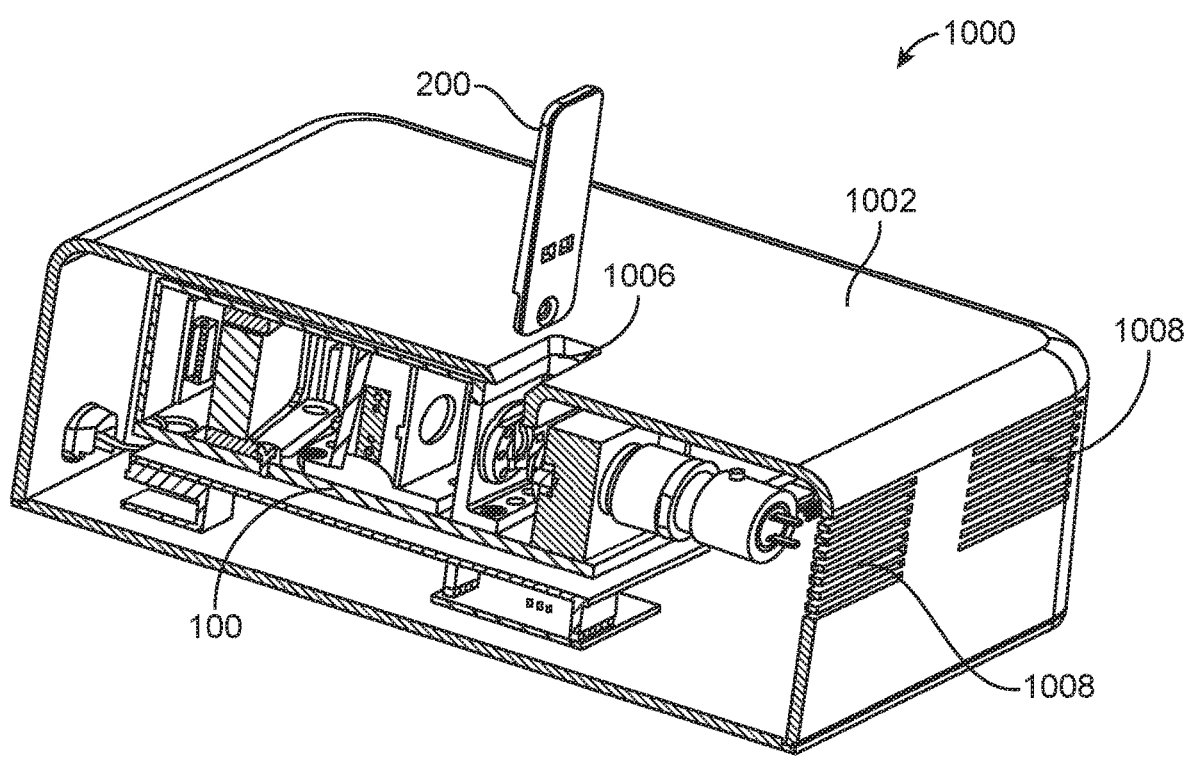
FIG. 11 shows a perspective/cut-away view of the spectrometer of FIG. 10, in accordance with some embodiments.

FIG. 10 shows a perspective view of an exemplary spectrometer 1000 in a housing 1002, in accordance with some embodiments. FIG. 11 shows a perspective/cut-away view of the spectrometer 1000 of FIG. 10. The housing 1002 is configured with an opening 1006 through which the sample holder 200 passes and inserts into the receptacle of the spectrometer 1000. In this regard, the sample holder 200 may contain a sample of the blood 104 of a subject. And, the sample holder 200 may allow the blood 104 to at least partially separate into its various components. Thus, the spectrometer 1000 may selectively measure individual components of the blood 104 in any manner shown and described hereinabove. The spectrometer 1000 may be configured in accordance with any of the spectrometer embodiments disclosed herein. Similarly, the sample holder 200 may be configured in accordance with any of the sample holder embodiments disclosed herein.

Also illustrated in this embodiment are vents 1008. The vents 1008 may be configured to provide active and/or passive cooling to the spectrometer 1000. For example, while the spectrometer 1000 may be configured with a spectrometer device 100 as shown and described above that prevents overheating of the sample of blood 104 by distally locating the sample holder 200 away from an illumination source, the spectrometer 1000 of this embodiment may also incorporate one or more fan modules to force warmer air from the illumination source through the vents 1008 to cool the interior of the spectrometer 1000. Alternatively or additionally, the vents 1008 may allow cooler exterior air to flow into the spectrometer 1000 to cool the interior of the spectrometer 1000.

The internal components of the spectrometer shown in FIGS. 10 and 11 may comprise one or more components and configurations of the spectrometer as described herein. For example, the components can be configured in accordance with FIGS. 5 and 6, with opening 1006 corresponding to a location between the optics 506 and 510 of FIG. 5 and between collimation lens 514 and long pass filter 602 of FIG. 6, for example.

FIG. 12 shows a perspective view of an exemplary spectrometer 1100 in another housing, in accordance with some embodiments. FIG. 13 shows various views of the spectrometer 1100 of FIG. 12, in accordance with some embodiments. In these embodiments, the housing 1102 is configured with an opening 1106 through which the sample holder 200 passes and inserts into the spectrometer 1100. In this regard, the sample holder 200 may contain a sample of the blood 104 of a user. And, the sample holder 200 may allow the blood 104 to separate or at least partially separate into its various components. Thus, the spectrometer 1100 may selectively measure individual regions of the sample of the blood 104 in any manner shown and described herein. As with FIGS. 10 and 11, the spectrometer 1100 may be configured in accordance with any of the spectrometer embodiments disclosed herein, and the sample holder 200 may be configured in accordance with any of the sample holder embodiments disclosed herein, and may comprise one or more components of collector 300.

Figure 14:
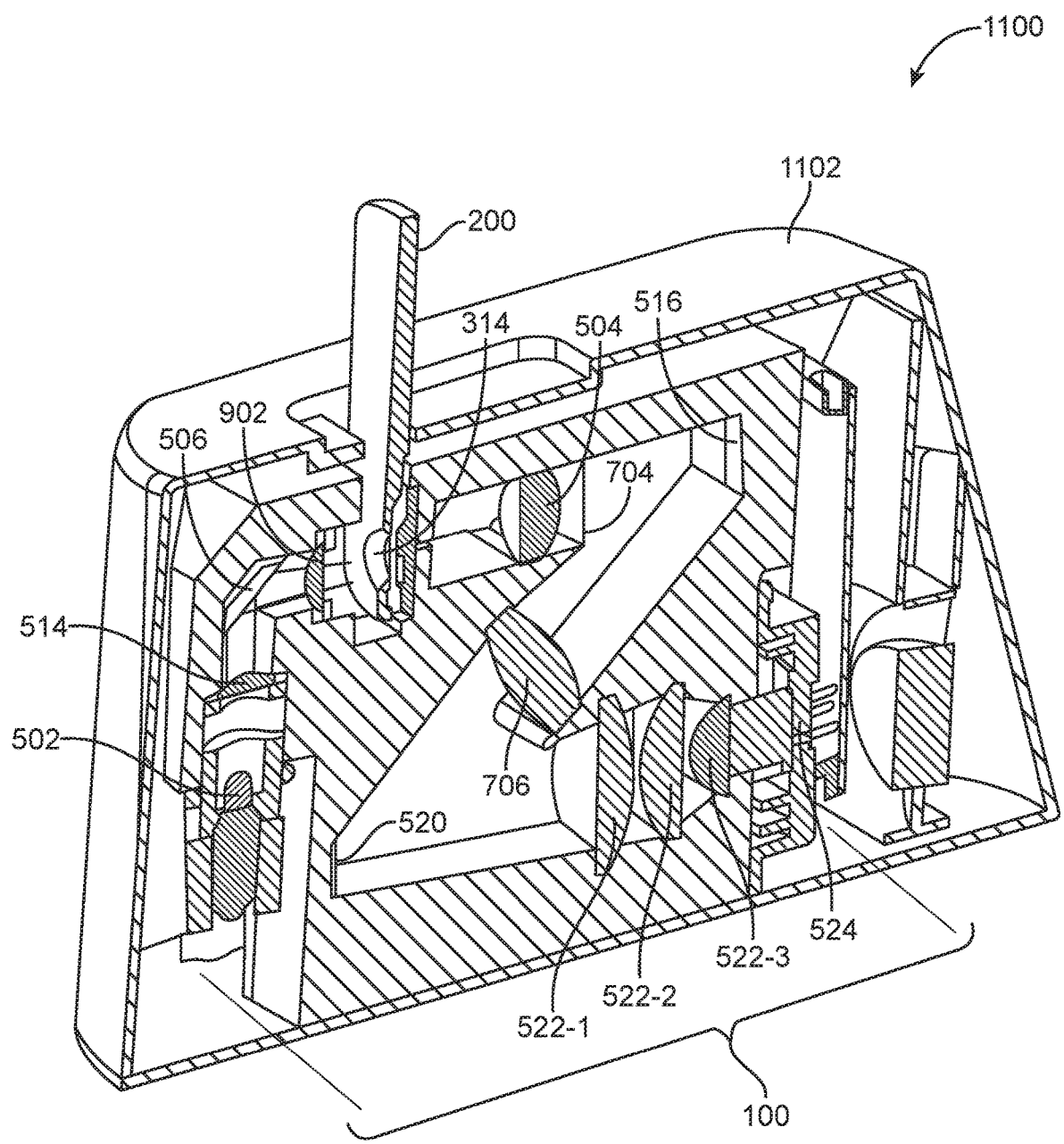
FIG. 14 shows a perspective/cut-away view of the spectrometer of FIG. 12 with an exemplary optical configuration, in accordance with some embodiments.

FIG. 14 shows a perspective/cut-away view of the spectrometer 1100 of FIG. 12 with an exemplary optical configuration, in accordance with some embodiments. In this embodiment, the spectrometer 1100 comprises the optical configuration of the spectrometer device 100 of FIG. 9. The sample holder 200 can be placed at a beam waist as described herein, for example between lens 902 and lens 504, for example. As discussed above, the sample holder 200 in this embodiment is positioned at or about the focal length of the focusing lens 902 such that the collimated light 504 is focused onto the sample holder 200 and the remaining optics may therefore operate on the light 504 from the illuminated sample of blood 104. The wavelength spectra from the various components of the blood 104 may then be collected by the detector 524.

Figure 15:
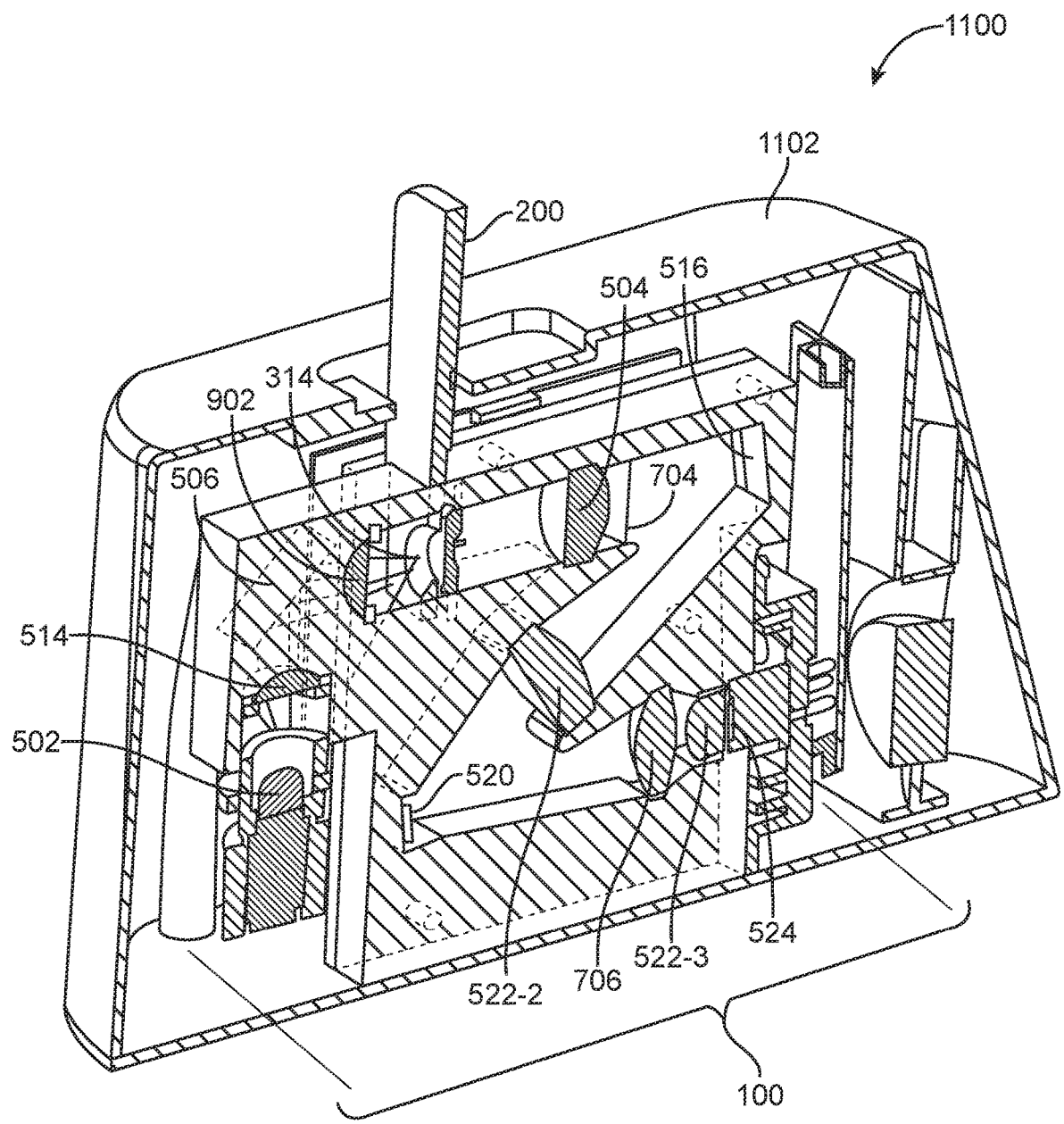
FIG. 15 shows a perspective/cut-away view of the spectrometer of FIG. 12 with another exemplary optical configuration, in accordance with some embodiments.

FIG. 15 shows a perspective/cut-away view of the spectrometer 1100 of FIG. 12 with another exemplary optical configuration, in accordance with some embodiments. In this embodiment, the spectrometer 1100 comprises the substantially the same optical configuration of the spectrometer device 100 of FIG. 14. Differing from the embodiment of FIG. 14 is the placement of the focusing lens 522-2 between the DMD 520 and the diffraction grating 516, and the placement of the focusing lens 706 between the DMD 520 and the detector 524.

This embodiment may be used to focus collimated light 504 to the DMD 520. For example, the light 504 propagating from the diffraction grating 516 may be collimated. The focusing lens 522-2 may focus the collimated light 504 to the DMD 520 which may selectively reflect the light 504 to the focusing lens 706 and the focusing optical element 522-3 such that certain portions of the light 504 detected by the detector 524.

Again, the sample holder 200 may be positioned at or about the focal length of the focusing lens 902 such that the collimated light 504 is focused onto the sample holder 200 and the remaining optics may therefore operate on the light 504 from the illuminated sample of blood 104. The wavelength spectra from the various components of the blood 104 are then collected by the detector 524.

Figure 16A:
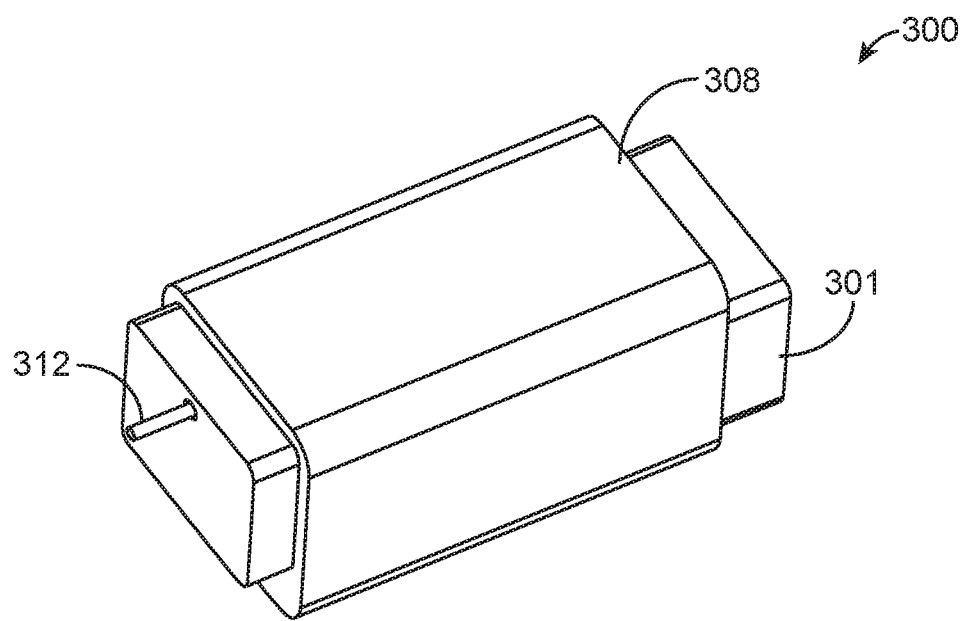
FIGS. 16A and 16B show perspective views of an exemplary sample holder, in accordance with some embodiments.
Figure 16B:
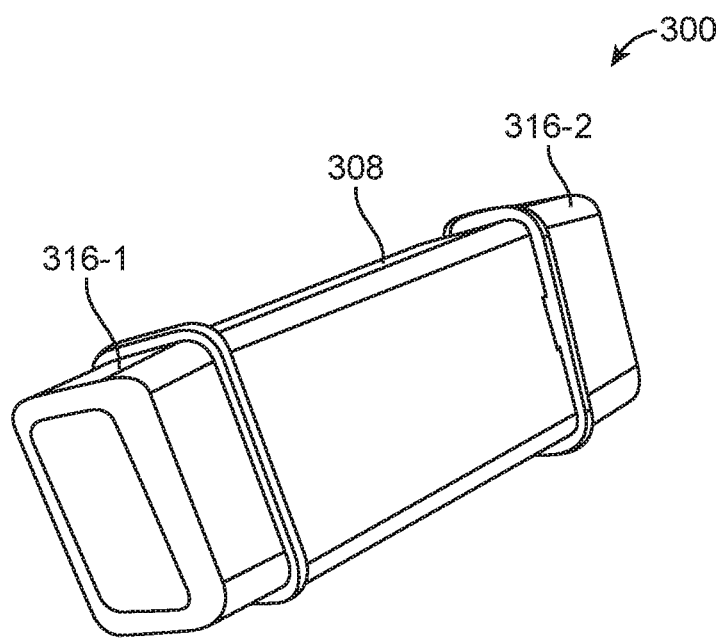

FIGS. 16A and 16B show perspective views of an exemplary blood sample collector 300, in accordance with some embodiments. As shown in FIG. 16A, the sample holder 200 is configured in a housing 308 and the tube 312 may extend from the sample holder 200. As discussed above, when the user depresses the button 301, the lancet needle 302 illustrated in FIG. 3 may extend through the tube 312 to collect the user's blood 104 which may then be retained within the sample holder 200.

FIG. 16B illustrates an embodiment with lids 316-1 and 316-2 disposed at both ends of the blood sample collector 300. The lids 316-1 and 316-2 may be configured to keep out impurities such that the sample of blood 104 does not get contaminated.

Figure 17:
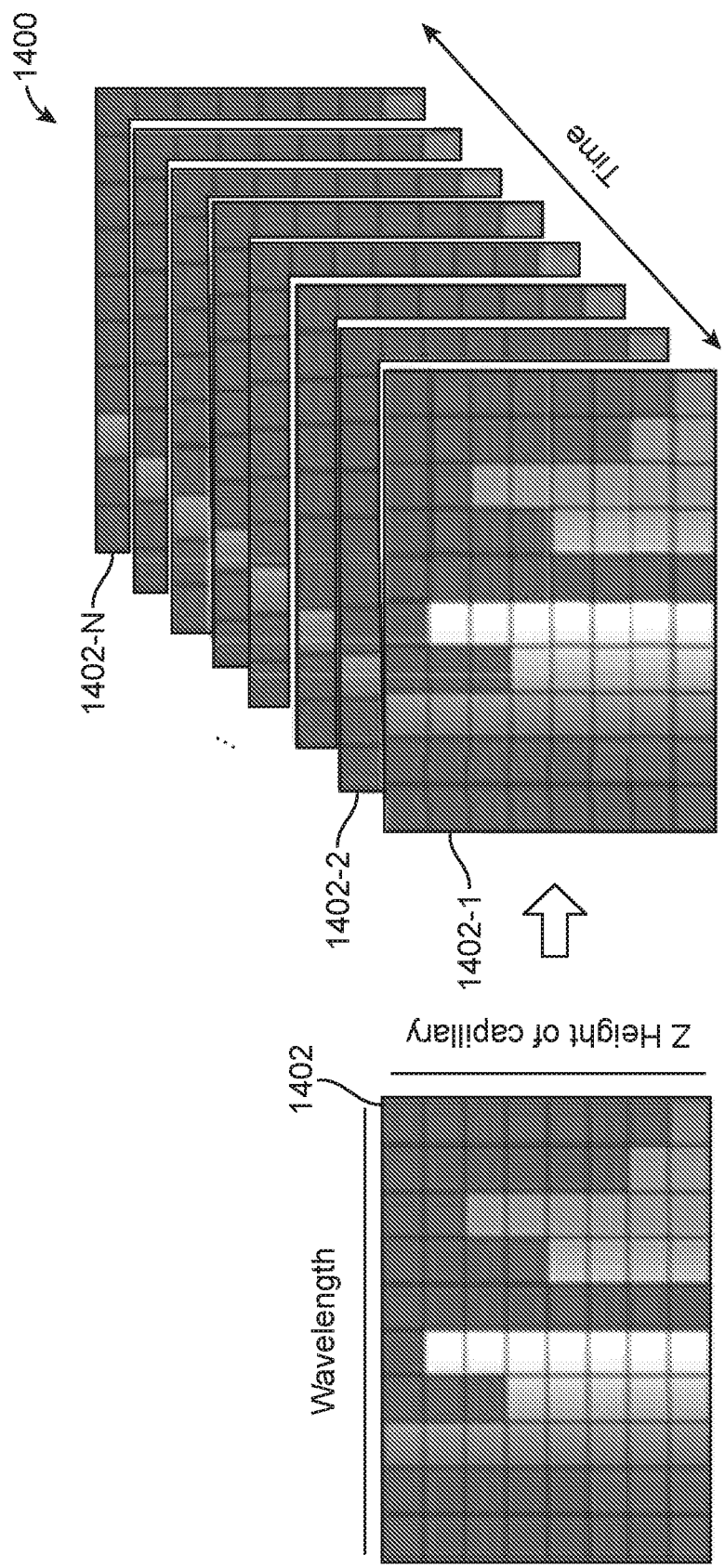
FIG. 17 shows exemplary wavelength plots over time from a spectrometer, in accordance with some embodiments.

FIG. 17 shows spatially resolved spectral data 1400 over time from a spectrometer, in accordance with some embodiments. The spatially resolved spectral data 1400 may comprise a plurality of spatially resolved spectral measurements acquired at each of a plurality of times.

An exemplary plot 1402 of the spatially resolved spectral data 1400 shows the intensity at each of a plurality of wavelengths for each of a plurality of heights of the blood column in the sample holder such as a capillary tube as described herein. The spectrometer can be configured to measure the spectra of the blood sample at a height Z in the column of blood as the sample separates. The height Z can range from about 1 mm to about 20 mm, for example from about 2 mm to about 10 mm. The number of spatially resolved samples locations along the height Z can range from about 2 to about 1000, for example within a range from about 5 to about 100. The mirror, phase modulator, grating or other wavelength selective component under computer control can be configured to measure the spectrum of the sample at each of the plurality of spatially resolved locations along the height of the sample.

The spectra are recorded for each location along the height of the column. The processor can be configured with instructions to measure each of a plurality of spatially resolved spectra, starting with first spatially resolved spectral data corresponding to a first plot 1402-1 at a first time, followed second spatially resolved spectral data corresponding to a second plot 1402-2 at a second time, up to Nth spatially resolved spectral data acquired at Nth time and corresponding to an Nth plot 1402-N. The spatially resolved spectral data can be measured while the blood sample separates and stored by the processor as described herein.

The separation of the blood sample into red blood cells, plasma, white blood cells and platelets may comprise a gravimetric separation in which blood in the column at least partially separates into these components in response to gravity and different densities among the blood components as described herein. The timing of the separation and other spectral signals and the locations of these spectral signals in the separating blood column can provide useful information.

In some embodiments, the spatially resolved spectral data comprise hypercubes of spectral data comprising one or more of:

Quantitative molecular spectroscopic data of whole blood as it separates;

Mass separation rates, counts, heights, volume; or

Induced perturbations (including temperature, pressure, drying, coagulation agglutination, specialized chemical reaction).

The data may be labeled with real time information from lifestyle experiments such as food, exercise, supplements, etc.

The hypercubes of data may comprise vectors, in which each vector comprises a first dimension corresponding to spectral wavelength data, a second dimension corresponding to a spatial location of the spectral wavelength data, and a third dimension corresponding to time. For example, the first and second dimension may correspond to spatially resolved spectral data 1400 obtained at a time. The third dimension corresponding to time may comprise changes in the spatially resolved spectral data, for example changes to the spatially resolved spectral data as the blood separates.

Figure 18:
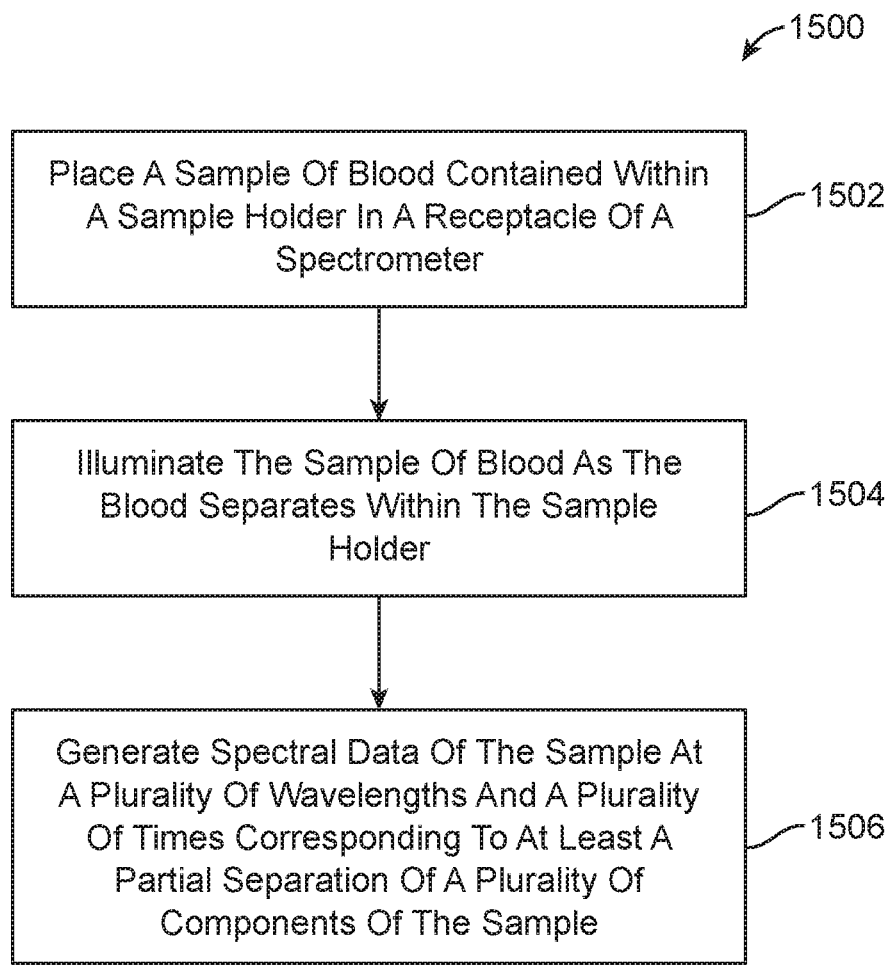
FIG. 18 shows a flowchart of an exemplary blood spectroscopy process, in accordance with some embodiments.

FIG. 18 shows a flowchart of an exemplary blood spectroscopy process 1500, in accordance with some embodiments. In this embodiment, a sample of blood contained within a sample holder (e.g., the sample holder 200) is placed in a receptacle of a spectrometer a spectrometer, such as the spectrometer 100 disclosed herein, in the process element 1502. The spectrometer may illuminate the sample of blood as the blood separates within the sample holder, in the process element 1504. For example, the blood may at least partially separate into a plurality of components, such as plasma, red blood cells, white blood cells, and the like as it is drawn into the sample holder. From there, the spectrometer and/or some other processing system may generate spectral data of the sample at a plurality of wavelengths and a plurality of times corresponding to at least a partial separation of a plurality of components of the sample, in the process element 1506.

Examples of suitable biomarkers and chemometric analysis suitable for determining biomarkers are also described in PCT/US2016/026825, filed Apr. 8, 2016, entitled "METHOD AND APPARATUS FOR DETERMINING MARKERS OF HEALTH BY ANALYSIS OF BLOOD", the entire disclosure of which is incorporated herein by reference. Although many chemometric approaches can be used, in some embodiments, a genetic algorithm is used to determine an amount of biomarker for a given biomarker channel. A plurality of spectral bins can be combined with appropriate weighting of each of the spectral channels in order to an amount of a biomarker. For example, approximately 300 to 400 spectral bins can be combined to determine a parameter related to health such as blood pressure.

Additional approaches can be used with appropriate references and blood samples to determine the markers and biomarkers as disclosed herein, such as Partial Least Squares ("PLS") regression, and Null Augmented Regression ("NAR"). The NAR may comprise PLS coupled with Tikhonov Regularization that leverages the constant-analyte spectra of within-sample measurements of the calibration data. Random Forest Regression Tree ("RF/RT") can also be employed. The RF/RT methodology can be used alternatively or in combination with a genetic algorithm as described in PCT/US2016/026825, the full disclosure of which has been previously incorporated by reference.

A channel of a biomarker may comprise the pure component spectrum of a blood biomarker. The channel can be determined by calibrating the instrument using a set of labeled blood samples where the concentrations of the biomarker are varied orthogonally to each other in a set of samples. This approach can be used to define the marker and biomarker channels as disclosed herein, such as "glucose channel" and a "HDL channel." In some embodiments, a channel is monitored for a change (or lack of change) during a lifestyle modification experiment as described herein. At the end of the experiment, which can last approximately 3 weeks, the channel is evaluated to determine whether the channel readout comprises a value higher or lower than where it started, or an unchanged value.

EXPERIMENTAL

The present inventor has conducted experiments to show the accuracy of the measurements obtained with spectrometers and blood samples as described herein. The Proficiency Testing ("PT") blood samples were obtained from the American College of Physicians. The samples were used to test and verify the accuracy of the presently disclosed spectrometer methods and apparatus. Similar samples have been used to analyze many labs, resulting in highly accurate reference concentrations, and the reference error analyzed. The experiments were conducted with 10 samples, each run 4 times. The data were analyzed chemometric methods and a 10-fold "subject" out cross validation v. mean of all labs approach. The chemometric methods included Partial Least Squares ("PLS") regression, and Null Augmented Regression ("NAR"). The NAR included PLS coupled with Tikhonov Regularization that leverages the constant-analyte spectra of within-sample measurements of the calibration data. Random Forest Regression Tree ("RF/RT") was also employed.

The spectrometer used for these experiments comprised a spectral range from approximately 1350 to 2450 nm with a 10 nm to 12 nm resolution, a 30,000:1 signal-to-noise ratio (SNR) in 1 sec, a single element InGaAs detector, a high resolution spectrum acquisition with up 1824 data points, and a digital mirror as described herein.

Figure 19:
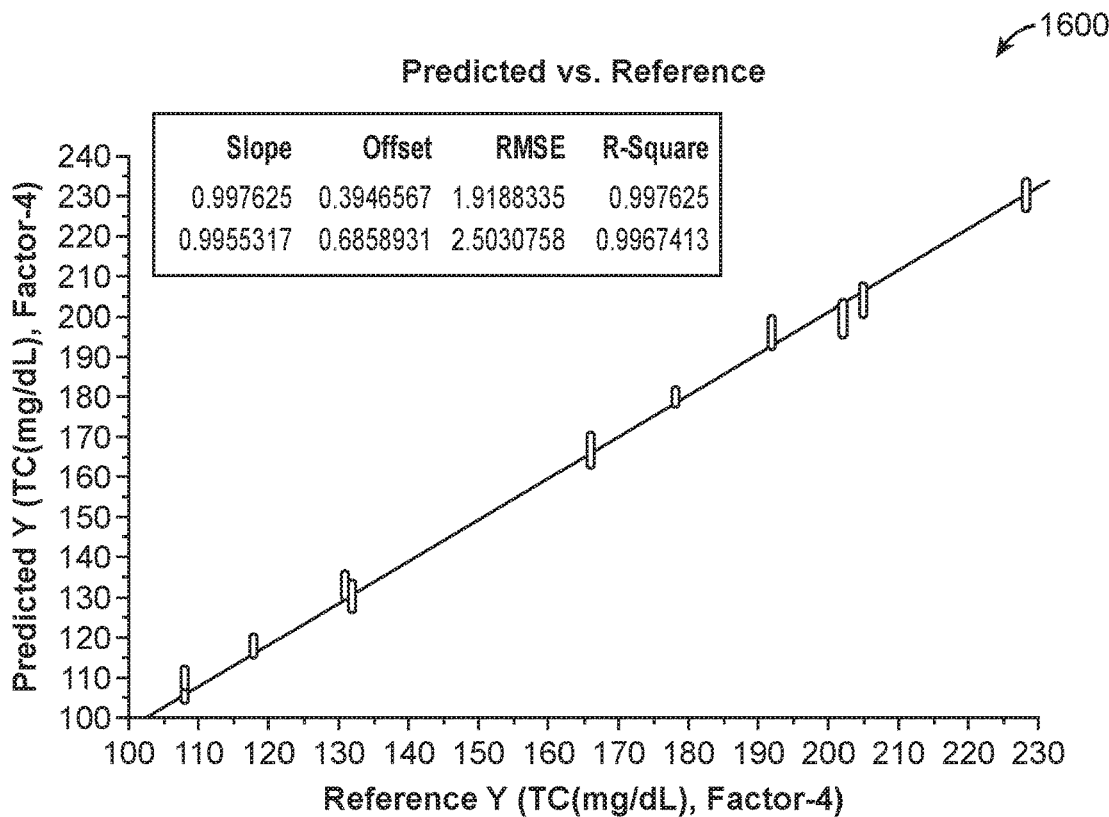
FIG. 19 shows correlations for total cholesterol ("TC"), in accordance with some embodiments.

FIG. 19 shows correlations for total cholesterol ("TC"). The Y axis shows total cholesterol predicted based on spectroscopic measurements, and the X axis shows the reference value from other measurement sources for the blood samples.

Figure 20:
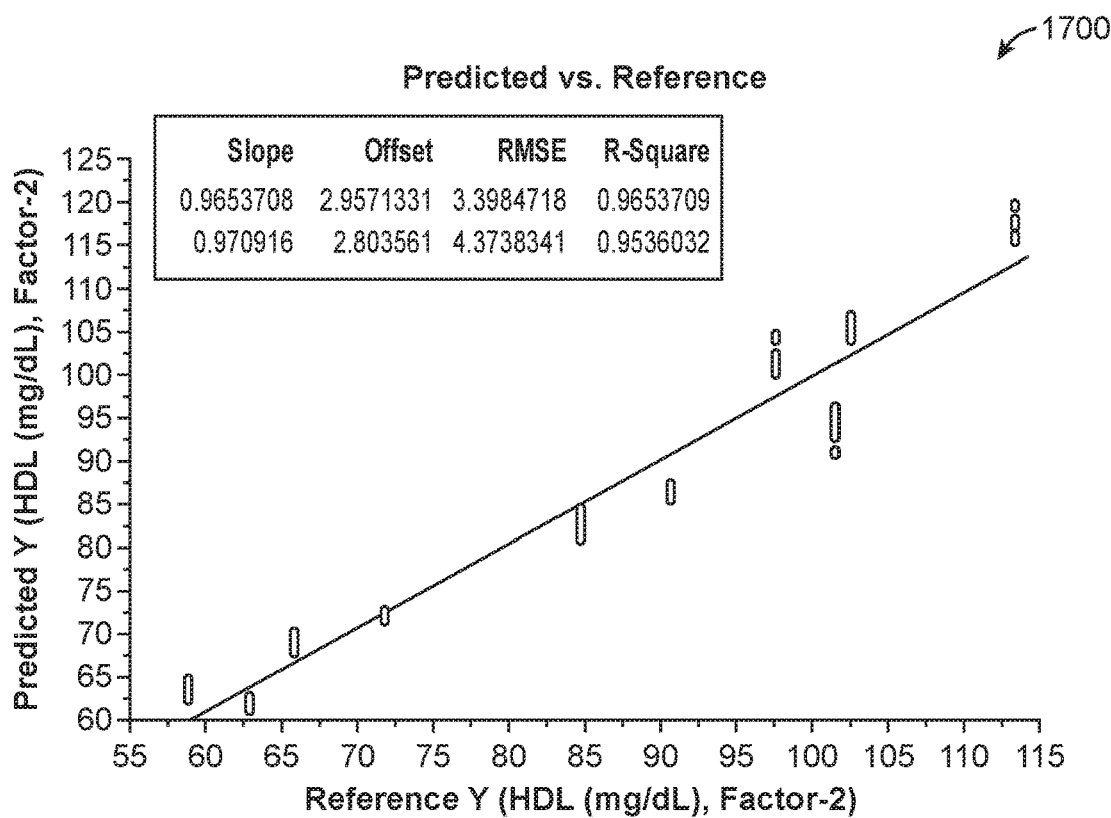
FIG. 20 shows correlations for high density lipoprotein ("HDL"), in accordance with some embodiments.

FIG. 20 shows correlations for high density lipoprotein ("HDL"). The Y axis shows HDL predicted based on spectroscopic measurements, and the X axis shows the reference value from other measurement sources for the blood samples.

Figure 21:
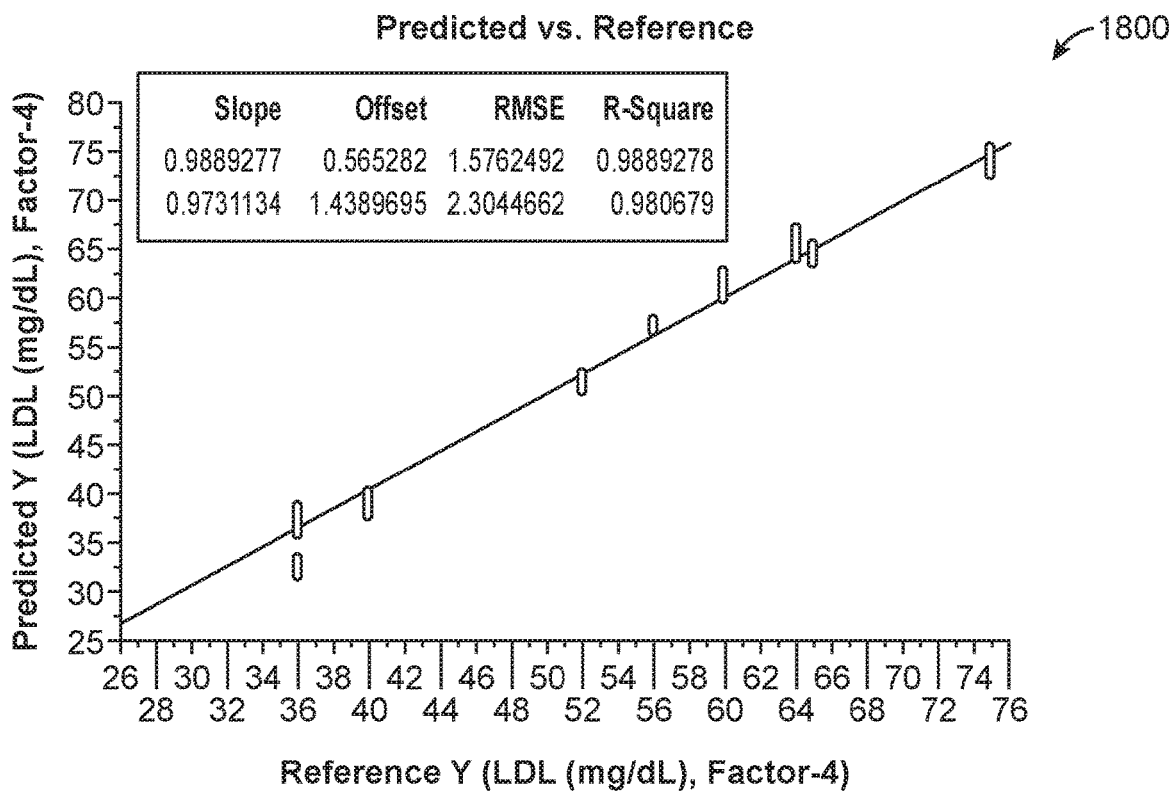
FIG. 21 shows correlations for low density lipoprotein ("LDL"), in accordance with some embodiments.

FIG. 21 shows correlations for low density lipoprotein ("LDL"). The Y axis shows LDL predicted based on spectroscopic measurements, and the X axis shows the reference value from other measurement sources for the blood samples.

Figure 22:
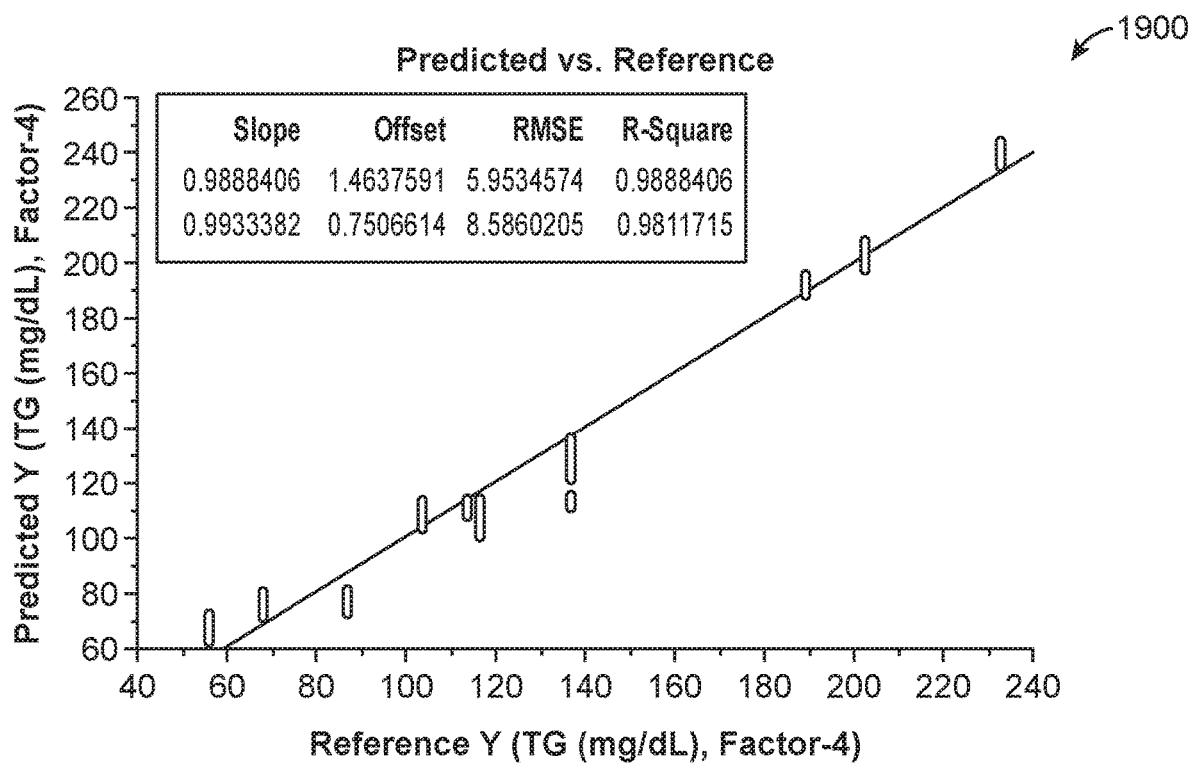
FIG. 22 shows correlations for triglycerides ("TG"), in accordance with some embodiments.

FIG. 22 shows correlations for triglycerides ("TG"). The Y axis shows TG predicted based on spectroscopic measurements, and the X axis shows the reference value from other measurement sources for the blood samples.

Figure 23:
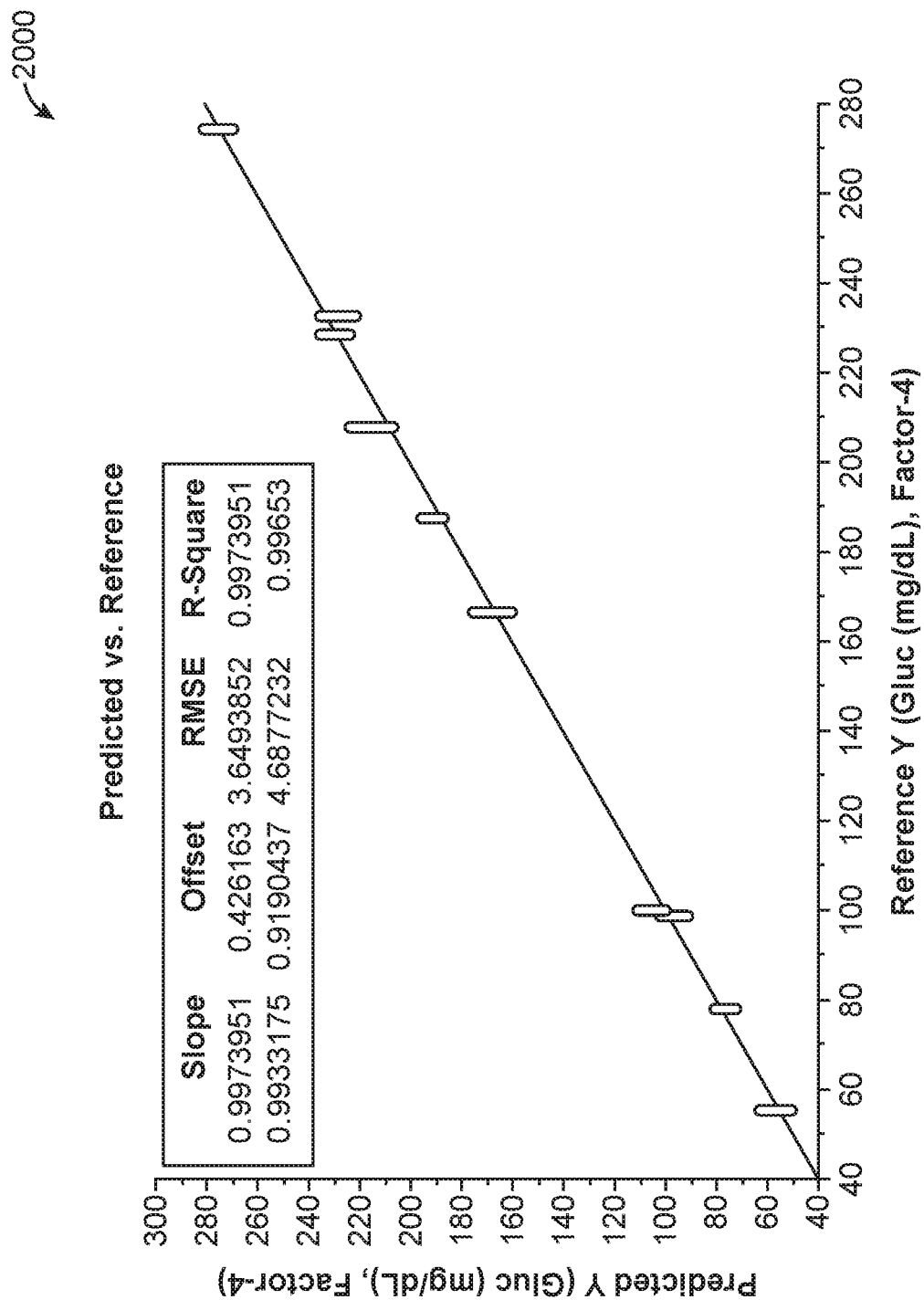
FIG. 23 shows correlations for glucose ("GLUCOSE"), in accordance with some embodiments.

FIG. 23 shows correlations for glucose ("GLUCOSE"). The Y axis shows GLUCOSE predicted based on spectroscopic measurements, and the X axis shows the reference value from other measurement sources for the blood samples.

FIG. 24 shows means and standard deviations for LDL from a blood sample measured at different labs. The data are shown for sample CH-11. This data shows a significant variation in the measured values for all measurement methods and a range from 30 to 83 for measurements from 64 labs. Similar data are shown for specific labs.

Figure 25:
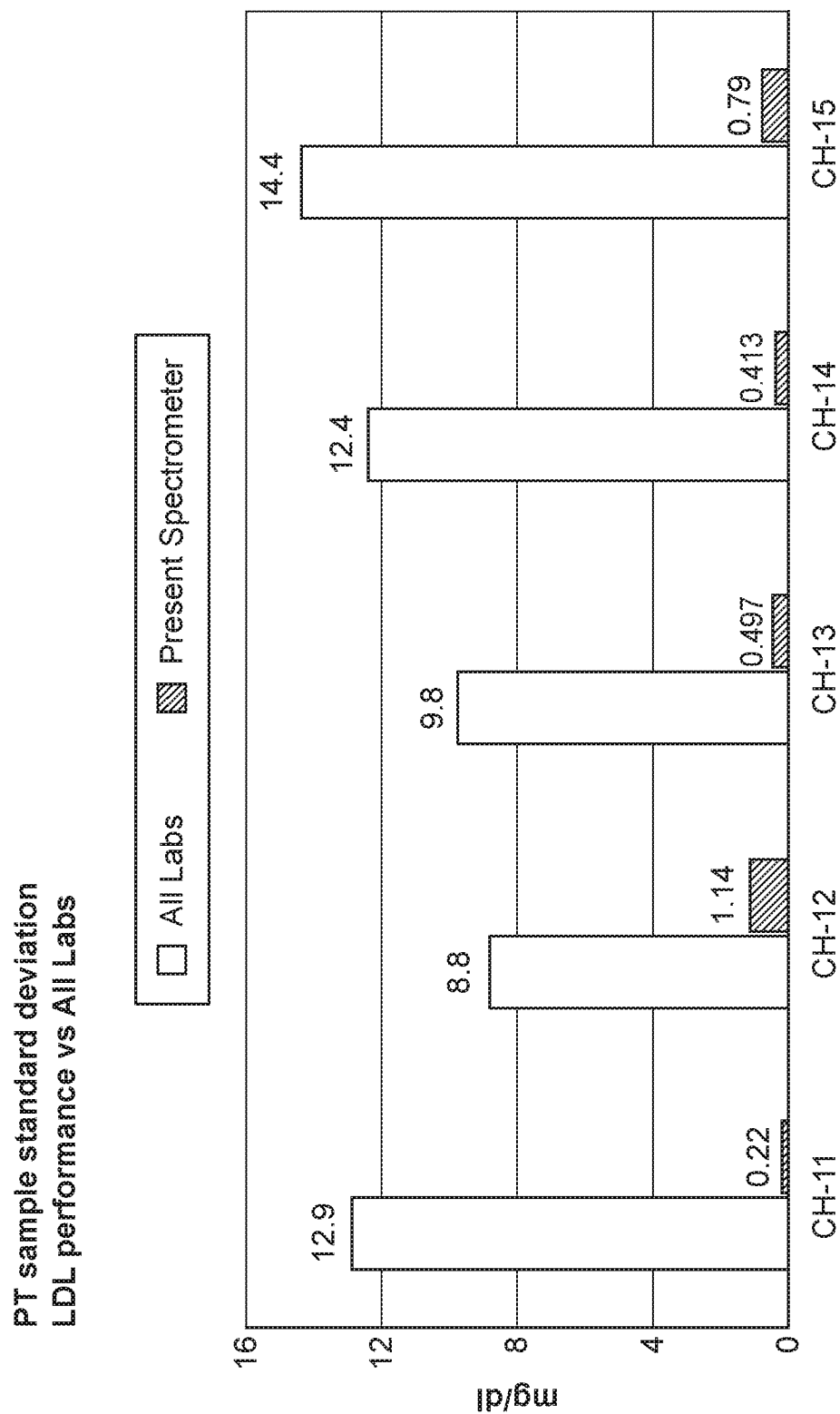
FIG. 25 shows PT testing standard deviation for LDL for the samples versus All Labs for samples CH-11, CH-12, CH-13, CH-14 and CH-15, in accordance with some embodiments.

FIG. 25 shows PT testing standard deviation for LDL for the samples versus All Labs for samples CH-11, CH-12, CH-13, CH-14 and CH-15. This data shows considerably lower variability with the spectrometer based approach as described herein. For example, with CH-11 for All Labs the LDL standard deviation is 12.9 mg/dL, whereas with the spectrometer based approach it is 0.22 mg/dL. The spectrometer based approach showed considerably less variability for the other samples.

FIG. 26 shows the cross-validated standard errors of prediction ("CVSEP") for HDL, LDL, Total Cholesterol, Triglyceride and Glucose. The CVSEP values are generally less than the Medically Allowable Error and Clinical Laboratory Improvement Amendments ("CLIA") allowable errors of the United States federal regulatory standards that apply to clinical laboratory testing performed on humans. The values for HDL, TC, TG and Glucose are clearly below the CLIA and Medically allowable error, although the LDL CVSEP is slightly above the allowable level. The CLIA allowable error can be calculated by multiplying CLIA acceptable performance criteria by the medical decision level as will be known to one of ordinary skill in the art of blood chemistry.

Additional experiments can be conducted in accordance with the teachings provided herein to measure the markers and biomarkers disclosed herein.

Figure 27:
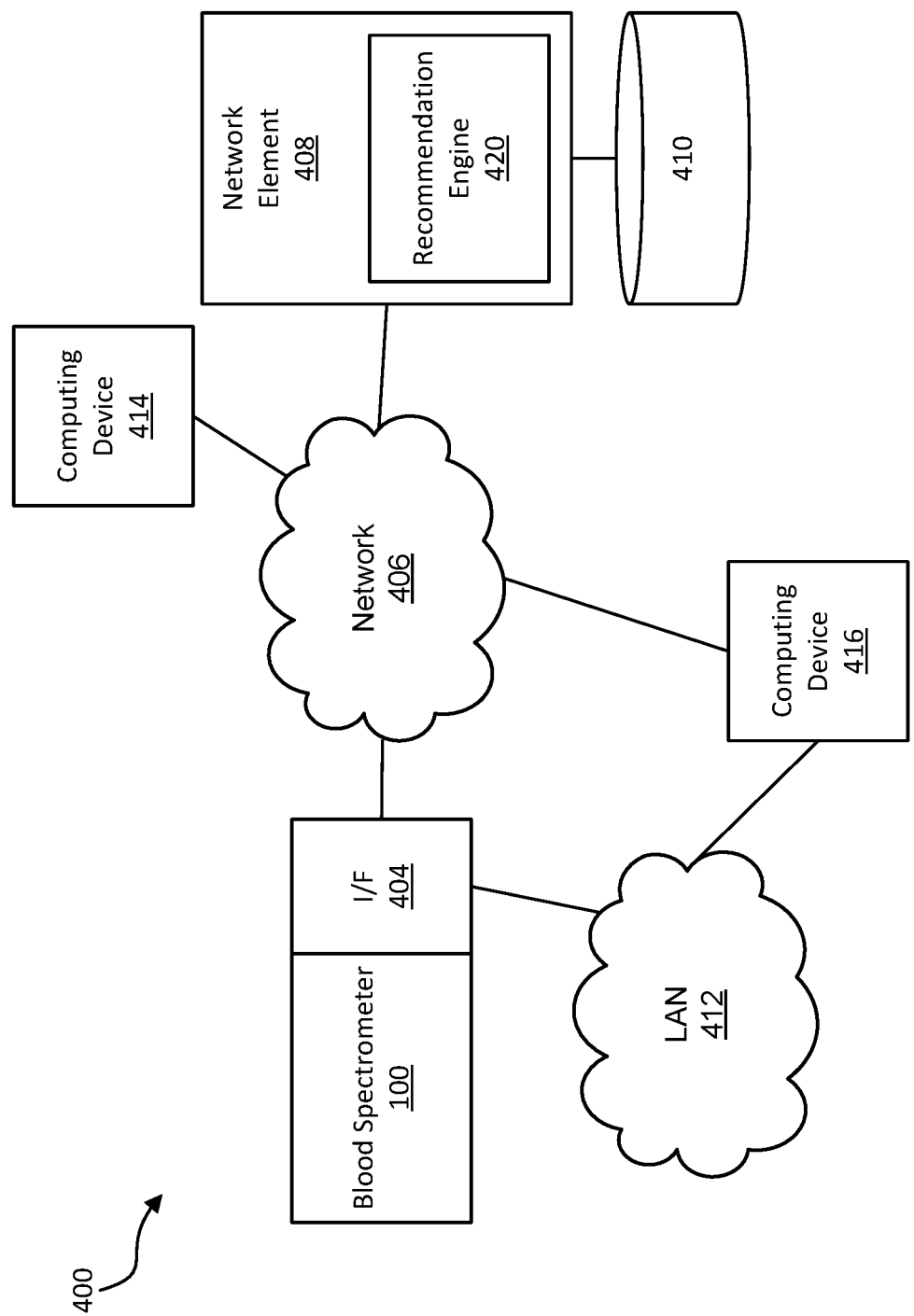
FIG. 27 shows a block diagram of an exemplary system comprising a blood spectrometer with network connectivity, in accordance with some embodiments.

FIG. 27 shows a block diagram of an exemplary system 400 comprising a blood spectrometer 100 with network connectivity, in accordance with some embodiments. The blood spectrometer 100 may be configured with, or coupled to, a network interface (I/F) 404 that is communicatively coupled to a network 406 (e.g., the Internet) and/or a local area network (LAN) 412. For example, the blood spectrometer 100 may be configured to receive a sample of blood contained within a sample holder, such as the sample holder 200. The blood spectrometer 100 may illuminate the sample of blood as the blood at least partially separates within the sample holder. And, a processor operatively coupled to the blood spectrometer 100 and/or configured with the blood spectrometer 100 may be configured with instructions to generate spectral data of the sample at a plurality of wavelengths and a plurality of times corresponding to at least partial separation of the sample of blood into a plurality of components of the sample.

When the blood spectrometer 100 detects the wavelength spectra of the various components of the blood 104, the blood spectrometer 100 may communicate the information pertaining to the wavelength spectra and/or the spectral data (e.g., spatially resolved spectral data acquired at a plurality of times) to the network 406 via the network I/F 404, which may in turn communicate the wavelength spectra and/or other spectral data to a network element 408 for subsequent processing. In this regard, the network element 408 may include, or be communicatively coupled to, a database 410 which may comprise various statistics and data pertaining to blood components that can be compared to and/or analyzed against the wavelength spectra of the blood 104. Alternatively or additionally, the blood spectrometer 100 may include processing on board that communicates other relevant information pertaining to the blood 104 through the network 406 to the network element 408. Examples of the network element 408 include computer network servers, computing devices, communication routers, processors, and the like.

Also illustrated in this embodiment, is a computing device 414 that is communicatively coupled to the network 406. The computing device 414 may be used to perform such analysis on the wavelength spectra and/or other spectral data of the blood from the blood spectrometer 100. In this regard, the computing device 414 may be in communication with the network element 408 to retrieve information pertaining to blood analysis such that a user of the computing device 414 (e.g., a medical professional, a trainer, or the like) can analyze the wavelength spectra from the blood spectrometer 100 and provide a diagnosis and/or other relevant information pertaining to the user's blood 104 to a user of the blood spectrometer 100. Examples of the computing device 414 include computers, smart phones, and the like, comprising various hardware (e.g., processors, memory, data storage devices, etc.), software, and/or firmware components for processing the wavelength spectra from the blood spectrometer 100.

In some embodiments where the blood spectrometer 100 is communicatively coupled to the LAN 412, the blood spectrometer 100 may be able to communicate wavelength spectra to a computing device 416. For example, the computing device 416 may also include computers, smart phones, and the like, comprising various hardware (e.g., processors, memory, data storage devices, etc.), software, and/or firmware components for processing the wavelength spectra and/or other spectral data from the blood spectrometer 100. In this regard, the computing device 416 may be that of the user using the blood spectrometer 100. For example, a user may draw his or her own blood 104 using the blood sample collector 300 above. The user may then input the sample of blood 104 into the blood spectrometer 100 to detect the various wavelength spectra of the components of the blood 104. The blood spectrometer 100 may then communicate the wavelength spectra to the user's computing device 416 such that the user may process the information and assess the user's own health.

Alternatively or additionally, the computing device 416 may receive information pertaining to the user's blood spectroscopy from the network element 408 and/or the computing device 414. For example, once the user performs a spectroscopy on the user's blood sample via the blood spectrometer 100, the blood spectrometer 100 may convey the information to the network element 408 for analysis. The network element 408 may in turn produce results (LDL and HDL cholesterol levels, glucose levels, oxygen levels, hydration levels, sodium levels, iron levels, etc.) from the blood spectroscopy. The network element 408 may then return those results and/or any other relevant information pertaining to those results to the computing device 416 such that the user may view the results.

In some embodiments, the blood spectrometer 100, the computing devices 414 and 416, and the network element 408, either alone or in combination, may be configured with instructions (e.g., software components) that direct a processor to perform one or more analyses. For example, a processor configured with the blood spectrometer 100, the computing devices 414 and 416, and/or the network element 408 may measure two of more of a high density lipoprotein, a total cholesterol, a triglyceride or a glucose of the sample with a cross-validated standard errors of prediction ("CVSEP") of no more than 12 mg/dL, 20 mg/dL, 40 mg/dL, 20 mg/dL, respectively, for each of the two of more of the high density lipoprotein, the total cholesterol, the triglyceride or the glucose of the sample, with the spectral data from the plurality of times corresponding to the at least partial separation. In some embodiments, the two or more comprises three or more of the total cholesterol, the triglyceride or the glucose of the sample with the cross-validated standard errors of prediction of no more than 12 mg/dL, 20 mg/dL, 40 mg/dL, 20 mg/dL. In some embodiments, the three or more comprises four or more of the total cholesterol.

In some embodiments, the processor may measure the sample a plurality of times within a range from one minute to about 1 hour while the sample separates, and optionally within a range from about 2 minutes to about 30 minutes, and optionally within a range from about 5 minutes to about 15 minutes.

In some embodiments, the processor may measure one or more of a hormone (e.g., one or more of dehydroepiandrosterone ("DHEA"), Testosterone, Growth Hormone, Parathyroid Hormone, Estradiol, Progesterone, or Cortisol), a health and performance marker, the health and performance marker (e.g., one or more of Vitamin B12, PSA, Thyrogobulin, Troponin, IGF-1, Aldosterone, Prolactin, Creatine Kinase, Ferritin, Selenium, Homocystine, Copper, Ammonia, Folic Acid, AGE, or Cortisol), a metabolic marker (e.g., one or of Glucose, HbA1c, Glycated Albumin, Ketones, β-Hydroxybutyrate, Albumin, Total protein, BUN, Uric acid, Glutamate, GSH, Lactic Acid, CO2, pH, or Hydration), an immunology, inflammation and hematology marker (e.g., one or more of Fibrinogen, hsCRP, Globulins, Hematocrit, Hemoglobin, Erythrocyte sedimentation rate, Glutathione, Uric acid, Serum Amyloid A, Haptoglobin, WBC Count estimate, Transferrin saturation, Pyruvate, RBC count estimate, Platelet count estimate, Prothrombin time/INR, Interleukin-6), a cardiovascular marker (e.g., one or more of Cardiovascular total Cholesterol, HDL, LDL, Triglycerides, BNP, Apolipoprotein, or Average Blood Pressure), a marker of stress and toxins (e.g., one or more of Creatinine, Albumin, Carboxyhemoglobin, Ethanol, Carbon monoxide, Salicylates, Acetominophen, or Caffeine).

In some embodiments, the blood spectrometer 100 comprises a broad spectrum light source to generate a plurality of wavelengths of light, a detector (e.g., the detector 524 above), and a wavelength selector coupled to the broad spectrum light source to selectively direct light toward the detector with the sample located between the wavelength selector and the detector. The wavelength selector may comprise one or more of a dispersive element, a prism, a grating, a DMD, a diffractive optic, an interferometer, a Michelson interferometer, or an Etalon. In some embodiments, the blood spectrometer 100 comprises a digital micromechanical mirror optically coupled to the wavelength selector to selectively reflect the light from the wavelength selection to the detector.

In some embodiments, the detector comprises an indium gallium arsenide (InGaAs) detector. In some embodiments, the detector comprises a single element detector, while in other embodiments the detector comprises a plurality of detector elements. In some embodiments, the processor may take substantially continuous scans of blood sample with a duty cycle within a range from about 10% to about 90% of a light source illuminating a detector of the spectrometer. In some embodiments, the blood spectrometer 100 comprises a receptacle to receive the sample holder (e.g., the sample holder 200 and/or the blood sample collector 300 illustrated above) with the blood contained therein with an elongate axis of the sample holder oriented toward a vertical angle of inclination to separate the blood. In some embodiments, a number of spatially resolved sample locations along a height of the sample is within a range from about 2 to about 1000 and optionally within a range from about 5 to about 100.

In some embodiments, the plurality of wavelengths corresponds to a plurality of discretely resolved wavelength bands within a range from about 25 to about 1000 discretely resolved wavelength bands and the plurality of times is within a range from about 2 to about 1000 and optionally wherein the plurality of discretely resolved wavelength bands is within a range from about 50 to about 200 and the plurality of times is within a range from about 50 to about 100.

In some embodiments, the plurality of discretely resolved wavelength bands comprises a plurality of wavelength bands within a range from about 1500 nm to about 2000 nm. The range can be from about 1400 nm to 2400 nm.

In some embodiments, the blood spectrometer 100 comprises a maximum dimension of 170 mm and optionally the spectrometer comprises a length of no more that about 170 mm, a width of no more than about 75 mm, and a height of no more than about 100 mm and optionally the spectrometer comprises a length within a range from about 80 to about 170 mm, a width within a range from about 30 to about 75 mm and a height within a range from about 50 to about 100 mm and optionally the spectrometer comprises a volume within a range from about 120,000 mm3 (0.12 liter) to about 1,275,000 mm3 (1.275 liter). Based on the teachings provided herein, a person of ordinary skill in the art can decrease the dimensions with optics of decreased sizes and focal lengths, for example.

In some embodiments, the sample holder comprises an elongate channel. In this regard, the blood spectrometer 100 spectrometer may be configured to receive the sample holder and align the elongate channel of the sample holder 200 along a substantially vertical direction to separate the blood into the plurality of components along the elongate channel. The substantially vertical direction may comprise an angle within about 20 degrees of vertical. In this regard, a DMD of the blood spectrometer 100 and the processor may be configured to selectively scan a first region of the sample holder comprising a first component (e.g., blood plasma), and to selectively scan a second region of the sample holder comprising a second component (e.g., hematocrit). In some embodiments, the processor may be configured with instructions to determine an amount of time for the sample to separate into the first and second components.

In some embodiments, the processor directs substantially continuous scans of the sample with a duty cycle within a range from about 10% to about 90% of a light source illuminating a detector of the spectrometer.

The computing device may compare a first plurality of values of the biomarker channels to a second plurality of corresponding values of the biomarker channels, in the process element 806. Generally, the first plurality of values corresponds to a first measurement time and the second plurality of corresponding values corresponds to a second measurement time. Based on this information, the computing device may compute a change in at least one of the biomarker channels and output that change to the user device, in the process element 808.

In some embodiments, a computing device of the system 400, such as the computing device 414 and/or the network element 408, may comprise a recommendation engine 420 that presents one or more lifestyle change experiments to a user via a graphical user interface of a user device, such as computing device 416. For example, FIG. 28 shows an exemplary user device 2100 (e.g., a smart phone) that may be configured with a software module or "app" that is operable to implement a graphical user interface (GUI) 2102 that prompts a user to perform one or more experiments, as directed by the recommendation engine 420. The user may view the experiments in the GUI 2102 as illustrated in FIG. 29.

In this example, the GUI 2102 presents experiments pertaining to heart health by consuming beta glucan (experiment 2104-2), consuming oily fish (experiment 2104-4), consuming red yeast rice (experiment 2104-6). The user may select the experiment through the GUI 2102 by tapping the experiment on the user device 2100. From there, the user device 2100 may convey the selection to the computing device. The recommendation engine 420 may in turn prompt, based on the selected experiment, a reminder to the user to perform a lifestyle change in accordance with the experiment. Afterwards, the recommendation engine 420 may prompt the user to take a blood sample for processing by the blood spectrometer 100. The blood spectrometer 100 may then convey the results of the blood spectroscopy (e.g., spectral data) through the network 406 to the computing device for analysis. For example, the computing device may determine the effects of the experiment on the user, such as LDL and HDL cholesterol levels, glucose levels, oxygen levels, hydration levels, sodium levels, iron levels, etc. Afterwards, the recommendation engine 420 may present the results of the selected experiment based at least on the received spectroscopic data via the GUI 2102 of the user device 2100. An example of such is illustrated in FIG. 30.

Figure 30:
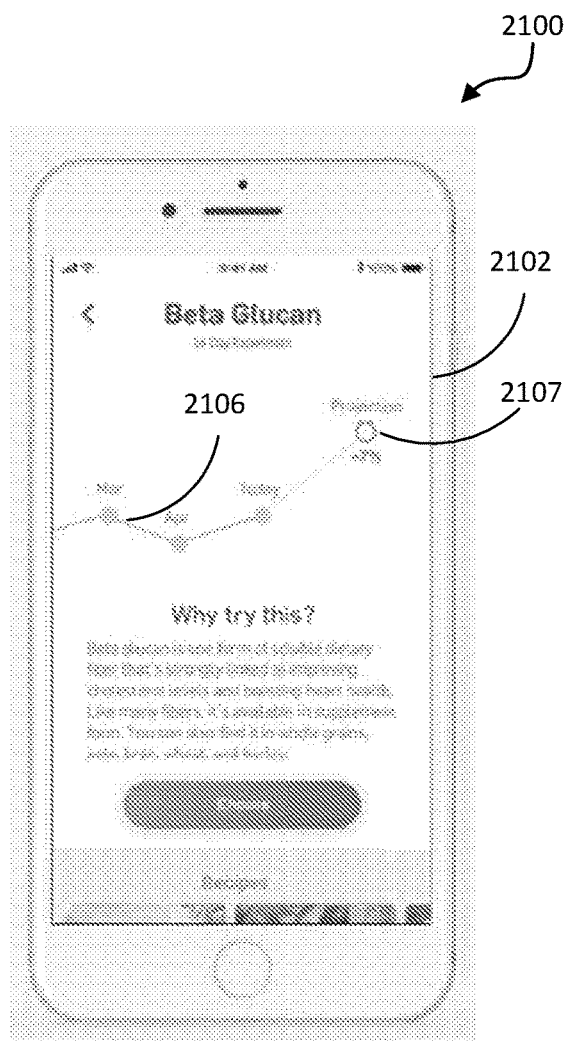

In FIG. 30, the user device 2100 exemplarily illustrates the results of the user's beta glucan experiment in the GUI 2102. For example, in the beta glucan experiment, the recommendation engine 420 may prompt the user a number of times to perform the experiment over the course of some duration (e.g., weeks or months). Each time, the recommendation engine 420 may direct the user through the software module on the user device 2100 to perform a blood spectroscopy on a new blood sample while the user is performing the experiment over the course of that duration. This information may be conveyed back to the computing device which updates the user's progress during the experiment and presents it as a line graph 2106 in the GUI 2102. The computing device may also compute and convey a projected result 2107 of the beta glucan experiment (e.g., the user selected experiment). The computing device may do the same for other experiments as well.

Figure 31:

As mentioned, the recommendation engine 420 may prompt the user over time to perform the user selected experiments. FIG. 31 illustrates an embodiment where the recommendation engine 420 conveys, through the network 406 to the user device 2100, a prompt for the user to perform the red yeast rice test in the GUI 2102. For example, if the user has not performed the test within a certain amount of time, the recommendation engine 420 may message the user device 2100 with an instruction to consume red yeast rice and/or perform another blood spectroscopy.

The recommendation engine 420 may also periodically send messages to the user device 2100 to inform and/or query the user. For example, FIG. 32A shows the GUI 2102 displaying a message from the recommendation engine 420 to the user asking how the red yeast rice experiment is going. FIG. 32B shows the GUI 2102 displaying a message from the recommendation engine 420 to the user with information pertaining to the benefits of red yeast rice.

Figure 33A:
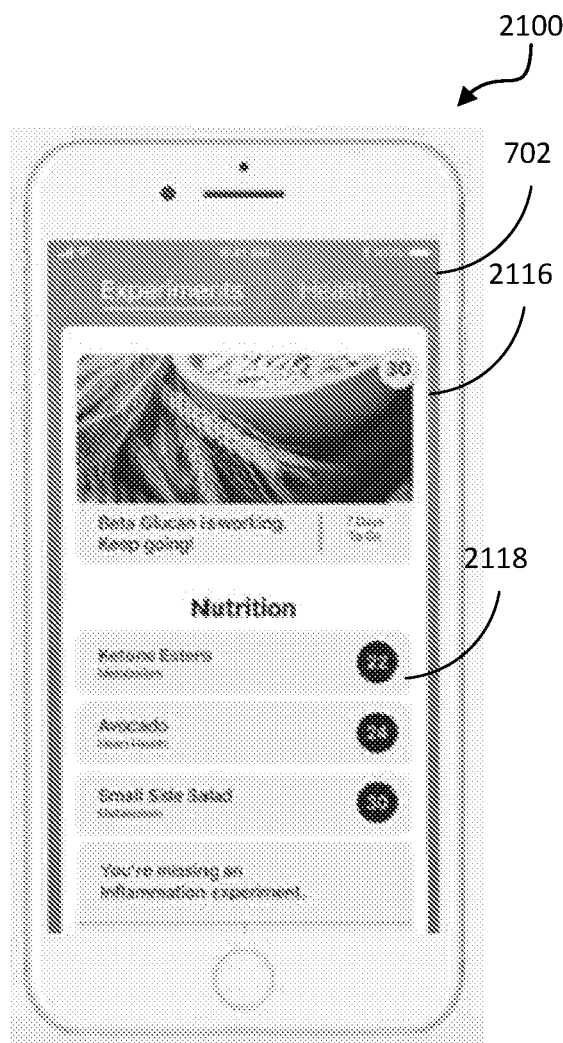
Figure 33B:
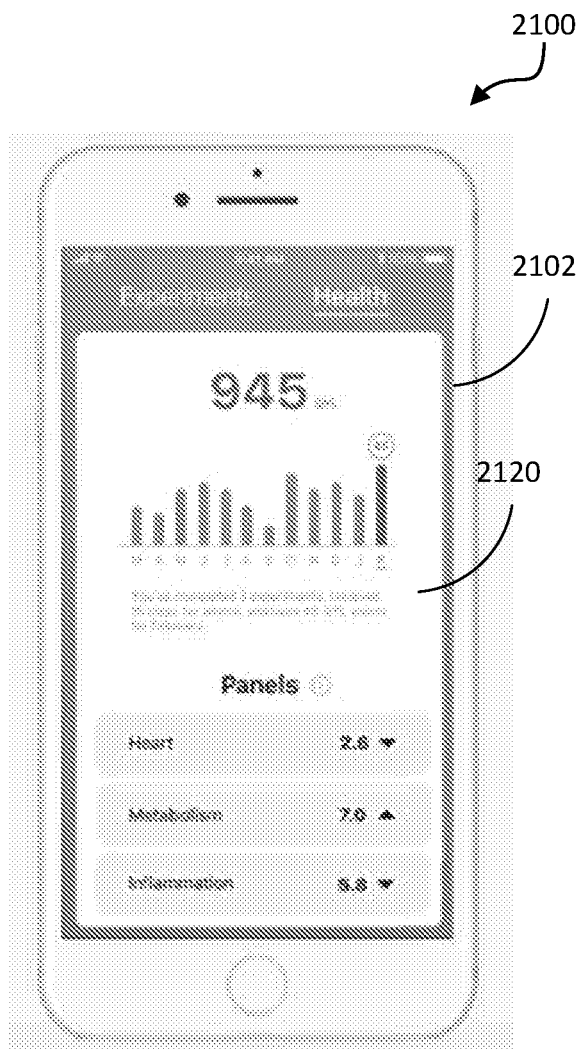

FIG. 33A shows an embodiment where the GUI 2102 of the user device 2100 provides encouragement to the user. In this example, the computing device may calculate the results 2116 of the beta glucan experiment informing the user that the experiment is working and the recommendation engine 420 may provide a message to the user device 2100 illustrating such and encouraging the user to continue with the experiment. The recommendation engine 420 may also provide nutritional information 2118 pertaining to the experiment and/or other foods/edible substances that the user should consume. The recommendation engine 420 may also provide information pertaining to missing experiments. In this example, the GUI 2102 illustrates a message stating that the user is missing an inflammation experiment. FIG. 33B shows other results 2120 (e.g., heart condition, metabolism, inflammation, and the like) that the recommendation engine 420 conveys to the user device 2100 for display on the GUI 2102.

Figure 34A:
Figure 34B:
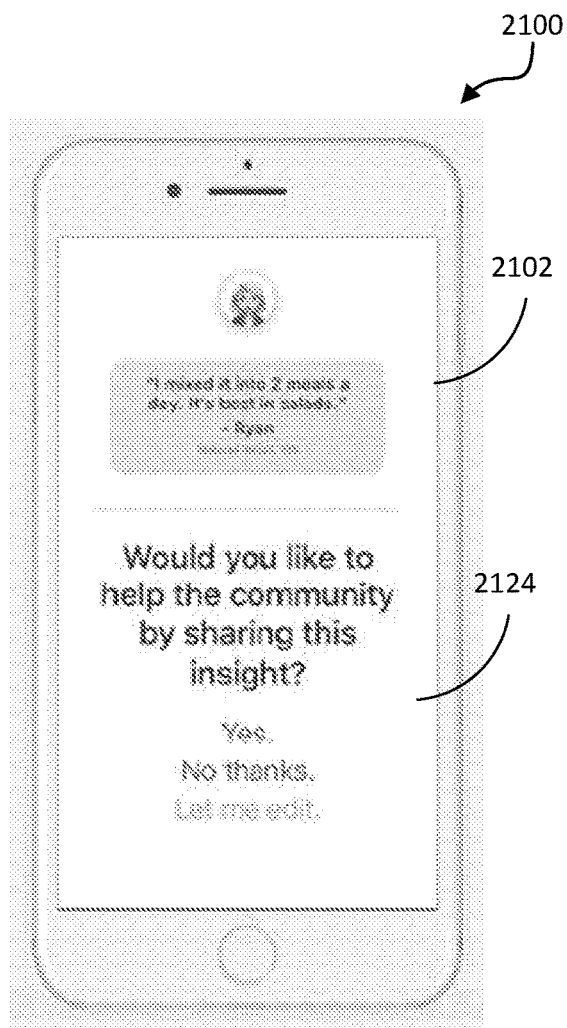

In some embodiments, the computing device may provide an interactive service between the user and the computing device. FIG. 34A illustrates the GUI 2102 of the user device 2100 with a message 2122 from the computing device querying the user for aids that assisted the user in a particular experiment. With this message, the computing device may provide a messaging field (e.g., short messaging service or "SMS") through which the user can reply. The computing device may convey this information to a service representative and/or automatically parse words from the message of the user to select an appropriate response 2124 as shown in FIG. 34B. For example, the computing device may query the user as to whether the user would like to share the user's insights and tips that assisted the user in performing the walnut experiment. From there, the user may select an appropriate automatic reply.

Figure 35A:
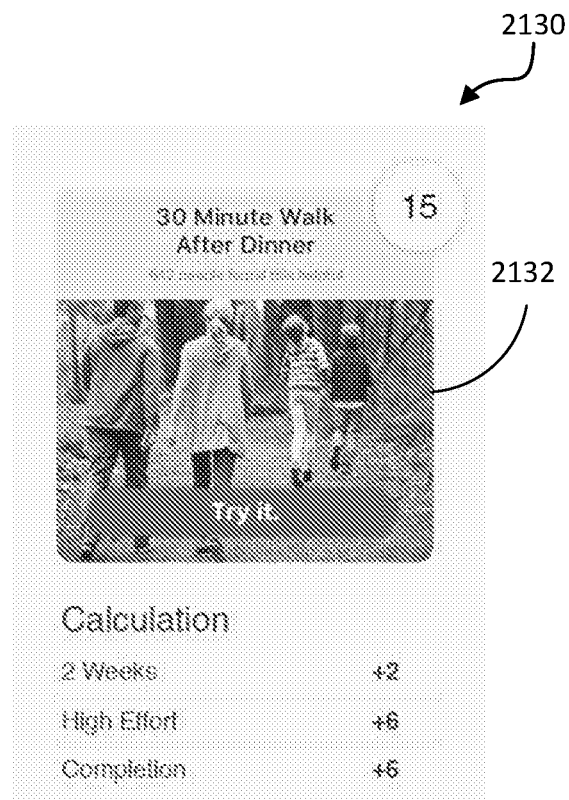
FIGS. 35 to 36 show exemplary messages displayed to a user via a graphical user interface, in accordance with some embodiments.
Figure 35B:
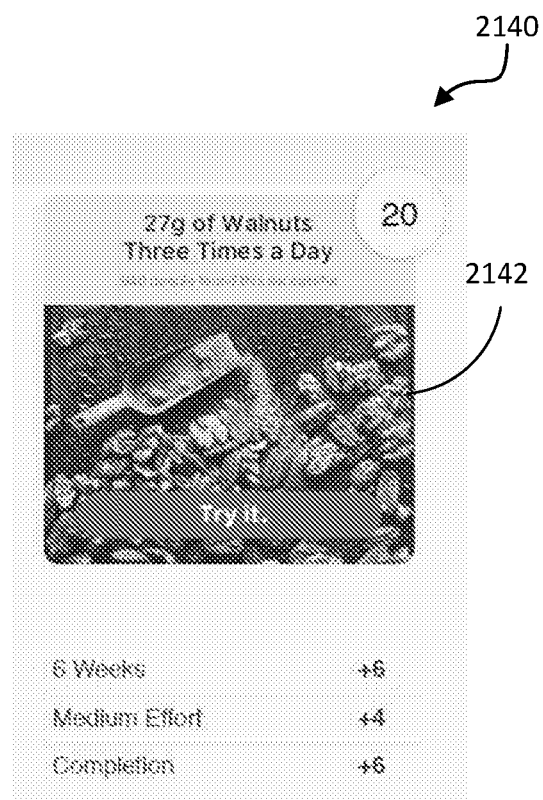
Figure 35C:
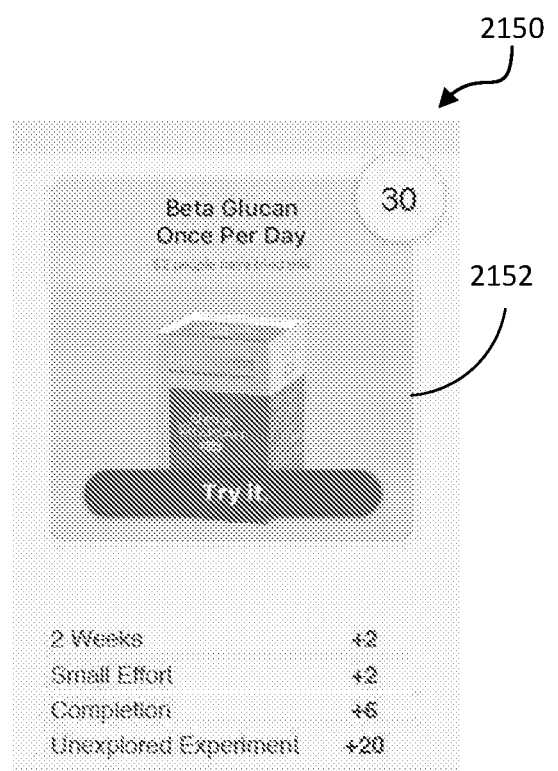

In some instances (e.g., where the user wishes to share information), the system 400 and its associated computing devices may implement a social networking platform. For example, if the user shares information to the network element 408, the network element 408 may share this information with other users communicating with the network element 408. In this regard, the network element 408 may compile statistics of other users and provide messages that may assist the user of the user device 2100. FIGS. 35A-35C shows various messages and information that may be displayed to the user illustrating experiments performed by other users. For example, message 2130 generated by the network element 408, in FIG. 35A, shows an experiment of a 30 minute walk after dinner that 642 people found helpful. Thus, the network element 408 may compile the information from the other users to deliver the message 2130 to the GUI 2102 of the user device 2100. And, in this message, the network element 408 may provide a link 2132 for the user of the user device 2100 to select. Such a selection may result in a message from the network element 408 to provide direction to the user to complete the experiment. FIG. 35B shows a similar message 2140 having the user consume 27 grams of walnuts three times a day with a selection link 2142. And, FIG. 35C shows a similar message 2150 having the user consume beta glucan once per day with a selection link 2152. Of course, these messages and the associated information may be implemented in a variety ways.

Figure 36A:
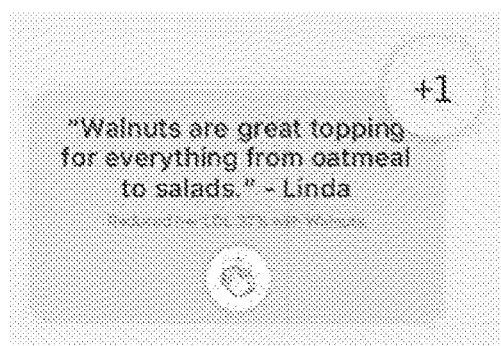
Figure 36B:
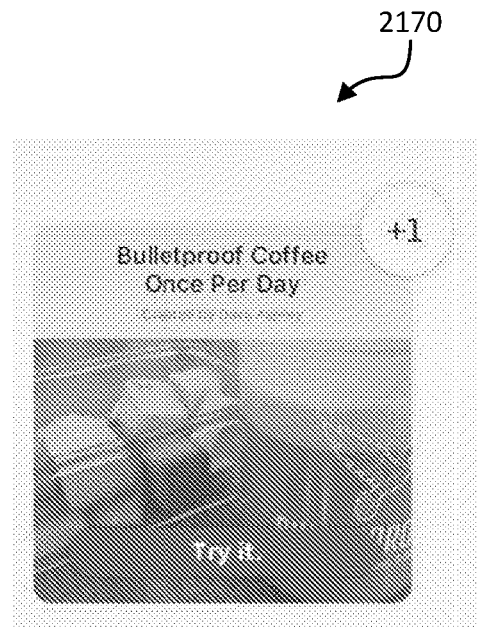

Additionally, other users may connect with the user of the user device 2100. For example, other users may send messages to the user of the user device 2100 through the social networking platform implemented by the system 400. In this regard, other users may send messages regarding certain results they had encountered during experiments, experiment recommendations, words of encouragement, and the like. FIG. 36A shows a message 2160 conveyed from another user to the user of the user device 2100 stating how walnuts of the walnut experiment may be preferably consumed. And, FIG. 36B shows a message 2170 from a user encouraging the user of the user device 2100 to consume a certain type of coffee. These messages and/or results from other users may be obtained from their individual blood spectroscopies of their experiments that have been conveyed to the network element 408. For example, other users connected to the network element 408 may perform experiments that are similar to those performed by the user of the user device 2100. These other users may derive results from their individual blood spectroscopies involved in those experiments such that the results of those blood spectroscopies may be conveyed to the network element 408 for storage within the database 410.

Figure 37:
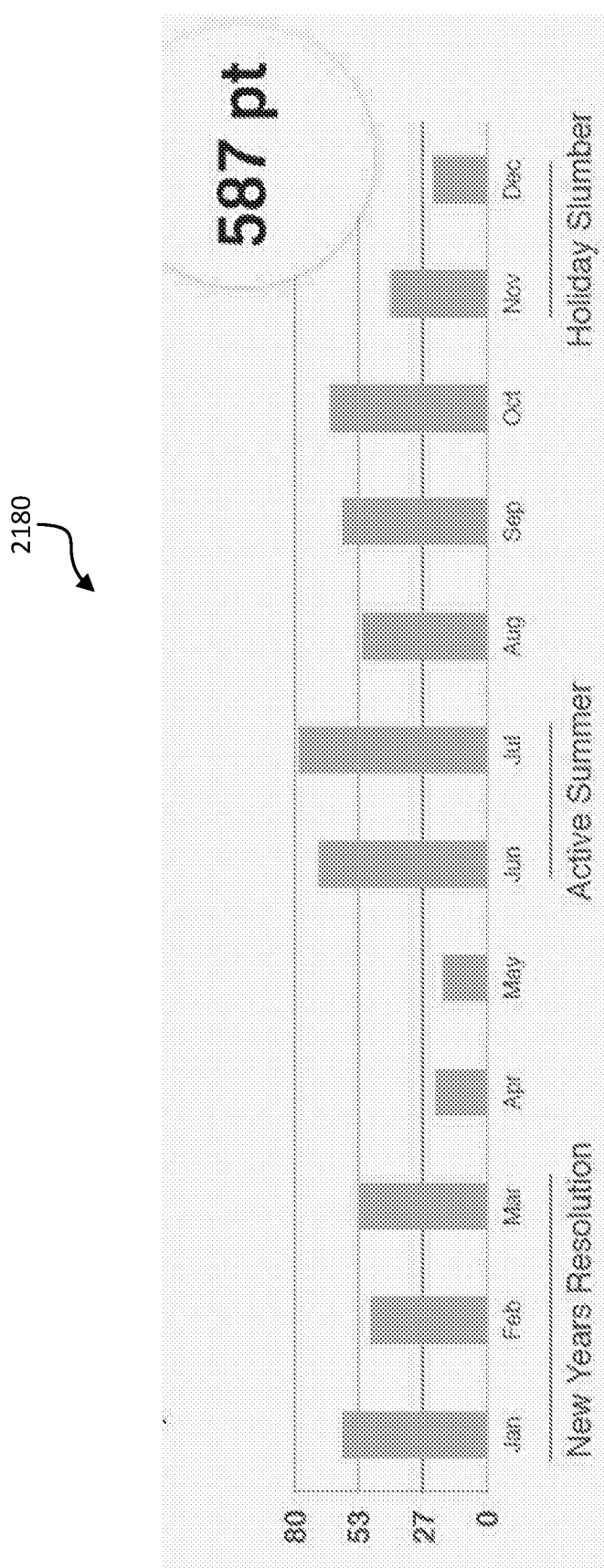
FIG. 37 shows an exemplary progress chart of a user displayed via a graphical user interface, in accordance with some embodiments.

FIG. 37 shows a graph 2180 of a user's progress over the course of a year, in one exemplary embodiment. In this embodiment, the network element 408 may compute a score for each month the user of the user device 2100 is engaging in experiments and attempting to improve the user's biomarkers through the experiments. Then, over the course the year, the network element 408 may compute an overall score for the user which may be shared with the user's social network. In this regard, the social media platform provided by the network element 408 may provide a means for competing between users in the user social network. For example, in this embodiment, the user of the user device 2100 has an overall score 587 points for the course of a year. Other users may have higher or lower scores and may encourage each other to obtain better scores and improve their overall health.

Figure 38:
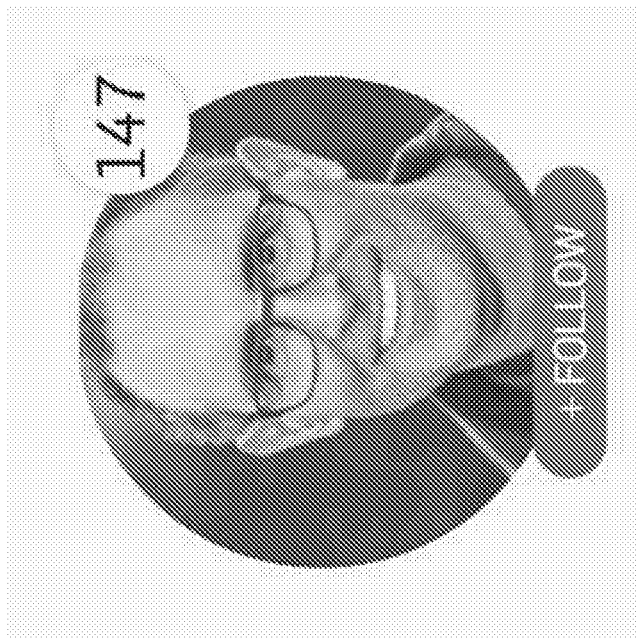
FIG. 38 shows an exemplary social networking platform, in accordance with some embodiments.

FIG. 38 shows an exemplary social networking aspect of the system 400. In this embodiment, the user 2190 has a network of 147 followers of which one may be the user of the user device 2100. In this regard, the user of the user device 2100 and the user 2190 may communicate with one another to encourage each other and/or share health information pertaining to their respective blood spectroscopies, experiments performed, health scores, and the like.

Figure 39:
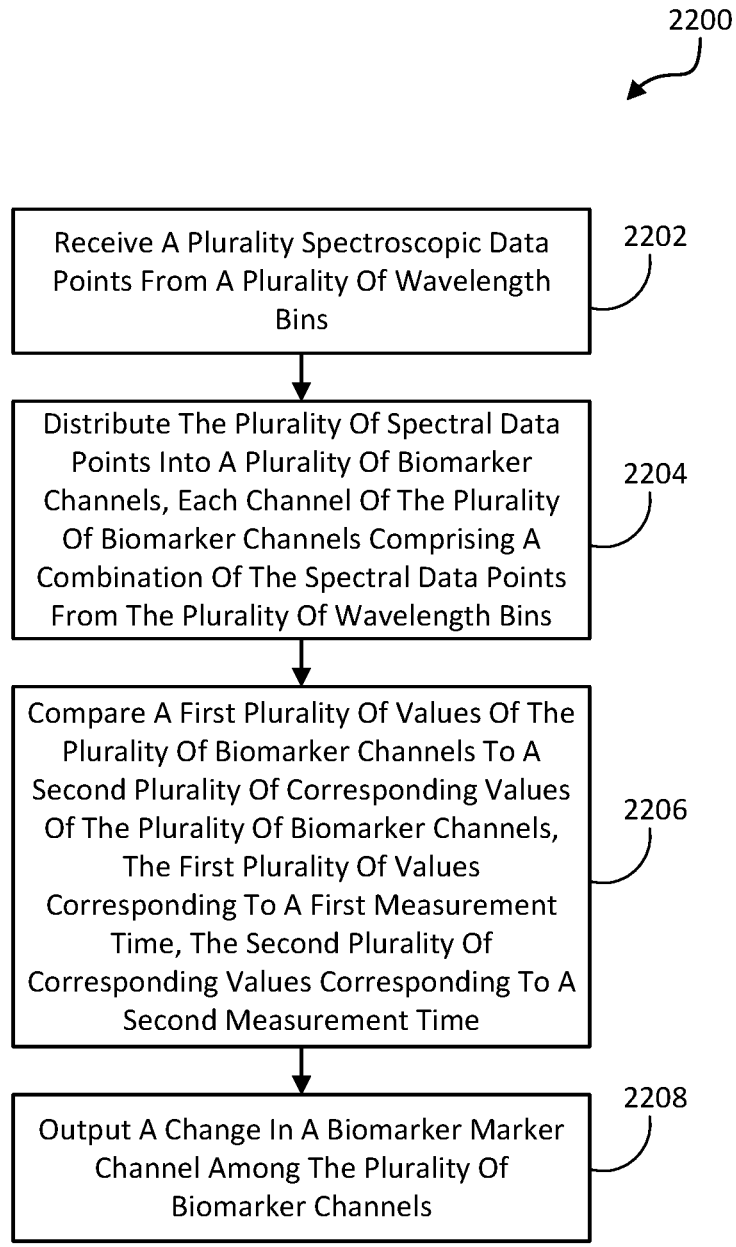
FIG. 39 shows a flowchart of an exemplary process, in accordance with some embodiments.

FIG. 39 shows a flowchart of an exemplary process 220, in accordance with some embodiments. In this embodiment, a computing device, such as the computing device 414 and/or the network element 408 of FIG. 27, is configured to receive a plurality of spectroscopic data points from a plurality of wavelength bins, in the process element 222. For example, the blood spectrometer 100 may generate spectral data pertaining to a user's blood sample. The blood spectrometer 100 may communicate that spectral data to the computing device for analysis. In this regard, the computing device may distribute the spectral data points into a plurality of biomarker channels, in the process element 224. Generally, each channel of the biomarker channels comprises a combination of the spectral data points from the plurality of wavelength bins.

The computing device may compare a first plurality of values of the biomarker channels to a second plurality of corresponding values of the biomarker channels, in the process element 226. Generally, the first plurality of values corresponds to a first measurement time and the second plurality of corresponding values corresponds to a second measurement time. Based on this information, the computing device may compute a change in at least one of the biomarker channels and output that change to the user device, in the process element 228.

The comparison of the biomarkers can have the benefit of showing how an experiment is changing the user's biomarkers, and these can be presented to the user as described herein. Although the amount of biomarker can be quantitative, the presently disclosed methods and apparatus can determine a change in a biomarker in response to a user experiment, which can provide useful information to the user.

Experiments can be conducted to show the accuracy of the measurements obtained with spectrometers and blood samples as described herein. The data can be analyzed chemometric methods and a N-fold "subject" out cross validation v. mean of all labs approach, and compared with reference samples obtained from the American College of Physicians. Chemometric methods can be used to define the biomarker channels based on weights combinations of spectral bins, such as Partial Least Squares ("PLS") regression, and Null Augmented Regression ("NAR"). The NAR may include PLS coupled with Tikhonov Regularization that leverages the constant-analyte spectra of within-sample measurements of the calibration data. Random Forest Regression Tree ("RF/RT") may also be employed.

Examples of suitable biomarkers and chemometric analysis suitable for determining biomarkers are described in PCT/US2016/026825, filed Apr. 8, 2016, entitled "METHOD AND APPARATUS FOR DETERMINING MARKERS OF HEALTH BY ANALYSIS OF BLOOD", the entire disclosure of which is incorporated herein by reference. Although many chemometric approaches can be used, in some embodiments, a genetic algorithm is used to determine an amount of biomarker for a given biomarker channel. A plurality of spectral bins can be combined with appropriate weighting of each of the spectral channels in order to an amount of a biomarker. For example, approximately 300 to 400 spectral bins can be combined to determine a parameter related to health such as blood pressure.

The methods and apparatus as described herein can be configured with instructions to provide augmentation of the calibration space. While the calibration space augmentation can be performed in one or more of many ways with the factors and functions methods as described herein, the calibration space augmentation may comprise one or more of an augmented classical least squares of the calibration space data, an augmented partial least square of the calibration space data, or a multivariate curve resolution of the calibration space data. An iterative fit can be performed to linearly independent spectral data sets, for example. A spectral signature can be developed for one or more of the calibration space data or the blood sample data, for example. The spectral signature of the calibration space data can be used for later analysis of the blood sample as described herein, for example with one or more of partial least squares, augmented classical least squares, multivariate curve resolution, or other chemometric approach as described herein, for example.

Figure 40:
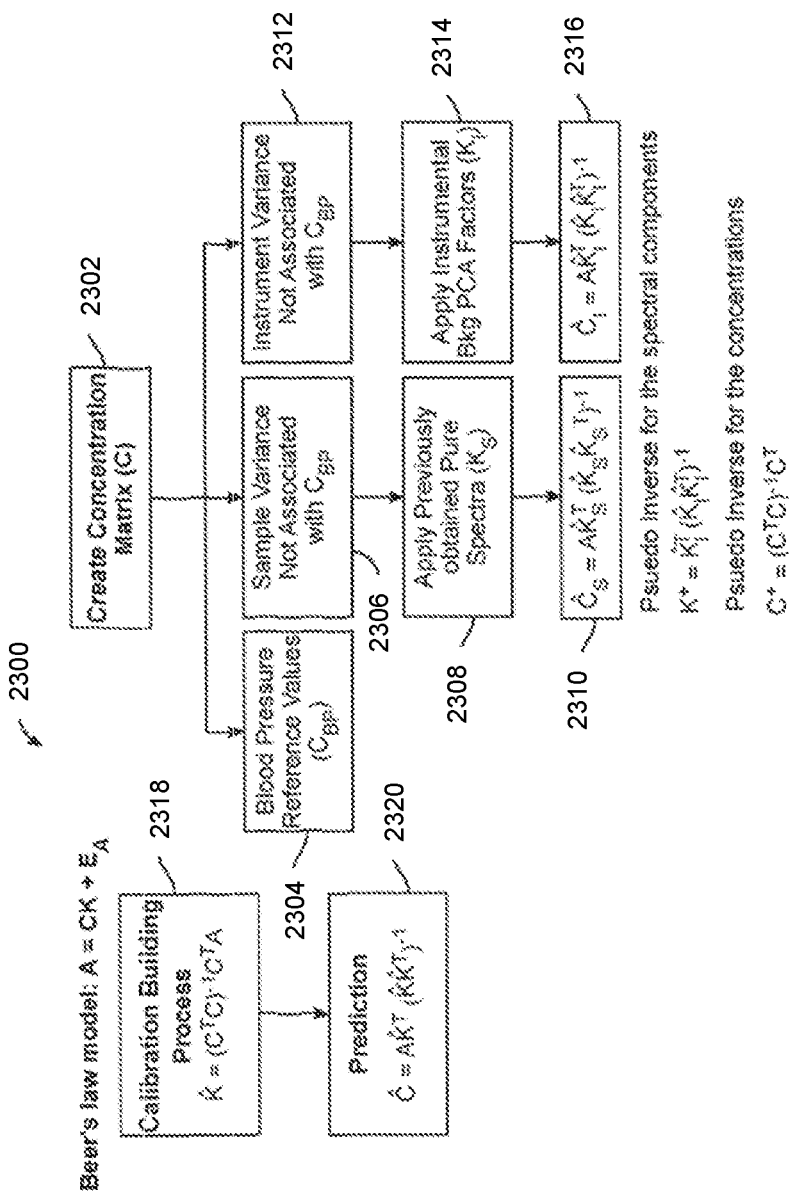
FIG. 40 shows a method of spectral data analysis suitable for incorporation with some of embodiments.

FIG. 40 shows a method 2300 of spectral data analysis suitable for incorporation with embodiments as disclosed herein. The analysis of spectral channels can be configured in many ways to determine the spectral bins that can be used to define a channel of a marker such as a biomarker.

The marker and biomarker channels as disclosed herein can be determined in many ways, and the following is provided as an example of a blood pressure channel suitable for incorporation with embodiments as disclosed herein. The approach described with reference to FIG. 40 is similar to the one described in PCT/US2016/026825, filed Apr. 8, 2016, entitled "METHOD AND APPARATUS FOR DETERMINING MARKERS OF HEALTH BY ANALYSIS OF BLOOD", the full disclosure of which has been previously incorporated by reference.

A variant of Classical Least Squares (CLS) may be used to build calibration models and predict blood pressure values or other markers as described herein based on red blood cell spectra. This CLS variant has been referred to as Augmented CLS and can often be performed during the prediction process. CLS assumes Beer's law behavior ($A=CK+E_A$), where A is the absorbance spectra, C is a matrix of concentrations, K is the pure component spectra and EA are the spectral residuals (anything unmodelled by linear combination of C and K). Red blood cell spectra obtained using a measurement apparatus as described herein can be converted to absorbance by taking the minus Log10 of the ratio of the red blood cell spectra to a close-in-time instrumental background spectrum. Since CLS tries to minimize $E_A$, all sources of spectral variation need to be modelled through the concentrations (C) and the pure component spectra (K) in order to produce accurate resultant estimates. The pure component spectrum (K) of an analyte of interest is usually already known; therefore augmentation usually occurs in the prediction process (solving for C). To prevent aberrant spectral variation (spectral variation not associated with the analyte of interest) from affecting the CLS model, the model may be proactively augmented with spectral component(s) associated with these aberrations, so that better concentration estimates of the analyte of interest can be obtained. The augmentation process may be applied during the calibration process, in order to get an accurate estimate of the spectral pure component associated with blood pressure.

At step 2302, a concentration matrix C is created to obtain the pure spectral component of blood pressure or other marker as disclosed herein. This concentration matrix can be composed of blood pressure reference measurements (CBp), concentrations associated spectral variance during the measurement of the red blood cell samples but not associated with the red blood cells (Cs), and concentrations associated with spectral variance of the instrument (Ci). Concentrations CBP, CS, and Ci can be combined into one concentration matrix C, and used to estimate the pure spectral components that can be used for later predictions.

At step 2304, the blood pressure reference values (CBP) or other marker as disclosed herein are obtained. The blood pressure reference values CBP may comprise the mean of the blood pressures acquired over a period of time from a subject, to ensure the best estimate of the actual sustained blood pressures from the subject.

At step 2306, the concentrations associated with spectral variance during the measurement of the red blood cell samples (Cs) are obtained.

At step 2308, previously obtained pure spectral components (Ks) are applied. Spectral components Ks may comprise spectral components of water, red blood cells, and spectral variation associated with a process applied to the red blood cells, such as gravimetric separation as disclosed herein.

At step 2310, the concentrations Cs are estimated using CLS, from the pseudo inverse of the previously obtained pure spectral components Ks and the absorbance spectra A. The pseudo inverse $K^+$ of the spectral components Ks can be obtained using the equation $K = K_s(K_sK_s)"$, where $K_s$ is the transpose of the matrix $K_s$.

At step 2312, the concentrations associated with the instrument variation (Ci) are obtained.

At step 2314, instrumental background spectra (Bkg) are applied. Background spectra Bkg may be taken during the entire period of absorbance spectra (A) data collection. These background spectra can comprise measurements of air (no sample in sample compartment of instrument), or measurements of a sample that most spectrally resembles the sample of interest, but is not the actual sample of interest (e.g., water or saline). These background spectra can be decomposed into spectral factors or components (¾) by using Principal Component Analysis (PCA). The number of these spectral components (¾) can be varied, such that only the largest sources of spectral variance are explained by these spectral components (¾).

At step 2316, the concentrations associated with the instrument variation Ci are estimated using CLS, from the pseudo inverse of the instrument variation spectral components Ki and the absorbance spectra A. The pseudo inverse $K^+$ of the spectral components ¾ can be obtained using the equation $K^+ = K_i^t (K_t K_i)^1$, where $K_t$ is the transpose the matrix $K_t$.

At step 2318, the calibration model is built by using a CLS calculation to obtain the pure component spectra K of which the component of interest resides, from the pseudo inverse of the concentration matrix C and absorbance spectra. The pseudo inverse $C^+$ of the concentrations C can be obtained using the equation $C^+ = (C^T C)^{-1} C^T$, where $C^T$ is the transpose the matrix C. The spectral component of interest can be, for example, the component associated with blood pressure or other marker as disclosed herein.

At step 2320, the concentration C of the component of interest is predicted using traditional CLS, from the pseudo inverse of the pure component spectra K and the absorbance spectra A. The pseudo inverse $K^+$ of the spectral components K can be obtained using the equation $K^+ = K^T (KK^T)^{-1}$, where $K^T$ is the transpose of the matrix K. The concentration C can be, for example, the blood pressure level or other marker level as disclosed herein. Using this prediction model, blood pressure or other marker as disclosed herein may be predicted using spectral data of blood samples acquired in the future by using traditional or augmented CLS methods.

The method 2300 discloses a method of predicting blood pressure from spectroscopic data from blood samples, in accordance with some embodiments. A person of ordinary skill in the art will recognize many variations and modifications based on the disclosure provided herein. For example, some steps may be modified, some steps may be added or removed, some of the steps may comprise substeps, and many of the steps can be repeated.

The processor as described herein can be programmed with one or more instructions to perform one or more of the steps of the method 2300 of predicting blood pressure or other marker as disclosed herein using blood spectroscopic measurements. Therefore, the above steps are provided as an example of a method of measuring blood pressure of the subject in accordance with embodiments.

The methods of sample measurement and analysis as described herein may be optimized using computational algorithms. For example, one or more steps of the methods described herein involving the selection of a parameter may be optimized using a genetic algorithm. A genetic algorithm generally comprises a family of evolutionary search procedures that are based upon mechanisms of natural selection and genetics. A genetic algorithm may apply principles of survival of the fittest to solve general optimization problems.

A genetic algorithm may be used to optimize one or more steps of spectral data analysis as described herein. For example, a genetic algorithm may be applied to select a subset of wavelengths or frequencies of sample spectra to use in generating a calibration model to predict blood pressure or other marker as disclosed herein from red blood cell spectra. A sample spectrum usually comprises a plurality of measurements at a plurality of frequencies, wherein the plurality may comprise hundreds or thousands of data points. Therefore, selecting a subset of frequencies that are most relevant for predicting blood pressure (or other marker as disclosed herein) in building the calibration model can enhance the accuracy or predictiveness of the generated calibration model, as well as reduce the computational burden in building the calibration model and generating predictions.

Figure 41:
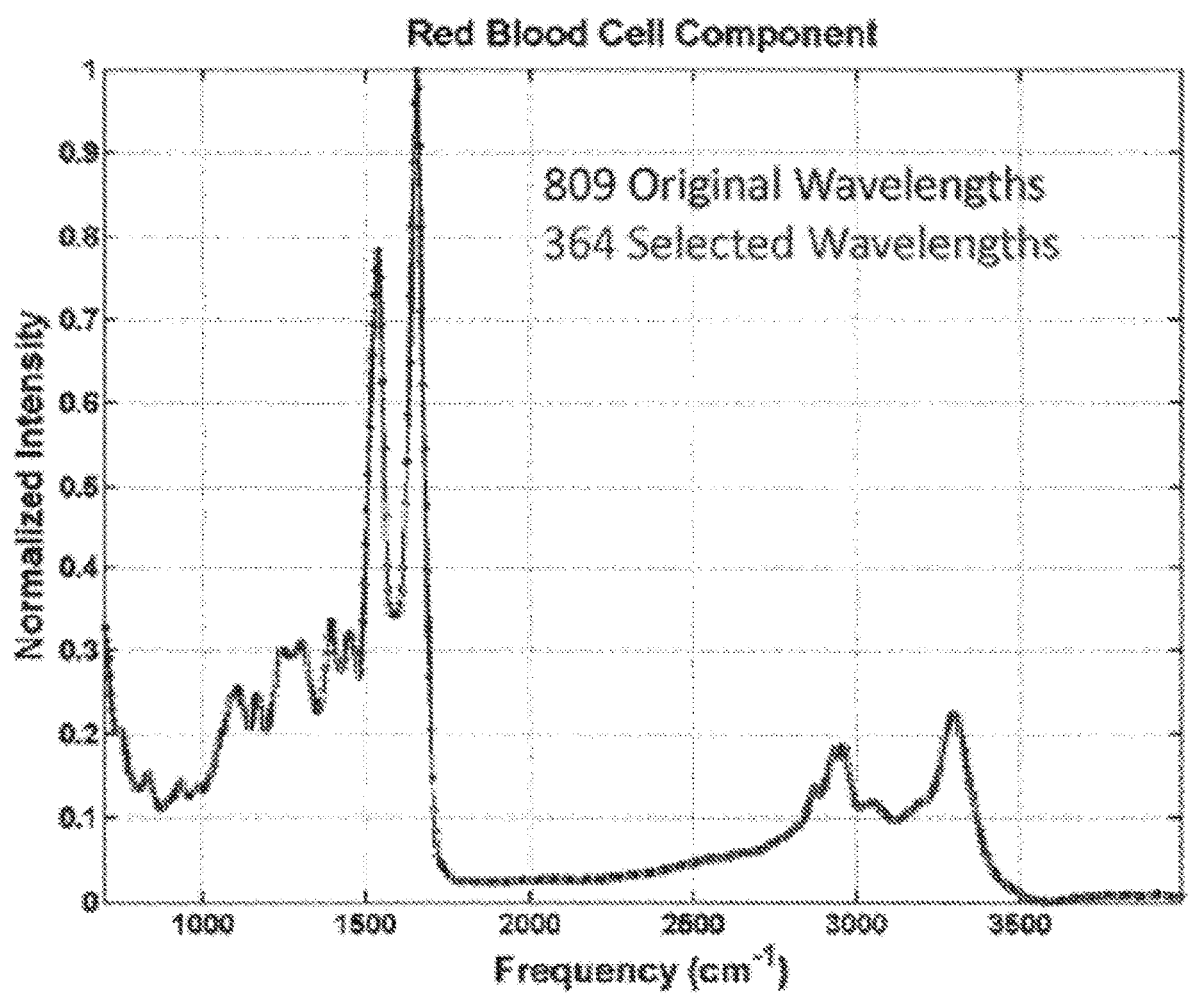
FIG. 41 shows the final selection of wavelengths of a red blood cell spectrum, optimized using a genetic algorithm procedure, in accordance with some embodiments.

FIG. 41 shows the final selection of wavelengths of a red blood cell spectrum, optimized using a genetic algorithm procedure for a marker such as blood pressure, suitable for incorporation with the present disclosure. The original spectrum contained data points at 809 wavelength bands or frequencies. Using the genetic algorithm, 364 wavelengths were selected to be used in building the calibration model and generation predicted blood pressures from the calibration model. The 364 selected wavelength bands were identified from generation 19 wavelength strings. Some of the wavelength bands most consistently identified as important for the prediction of blood pressure included wavelengths of about 1950 to about 2000 $cm^{-1}$, which can contain a transition metal carbonyl band potentially indicative of the formation of a spectrin-hemoglobin complex, linked to the rigidity of the red blood cell membrane.

The measured spectral intensities of the 364 discrete wavelength bands can be combined with appropriate weighting of the genetic algorithm to define a blood pressure channel. In accordance with the present disclosure, changes to the blood pressure channel can be measured in response to a lifestyle or other change, and the change presented to a user or other users as disclosed herein.

Although FIG. 41 shows wavelength bands suitable for determining a blood pressure marker, the approach for determining a blood pressure channel can be used for any of the markers and biomarkers as disclosed herein. A person of ordinary skill in the art can conduct similar experiments do determine the appropriate combinations and weights for the measured wavelengths bands to define a channel for a specific marker as disclosed herein. The changes in the channel can be monitored as disclosed herein.

This disclosure also includes the following numbered clauses:

Clause 1: An apparatus, comprising:

a spectrometer configured to receive a sample of blood contained within a sample holder, to illuminate the sample of blood as the blood at least partially separates within the sample holder; and a processor operatively coupled to the spectrometer, the processor configured with instructions to generate spectral data of the sample at a plurality of wavelengths and a plurality of times corresponding to at least partial separation of the sample of blood into a plurality of components of the sample.

Clause 2: The apparatus of claim 1, wherein the processor is configured with instructions to measure two of more of a high density lipoprotein, a total cholesterol, a triglyceride or a glucose of the sample with a cross-validated standard errors of prediction ("CVSEP") of no more than 12 mg/dL, 20 mg/dL, 40 mg/dL, 20 mg/dL, respectively, for each of the two of more of the high density lipoprotein, the total cholesterol, the triglyceride or the glucose of the sample, with the spectral data from the plurality of times corresponding to the at least partial separation.

Clause 3: The apparatus of clause 2, wherein the two or more comprises three or more of the total cholesterol, the triglyceride or the glucose of the sample with the cross-validated standard errors of prediction of no more than 12 mg/dL, 20 mg/dL, 40 mg/dL, 20 mg/dL and optionally wherein the three or more comprises four or more.

Clause 4: The apparatus of clause 1, wherein the spectral data comprises spatially resolved spectral data acquired at the plurality of times.

Clause 5: The apparatus of clause 1, wherein the processor is configured with instructions to measure the sample at the plurality of times within a range from about 5 minutes to about 3 hours while the sample separates and optionally within a range from about 30 minutes to about 2.5 hours and optionally within a range from about 1 hour to about 2 hours.

Clause 6: The apparatus of clause 1, wherein the processor is configured with instruction to obtain a plurality of measurements with an interval of approximately 30 seconds to 10 minutes between each of the plurality of measurements and optionally wherein the sample has at least partially separated during the plurality of measurements.

Clause 7: The apparatus of clause 1, wherein the sample holder is configured to provide reagentless whole blood spectroscopy.

Clause 8: The apparatus of clause 1, wherein a volume of the sample holder is within a range from about 0.25 microliters to about 4 microliters and optionally wherein a volume of the sample holder is within a range from about 0.5 to about 2 microliter.

Clause 9: The apparatus of clause 1, wherein the processor is configured with instructions to take substantially continuous scans of the sample with a duty cycle within a range from about 10% to about 90% of a light source illuminating a detector of the spectrometer.

Clause 10: The apparatus of clause 1, wherein spectrometer comprises:
a broad spectrum light source to generate a plurality of wavelengths of light;
a detector;
a wavelength selector coupled to the broad spectrum light source to selectively direct light toward the detector with the sample located between the wavelength selector and the detector, wherein the wavelength selector comprises one or more of a dispersive element, a prism, a grating, a diffractive optic, an interferometer, a Michelson interferometer, digital micromechanical mirror, or an Etalon.

Clause 11: The apparatus of clause 10, wherein the detector comprises a indium gallium arsenide (InGaAs) detector and optionally wherein the detector comprises a single element detector.

Clause 12: The apparatus of clause 1, wherein spectrometer comprises a receptacle to receive the sample holder with the blood contained therein with an elongate axis of the sample holder oriented toward a vertical angle of inclination to separate the blood.

Clause 13: The apparatus of clause 12, wherein the sample holder comprises a blood collector, the blood collector comprising a housing and a lancet, the receptacle configured to receive the housing with the lancet positioned at least partially in a channel of the sample holder with the blood sample.

Clause 14: The apparatus of clause 1, wherein a height of a window in the sample holder is within a range from about 1 mm to about 20 mm and optionally within a range from about 2 mm to about 10 mm.

Clause 15: The apparatus of clause 1, wherein a number of spatially resolved sample locations along a height of the sample is within a range from about 2 to about 1000 and optionally within a range from about 5 to about 100.

Clause 16: The apparatus of clause 1, wherein the plurality of wavelengths corresponds to a plurality of discretely resolved wavelength bands within a range from about 25 to about 1000 discretely resolved wavelength bands and the plurality of times is within a range from about 2 to about 1000 and optionally wherein the plurality of discretely resolved wavelength bands is within a range from about 50 to about 200 and the plurality of times is within a range from about 50 to about 100.

Clause 17: The apparatus of clause 16, wherein the plurality of discretely resolved wavelength bands comprises a plurality of wavelength bands within a range from about 1500 nm to about 2000 nm and optionally within a range from about 1400 nm to 2400 nm.

Clause 18: The apparatus of clause 1, wherein the spectrometer comprises a maximum dimension of 170 mm and optionally wherein the spectrometer comprises a length of no more that about 170 mm, a width of no more than about 75 mm, and a height of no more than about 100 mm and optionally wherein the spectrometer comprises a length within a range from about 80 to about 170 mm, a width within a range from about 30 to about 75 mm and a height within a range from about 50 to about 100 mm and optionally wherein the spectrometer comprises a volume within a range from about 120,000 mm3 (0.12 liter) to about 1,275,000 mm3 (1.275 liter).

Clause 19: The apparatus of clause 1, further comprising a digital micromirror device (DMD), wherein the sample of blood is located between the DMD and a detector.

Clause 20: The apparatus of clause 19, wherein the sample of blood is located within about 10 mm of the detector.

Clause 21: The apparatus of clause 19, wherein the processor is coupled to the DMD, wherein the processor is configured to select a region of the sample of blood, and to direct light from the region to the detector.

Clause 22: The apparatus of clause 21, wherein:
the sample holder is configured to orient the sample of blood along a column, and to separate the blood along the column; and
the DMD and the processor are configured to selectively scan light from a plurality of regions of the sample of blood to the detector Clause 23: The apparatus of clause 22, wherein:
the processor comprises instructions to sequentially configure the DMD in accordance with a plurality of Hadamard encodements.

Clause 24: The apparatus of clause 22, wherein:
the sample holder comprises an elongate channel;

the spectrometer is configured to receive the sample holder and align the elongate channel of the sample holder along a substantially vertical direction to separate the blood into the plurality of components along the elongate channel; and the substantially vertical direction comprises an angle within about 20 degrees of vertical.

Clause 25: The apparatus of clause 24, wherein:

the DMD and the processor are configured to selectively scan a first region of the sample holder comprising a first component, and to selectively scan a second region of the sample holder comprising a second component;

the processor is configured with instructions to determine an amount of time for the sample to separate into the first and second components;

the first component comprises blood plasma; and the second component comprises hematocrit.

Clause 26: The apparatus of clause 19, further comprising collection optics, wherein the detector is configured proximate to the collection optics to capture light from the illuminated sample of blood.

Clause 27: The apparatus of clause 26, wherein:

the collection optics comprise a focusing element; and the detector comprises an Indium Gallium Arsenide (InGaAs) detector configured near a focal length of the collection optics and optionally wherein a surface the detector is located within +/−25% of the focal length of the collection optics.

Clause 28: The apparatus of clause 1, wherein the sample holder comprises an elongate container comprising an elongate axis to separate the sample of blood into the plurality of components.

Clause 29: The apparatus of clause 1, wherein the sample holder comprises a substantially transparent tube configured to separate the sample of blood into the plurality of components.

Clause 30: The apparatus of clause 29, wherein the substantially transparent tube comprises a capillary tube.

Clause 31: The apparatus of clause 30, wherein the sample holder comprises a slit aperture configured to direct light through the substantially transparent tube.

Clause 32: The apparatus of clause 1, wherein the sample holder is configured to provide reagentless whole blood spectroscopy and wherein a volume of the sample holder is within a range from about 0.25 microliters to about 4 microliters and optionally wherein the volume of the sample holder is within a range from about 0.5 to about 2 microliter.

Clause 33: The apparatus of clause 1, wherein the processor is configured with instructions to take substantially continuous scans of the sample with a duty cycle within a range from about 10% to about 90% of a light source illuminating a detector of the spectrometer.

Clause 34: The apparatus of clause 1, wherein the sample holder comprises a needle configured to draw blood from a user into the substantially transparent tube and optionally wherein a volume of the sample holder is within a range from about 0.5 to about 2.0 microliter.

Clause 35: The apparatus of clause 34, wherein the sample holder further comprises a spring configured to plunge the needle into the user a predetermined depth, and to withdraw the needle after plunging the needle into the user.

Clause 36: The apparatus of clause 1 further comprising a network interface configured to communicate the wavelength spectral data to a network.

Clause 37: The apparatus of clause 36, wherein the network interface is further configured to communicate the wavelength spectral data to a user device.

Clause 38: The apparatus of clause 1, wherein the processor is configured with instructions to measure one or more of:

a hormone, the hormone comprising one or more of dehydroepiandrosterone ("DHEA"), Testosterone, Growth Hormone, Parathyroid Hormone, Estradiol, Progesterone, or Cortisol;

a health and performance marker, the health and performance marker comprising one or more of Vitamin B12, PSA, Thyrogobulin, Troponin, IGF-1, Aldosterone, Prolactin, Creatine Kinase, Ferritin, Selenium, Homocystine, Copper, Ammonia, Folic Acid, AGE, or Cortisol;

a metabolic marker, the metabolic marker comprising one or of Glucose, HbA1c, Glycated Albumin, Insulin Resistance, Ketones, β-Hydroxybutyrate, Albumin, Total protein, BUN, Uric acid, Glutamate, GSH, Lactic Acid, CO2, pH, or Hydration;

an immunology, inflammation and hematology marker comprising one or more of Fibrinogen, hsCRP, Globulins, Hematocrit, Hemoglobin, Erythrocyte sedimentation rate, Glutathione, Uric acid, Serum Amyloid A, Haptoglobin, WBC Count estimate, Transferrin saturation, Pyruvate, RBC count estimate, Platelet count estimate, Prothrombin time/INR, Interleukin-6;

a cardiovascular marker comprising one or more of Cardiovascular total Cholesterol, HDL, LDL, VLDL, non-HDL, Lipid Ratio, Triglycerides, BNP, Apolipoprotein, or Average Blood Pressure; or a marker of stress and toxins, the marker of stress and toxins comprising one or more of oxidized LDL (oxLDL), Erythrocyte Glutathione Peroxidase, Cortisol, Creatinine, Albumin, Carboxyhemoglobin, Ethanol, Carbon monoxide, Salicylates, Acetaminophen, or Caffeine.

Clause 39: A method, comprising:

placing a sample of blood contained within a sample holder in a receptacle of a spectrometer;

illuminating the sample of blood as the blood separates within the sample holder; and generating spectral data of the sample at a plurality of wavelengths and a plurality of times corresponding to at least a partial separation of the blood into a plurality of components of the sample.

Clause 40: The method of clause 39, wherein one or more of the container comprises an anticoagulant prior to placing the blood sample in the sample holder.

Clause 41: The method of clause 39, wherein the blood sample comprises an anticoagulant when illuminated.

Clause 42: The method of clause 39, comprising:

identifying the components of the blood based on their corresponding spectral data.

Clause 43: A tangible medium configured with instructions for:

receiving a plurality spectroscopic data points from a plurality of wavelength bins;

distributing the plurality of spectral data points into a plurality of marker channels, each channel of the plurality of marker channels comprising a combination of the spectral data points from the plurality of wavelength bins;

comparing a first plurality of values of the plurality of marker channels to a second plurality of corresponding values of the plurality of marker channels, the first plurality of values corresponding to a first measurement time, the second plurality of corresponding values corresponding to a second measurement time; and outputting a change in a biomarker marker channel among the plurality of marker channels to a user device.

Clause 44: The tangible medium of clause 43, wherein comparing the plurality of channels comprises comparing each value of the first plurality of values to a corresponding value of the second plurality of values.

Clause 45: The tangible medium of clause 43, wherein the plurality of channels comprises a vector, each value of the vector corresponding to a combination of the plurality of wavelength bins.

Clause 46: The tangible medium of clause 43, wherein the plurality of wavelength bins comprises wavelength bins spaced apart with non-overlapping wavelengths and wherein values of the plurality of channels are determined based on the plurality of wavelength bins comprising non-overlapping wavelengths.

Clause 47: The tangible medium of clause 43, wherein a change in each of the plurality of combination values from the first time to the second time is determined based on a change from the first time to the second time of said each of the plurality of channels.

Clause 48: The tangible medium of clause 43, wherein each of the plurality of channels comprises a weighted combination of spectral data from the plurality of wavelength bins.

Clause 49: The tangible medium of clause 43, wherein the plurality of wavelength bins comprises at least about 50 wavelength bins and wherein each of the plurality of channels comprises a combination values of the at least about 50 discrete wavelength bins.

Clause 50: The tangible medium of clause 43, wherein a portion of the plurality of channels consists of a same wavelength bin, and each channel of the portion comprises a different combination of the same wavelength bin.

Clause 51: A method comprising:
receiving a plurality of spectroscopic data points, wherein the plurality of spectroscopic data points comprises spectrometer data of samples taken over a time interval and the spectrometer data comprises intensities from a plurality of wavelength bins;
distributing the plurality of spectroscopic data points into a plurality of channels based on the plurality of wavelength bins, wherein each of the plurality of wavelength bins is associated with one or more of the plurality of channels and each of the plurality of channels comprises a combination of spectral measurement values from the plurality of wavelength bins; and
analyzing the plurality of channels for each channel of the plurality of channels to detect a significant change in one or more of the plurality of channels over the time interval.

Clause 52: The method of clause 51, further comprising monitoring a channel among the plurality of channels for a change in the channel.

Clause 53: The method of clause 52, wherein monitoring the channel for the change in the channel comprises:
combining first measurement data from the plurality of wavelength bins associated with the channel from a first measurement to generate a first value of the channel; and
combining second measurement data from the plurality of spectral channels associated with the channel from a first measurement to generate a second value of the measurement channel;
comparing the first value of the measurement channel with the second value of the measurement channel to determine the change in the measurement channel.

Clause 54: The method of clause 51, wherein distributing the plurality of spectroscopic data points comprises:
distributing the plurality of spectroscopic data points into the plurality of channels, wherein a value of the channel for each channel corresponds to intensity values of associated wavelength bins.

Clause 55: The method of clause 51, wherein analyzing the plurality of channels comprises:
identifying for each channel of the plurality of channels an amount of change over the time interval.

Clause 56: The method of clause 51, wherein analyzing the plurality of channels comprises:
generating a first value for each of the plurality of channels from first spectral data of the plurality of wavelength bins;
generating a second value for each of the plurality of channels from second spectral data of the plurality of wavelength bins;
determining a difference between the first value and the second value for each of the plurality of channels; and
detecting the significant change based on the difference above a threshold for one or more of said each of the plurality of channels.

Clause 57: The method of clause 56, wherein the first values of the plurality of channels comprise control values.

Clause 58: The method of clause 51, wherein the plurality of spectroscopic data points corresponds to periodic blood samples taken over the time interval and measured by a spectrometer as part of a health experiment.

Clause 59: The method of clause 58, wherein the periodic blood samples correspond to a plurality of users.

Clause 60: The method of clause 59, wherein the time interval corresponds to a period of time during which each of the plurality of users implement a lifestyle change as part of the health experiment Clause 61: The method of clause 58, wherein the spectrometer is configured for reagentless whole blood spectroscopy.

Clause 62: The method of clause 51, wherein the spectral datapoints comprise spectral measurements from a whole blood sample and optionally wherein the time interval corresponds to a first a spectral measurement of a first blood sample and a second spectral measurement of a second blood sample.

Clause 63: The method of clause 51, wherein the plurality of channels corresponds to at least 200 resolved wavelength bins and the plurality of channels comprises at least 8 channels.

Clause 64: A method comprising:
presenting at least one lifestyle change experiment to a user via a graphical user interface of a user device;
receiving a selection of an experiment in a computing device;
prompting, from the computing device and based on the selected experiment, a reminder to the user to perform a lifestyle change in accordance with the experiment;
prompting, from the computing device, the user to take a blood sample;
processing, in the computing device, spectroscopic data corresponding to the blood sample; and
presenting results of the selected experiment based at least on the received spectroscopic data via the graphical user interface of the user device.

Clause 65: The method of clause 64, wherein the experiment comprises one or more of a metabolism experiment, a cardiovascular health experiment, an inflammation and immune function experiment, hematologic function experiment, a toxin experiment, a stress experiment, a saliva experiment, or a fecal fat experiment.

Clause 66: The method of clause 65, wherein the metabolism experiment detects a change in one or more of the following channels: glucose, HbA1c (Glycated Hemoglobin), glycated albumin, ketones, β-hydroxybutyrate, albumin, total protein, blood urea nitrogen (BUN), uric acid, creatinine, glutamate, lactic acid (lactate), CO2 (bicarbonate), pH, sodium, magnesium, potassium, calcium, hydration, total body water (TBW), hematocrit, vitamin E, vitamin C, or vitamin A.

Clause 67: The method of clause 65, wherein the cardiovascular experiment detects a change in one or more of the following channels: high density lipoprotein (HDL), low density lipoprotein (LDL), total cholesterol and other cholesterol ratios, apolipoprotein, triglycerides, or average blood pressure.

Clause 68: The method of clause 65, wherein the inflammation experiment detects a change in one or more of the following channels: fibrinogen, C-reactive protein (CRP), uric acid, serum amyloid, globulins, IgG, IgA, IgM, or haptoglobin.

Clause 69: The method of clause 65, wherein the hematology experiment detects a change in one or more of the following channels: hematocrit, hemoglobin, erythrocyte sedimentation rate, transferrin saturation, pyruvate, red blood cell count, white blood cell count, platelet count, or prothrombin time.

Clause 70: The method of clause 65, wherein the toxin experiment detects a change in one or more of the following channels: carbon monoxide, carboxyhemoglobin, ethanol, salicylates, acetaminophen, ethylene glycol, or caffeine.

Clause 71: The method of clause 65, wherein the stress experiment is configured to detect a change in one or more of the following channels: dehydroepiandrosterone (DHEA), dehydroepiandrosterone-S(DHEA-S), creatinine, glucose, C-reactive protein (CRP), fibrinogen, HbA1c, albumin, or ethanol.

Clause 72: The method of clause 65, wherein the fecal fat experiment detects a change in a fecal fat channel.

Clause 73: The method of clause 65, wherein the saliva experiment detects a change in a cortisol channel.

Clause 74: The method of clause 64, wherein prompting the user includes periodic prompts for the user to perform the lifestyle change in accordance with the experiment.

Clause 75: The method of clause 64, wherein prompting the user to take the blood sample includes periodic prompts for the user to take blood samples.

Clause 76: The method of clause 64, wherein the results indicate changes in health in response to the lifestyle change.

Clause 77: The method of clause 64, further comprising determining a channel as in any one of the preceding clauses and determining a change in the channel in response to the lifestyle change, and outputting the change in the channel to the user.

Clause 78: An apparatus comprising:
a processor configured with instructions for:
presenting at least one lifestyle change experiment to a user via a graphical user interface of a user device;
receiving a selection of an experiment in a computing device;
prompting, from the computing device and based on the selected experiment, a reminder to the user to perform a lifestyle change in accordance with the experiment;
prompting, from the computing device, the user to take a blood sample;
processing, in the computing device, spectroscopic data corresponding to the blood sample; and
presenting results of the selected experiment based at least on the received spectroscopic data via the graphical user interface of the user device.

Clause 79: The apparatus of clause 78, wherein the experiment comprises one or more of a metabolism experiment, a cardiovascular health experiment, an inflammation and immune function experiment, hematologic function experiment, a toxin experiment, a stress experiment, a saliva experiment or a fecal fat experiment.

Clause 80: The apparatus of clause 78, wherein the processor is configured with instructions for three or more of the metabolism experiment, the cardiovascular health experiment, the inflammation experiment, the hematologic function experiment, the toxin experiment the stress experiment, the saliva experiment or the fecal fat experiment and optionally wherein the process is configured with instructions for four or more experiments.

Clause 81: The apparatus of clause 79, wherein the processor comprises instructions for the metabolism experiment and the processor is configured with instructions to detect a change in one or more of the following channels: glucose, HbA1c (Glycated Hemoglobin), glycated albumin, ketones, β-hydroxybutyrate, albumin, total protein, blood urea nitrogen (BUN), uric acid, creatinine, glutamate, lactic acid (lactate), CO2 (bicarbonate), pH, sodium, magnesium, potassium, calcium, hydration, total body water (TBW), hematocrit, vitamin E, vitamin C, or vitamin A.

Clause 82: The apparatus of clause 79, wherein the processor comprises instructions for the cardiovascular experiment and the processor is configured with instructions to detect a change in one or more of the following channels: high density lipoprotein (HDL), low density lipoprotein (LDL), total cholesterol and other cholesterol ratios, apolipoprotein, triglycerides, or average blood pressure.

Clause 83: The apparatus of clause 79, wherein the processor comprises instructions for the inflammation experiment and the processor is configured with instructions to detects a change in one or more of the following channels: fibrinogen, C-reactive protein (CRP), uric acid, serum amyloid, globulins, IgG, IgA, IgM, or haptoglobin.

Clause 84: The apparatus of clause 79, wherein the processor comprises instructions for the hematology experiment and the processor is configured with instructions to detect a change in one or more of the following channels: hematocrit, hemoglobin, erythrocyte sedimentation rate, transferrin saturation, pyruvate, red blood cell count, white blood cell count, platelet count, or prothrombin time.

Clause 85: The apparatus of clause 79, wherein the processor comprises instructions for the stress experiment and the processor is configured with instructions to detect a change in one or more of the following channels: carbon monoxide, carboxyhemoglobin, ethanol, salicylates, acetaminophen, ethylene glycol, or caffeine.

Clause 86: The apparatus of clause 79, wherein the processor comprises instructions for the toxin experiment and the processor is configured with instructions to detect a change in one or more of the following channels: dehydroepiandrosterone (DHEA), dehydroepiandrosterone-S (DHEA-S), creatinine, glucose, C-reactive protein (CRP), fibrinogen, HbA1c, albumin, or ethanol.

Clause 87: The apparatus of clause 79, wherein the processor comprises instructions for the saliva experiment and the processor is configured with instructions to detect a change in one or more of the following channels: cortisol.

Clause 88: The apparatus of clause 79, wherein the processor comprises instructions for the fecal fat experiment and the processor is configured with instructions to detect a change in one or more of the following channels: fecal fat.

Clause 89: A system, comprising:

a spectrometer configured to perform a spectroscopy on a user's sample of blood by receiving the user's sample of blood contained within a sample holder, illuminating the user's sample of blood as the blood at least partially separates within the sample holder; and generating spectral data from the blood as the blood at least partially separates within the sample holder; and a network element communicatively coupled to the spectrometer and configured to process the spectral data to determine a plurality of biomarkers, wherein the network element comprises a recommendation engine configured to generate a plurality of experiments for the user based on the biomarkers.

Clause 90: The system of clause 89, wherein the experiments include consuming different edible substances to alter one of more of the biomarkers in a subsequent spectroscopy on a subsequent sample of blood of the user.

Clause 91: The system of clause 89, wherein the recommendation engine is further configured to alert the user to perform one or more of the experiments.

Clause 92: The system of clause 89, wherein the recommendation engine is further configured to provide information pertaining to the plurality of experiments to the user.

Clause 93: The system of clause 89, wherein the recommendation engine is further configured to track progress of the user's experiments and changes in the user's biomarkers.

Clause 94: The system of clause 89, wherein the network element is further configured to connect the user with other users to share results of the experiments.

Clause 95: The method, system, apparats or tangible medium of any one of the preceding clauses, wherein the marker comprises a biomarker.

Clause 96: The method, system, apparats or tangible medium of any one of the preceding clauses, wherein the channel comprises a spectral channel determined in response to a combination of spectral intensities of a plurality measured wavelength bands.

Clause 97: A processor configured with instructions to perform one or more steps of a method of any one of the preceding clauses.

Clause 98: A processor comprising the tangible medium of any one of the preceding clauses.

As detailed above, the computing devices and systems described and/or illustrated herein broadly represent any type or form of computing device or system capable of executing computer-readable instructions, such as those contained within the modules described herein. In their most basic configuration, these computing device(s) may each comprise at least one memory device and at least one physical processor.

The term "memory" or "memory device," as used herein, generally represents any type or form of volatile or non-volatile storage device or medium capable of storing data and/or computer-readable instructions. In one example, a memory device may store, load, and/or maintain one or more of the modules described herein. Examples of memory devices comprise, without limitation, Random Access Memory (RAM), Read Only Memory (ROM), flash memory, Hard Disk Drives (HDDs), Solid-State Drives (SSDs), optical disk drives, caches, variations or combinations of one or more of the same, or any other suitable storage memory.

In addition, the term "processor" or "physical processor," as used herein, generally refers to any type or form of hardware-implemented processing unit capable of interpreting and/or executing computer-readable instructions, including networked processors such as a server farm. In one example, a physical processor may access and/or modify one or more modules stored in the above-described memory device. Examples of physical processors comprise, without limitation, microprocessors, microcontrollers, Central Processing Units (CPUs), Field-Programmable Gate Arrays (FPGAs) that implement softcore processors, Application-Specific Integrated Circuits (ASICs), portions of one or more of the same, variations or combinations of one or more of the same, or any other suitable physical processor.

The term "network element," as used herein, generally represents any devices, systems, software, processor, or combinations thereof capable of providing communication through a network. Examples of such include network servers, computing devices, interfaces, databases, storage devices, communication interfaces, and the like.

Although illustrated as separate elements, the method steps described and/or illustrated herein may represent portions of a single application. In addition, in some embodiments one or more of these steps may represent or correspond to one or more software applications or programs that, when executed by a computing device, may cause the computing device to perform one or more tasks, such as the method step.

In addition, one or more of the devices described herein may transform data, physical devices, and/or representations of physical devices from one form to another. For example, one or more of the devices recited herein may receive image data of a sample to be transformed, transform the image data, output a result of the transformation to determine a 3D process, use the result of the transformation to perform the 3D process, and store the result of the transformation to produce an output image of the sample. Additionally or alternatively, one or more of the modules recited herein may transform a processor, volatile memory, non-volatile memory, and/or any other portion of a physical computing device from one form of computing device to another form of computing device by executing on the computing device, storing data on the computing device, and/or otherwise interacting with the computing device.

The term "computer-readable medium," as used herein, generally refers to any form of device, carrier, or medium capable of storing or carrying computer-readable instructions. Examples of computer-readable media comprise, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed.

The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of." Finally, for ease of use, the terms "including" and "having" (and their derivatives), as used in the specification and claims, are interchangeable with and shall have the same meaning as the word "comprising."

The processor as disclosed herein can be configured with instructions to perform any one or more steps of any method as disclosed herein.

It will be understood that although the terms "first," "second," "third", etc. may be used herein to describe various layers, elements, components, regions or sections without referring to any particular order or sequence of events. These terms are merely used to distinguish one layer, element, component, region or section from another layer, element, component, region or section. A first layer, element, component, region or section as described herein could be referred to as a second layer, element, component, region or section without departing from the teachings of the present disclosure.

As used herein, the term "or" is used inclusively to refer items in the alternative and in combination.

As used herein, characters such as numerals refer to like elements.

Embodiments of the present disclosure have been shown and described as set forth herein and are provided by way of example only. One of ordinary skill in the art will recognize numerous adaptations, changes, variations and substitutions without departing from the scope of the present disclosure. Several alternatives and combinations of the embodiments disclosed herein may be utilized without departing from the scope of the present disclosure and the inventions disclosed herein. Therefore, the scope of the presently disclosed inventions shall be defined solely by the scope of the appended claims and the equivalents thereof.

What is claimed is:

1. An apparatus, comprising:
   a spectrometer configured to receive a sample of blood contained within a sample holder, to illuminate the sample of blood as the sample of blood at least partially separates within the sample holder wherein a window in the sample holder comprises a height within a range from about 1 mm to about 20 mm; and
   a processor operatively coupled to the spectrometer, the processor configured with instructions to generate spectral data of the sample of blood at a plurality of wavelengths and a plurality of times corresponding to at least partial separation of the sample of blood into a plurality of components of the sample of blood.

2. The apparatus of claim 1, wherein the processor is configured with instructions to measure two of more of a high density lipoprotein, a total cholesterol, a triglyceride or a glucose of the sample of blood with a cross-validated standard errors of prediction ("CVSEP") of no more than 12 mg/dL, 20 mg/dL, 40 mg/dL, 20 mg/dL, respectively, for each of the two of more of the high density lipoprotein, the total cholesterol, the triglyceride or the glucose of the sample, with the spectral data from the plurality of times corresponding to the at least partial separation.

3. The apparatus of claim 2, wherein the two or more comprises three or more of the total cholesterol, the triglyceride or the glucose of the sample of blood with the cross-validated standard errors of prediction of no more than 12 mg/dL, 20 mg/dL, 40 mg/dL, 20 mg/dL.

4. The apparatus of claim 1, wherein the processor is configured with instructions to take substantially continuous scans of the sample of blood with a duty cycle within a range from about 10% to about 90% of a light source illuminating a detector of the spectrometer.

5. The apparatus of claim 1, wherein the spectrometer comprises a receptacle to receive the sample holder with the sample of blood contained therein with an elongate axis of the sample holder oriented toward a vertical angle of inclination to separate the sample of blood.

6. The apparatus of claim 5, wherein the sample holder comprises a blood collector, the blood collector comprising a housing and a lancet, the receptacle configured to receive the housing with the lancet positioned at least partially in a channel of the sample holder with the sample of blood.

7. The apparatus of claim 1, wherein a number of spatially resolved sample locations along the height of the sample of blood is within a range from about 2 to about 1000.

8. The apparatus of claim 1, wherein the plurality of wavelengths corresponds to a plurality of discretely resolved wavelength bands within a range from about 25 to about 1000 discretely resolved wavelength bands and the plurality of times is within a range from about 2 to about 1000.

9. The apparatus of claim 8, wherein the plurality of discretely resolved wavelength bands comprises a plurality of wavelength bands within a range from about 1500 nm to about 2000 nm.

10. The apparatus of claim 1, wherein the spectrometer comprises a maximum dimension of 170 mm.

11. The apparatus of claim 1, further comprising a digital micromirror device (DMD), wherein the sample of blood is located between the DMD and a detector.

12. The apparatus of claim 11, wherein the sample of blood is located within about 10 mm of the detector.

13. The apparatus of claim 11, wherein the processor is coupled to the DMD, wherein the processor is configured to select a region of the sample of blood, and to direct light from the region to the detector.

14. The apparatus of claim 13, wherein:
   the sample holder is configured to orient the sample of blood along a column, and to separate the sample of blood along the column; and
   the DMD and the processor are configured to selectively scan light from a plurality of regions of the sample of blood to the detector.

15. The apparatus of claim 14, wherein:
   the processor comprises instructions to sequentially configure the DMD in accordance with a plurality of Hadamard encodements.

16. The apparatus of claim 14, wherein:
   the sample holder comprises an elongate channel;
   the spectrometer is configured to receive the sample holder and align the elongate channel of the sample holder along a substantially vertical direction to separate the sample of blood into the plurality of components along the elongate channel; and
   the substantially vertical direction comprises an angle within about 20 degrees of vertical.

17. The apparatus of claim 16, wherein:
   the DMD and the processor are configured to selectively scan a first region of the sample holder comprising a first component, and to selectively scan a second region of the sample holder comprising a second component;

the processor is configured with instructions to determine an amount of time for the sample of blood to separate into the first and second components;
the first component comprises blood plasma; and
the second component comprises hematocrit.

18. The apparatus of claim 11, further comprising collection optics, wherein the detector is configured proximate to the collection optics to capture light from the illuminated sample of blood.

19. The apparatus of claim 18, wherein:
the collection optics comprise a focusing element; and
the detector comprises an Indium Gallium Arsenide (InGaAs) detector configured near a focal length of the collection optics.

20. The apparatus of claim 1, wherein the sample holder comprises a substantially transparent tube configured to separate the sample of blood into the plurality of components.

21. The apparatus of claim 20, wherein the substantially transparent tube comprises a capillary tube.

22. The apparatus of claim 21, wherein the sample holder comprises a slit aperture configured to direct light through the substantially transparent tube.

23. The apparatus of claim 1, wherein the processor is configured with instructions to take substantially continuous scans of the sample with a duty cycle within a range from about 10% to about 90% of a light source illuminating a detector of the spectrometer.

* * * * *